US012576093B2

(12) United States Patent
Lucera et al.

(10) Patent No.: US 12,576,093 B2
(45) Date of Patent: Mar. 17, 2026

(54) PHARMACEUTICAL COMPOSITION FOR SUBCUTANEOUS ADMINISTRATION

(71) Applicant: MANNKIND CORPORATION, Danbury, CT (US)

(72) Inventors: Erick Lucera, Søborg (DK); Jessica Barnes, Søborg (DK); Joseph Saldanha, Søborg (DK)

(73) Assignee: MANNKIND CORPORATION, Danbury, CT (US)

( * ) Notice: Subject to any disclaimer, the term of this patent is extended or adjusted under 35 U.S.C. 154(b) by 1011 days.

(21) Appl. No.: 17/626,709

(22) PCT Filed: Jul. 15, 2020

(86) PCT No.: PCT/EP2020/070062
§ 371 (c)(1),
(2) Date: Jan. 12, 2022

(87) PCT Pub. No.: WO2021/009266
PCT Pub. Date: Jan. 21, 2021

(65) Prior Publication Data
US 2022/0241239 A1      Aug. 4, 2022

Related U.S. Application Data

(60) Provisional application No. 62/876,425, filed on Jul. 19, 2019, provisional application No. 62/875,212, filed on Jul. 17, 2019.

(51) Int. Cl.
| | |
|---|---|
| *A61K 31/00* | (2006.01) |
| *A61K 9/00* | (2006.01) |
| *A61K 31/485* | (2006.01) |
| *A61K 47/10* | (2017.01) |
| *A61M 5/145* | (2006.01) |
| *A61M 5/168* | (2006.01) |
| *A61M 5/142* | (2006.01) |

(52) U.S. Cl.
CPC .......... *A61K 31/658* (2023.05); *A61K 9/0019* (2013.01); *A61K 31/485* (2013.01); *A61K 47/10* (2013.01); *A61M 5/14526* (2013.01); *A61M 5/1454* (2013.01); *A61M 5/16804* (2013.01); *A61M 5/14248* (2013.01); *A61M 2005/14252* (2013.01); *A61M 2205/3613* (2013.01)

(58) Field of Classification Search
CPC .. A61K 31/352; A61K 9/0019; A61M 5/1454
See application file for complete search history.

(56) References Cited

U.S. PATENT DOCUMENTS

2009/0240232 A1      9/2009   Gonnelli et al.

FOREIGN PATENT DOCUMENTS

| | | | | |
|---|---|---|---|---|
| WO | WO-2010015260 A2 * | 2/2010 | ............. | A61K 31/22 |
| WO | WO-2011046950 A1 * | 4/2011 | ......... | A61M 5/1626 |
| WO | WO-2018/071452 A1 | 4/2018 | | |
| WO | WO-2020123407 A1 * | 6/2020 | ........... | A61K 31/658 |

OTHER PUBLICATIONS

International Application No. PCT/EP2020/070062, International Search Report and Written Opinion, mailed Oct. 13, 2020.
International Application No. PCT/EP2020/070062, International Preliminary Report on Patentability, dated Jan. 27, 2022.

* cited by examiner

*Primary Examiner* — Sarah Pihonak
*Assistant Examiner* — Mikhail O'Donnel Robinson
(74) *Attorney, Agent, or Firm* — Morgan, Lewis & Bockius LLP

(57) ABSTRACT

This application concerns pharmaceutical compositions comprising cannabinoids which are suitable for subcutaneous administration in human subjects. Thus, this application concerns pharmaceutical compositions for subcutaneous administration. The pharmaceutical compositions according to the invention are particularly suitable for subcutaneous administration, which is advantageous for improving bioavailability and reducing toxicity.

19 Claims, 23 Drawing Sheets

PHARMACEUTICAL COMPOSITION FOR SUBCUTANEOUS ADMINISTRATION

This application is a U.S. National Phase of International Patent Application No. PCT/EP2020/070062, filed on Jul. 15, 2020, which claims priority to U.S. provisional application No. 62/875,212, filed on 17 Jul. 2019 and U.S. provisional application No. 62/876,425 filed on 19 Jul. 2019. The applications are expressly incorporated herein in their entirety by reference.

TECHNICAL FIELD

This application concerns pharmaceutical compositions comprising cannabinoids which are suitable for subcutaneous administration in human subjects. Thus, this application concerns pharmaceutical compositions for subcutaneous administration. The pharmaceutical compositions according to the invention are particularly suitable for subcutaneous administration, which is advantageous for improving bioavailability and reducing toxicity. The invention encompasses particular dosage regimens of the composition, for example relating to administration by continuous infusion, and optionally additional bolus administration, according to the patient's needs.

BACKGROUND OF THE INVENTION

Cannabinoid components of marijuana are known to possess therapeutic properties. Cannabinoid-based medications, such as Cannabidiol (CBD), are now being used for treatment of a wide range of medical conditions, including neuropathic pain, pain related to cancer and trauma, spasticity associated with multiple sclerosis, fibromyalgia, and others. In the United States alone, approximately 160 clinical trials with CBD are currently enrolling patients or preparing to do so. Disease targets include epilepsy, PTSD, pain, cardiovascular disease, gastrointestinal disorders, multiple sclerosis, eye conditions, spinal cord injuries, addiction, and cancer. However, the oral bioavailability of CBD is only 13 to 19%, its bioavailability via inhalation is only 11 to 45%, and CBD has a relatively short half-life resulting in inconsistent bioavailability. Furthermore, under certain oral dosing regimens, CBD-based drugs can induce liver toxicity. The low oral bioavailability, short half-life, and liver toxicity of cannabinoids has led to the investigation of alternative methods of administration that bypass the alimentary tract, which can remove upwards of 90% of the active ingested dose.

Accordingly, it would be desirable to provide cannabinoid-based medications with improved bioavailability and reduced toxicity.

BRIEF DESCRIPTION OF THE INVENTION

The present invention provides a pharmaceutical composition comprising a cannabinoid that may be administered subcutaneously.

In one aspect the invention provides a pharmaceutical composition for subcutaneous administration, said composition comprising:
    a cannabinoid;
    one or more vehicles;
    and, optionally, one or more excipients,
        wherein the concentration of the cannabinoid in the composition is at least about 25 grams per liter (g/L), and wherein the viscosity of the composition is less than about 420 centipoise (cP), as measured at 25 degrees Celsius.
In some aspects, particular and specific pharmaceutical compositions are described in detail in the description of the invention and the numbered non-limiting aspects comprised in said description of the invention.
The pharmaceutical composition according to the invention may be used therapeutically, for example for the treatment of a range of conditions as described herein.
The present invention provides a pharmaceutical composition which is suitable for subcutaneous administration. The invention provides particular dosage regimens, for example, in one aspect the pharmaceutical composition is administered to a patient via the subcutaneous route. More preferably, the dosage regimen includes continuous infusion of the pharmaceutical composition to the patient. In a further aspect the pharmaceutical composition may additionally be administered by bolus administration, that is to say that the dosage regimen may encompass administration by both continuous infusion, and by bolus administration of the pharmaceutical composition according to the invention.
In one aspect the pharmaceutical composition according to the present invention may be used for the treatment or prevention of one or more conditions selected from the group consisting of ALS, Alzheimer's, antibacterial resistant infections, anxiety, atherosclerosis, arthritis, asthma, cancer, colitis, Crohn's, diabetes, depression, endocrine disorders, epilepsy, seizures, fibromyalgia, glaucoma, heart disease, Huntington's, inflammation, irritable bowel syndrome (IBS), kidney disease, liver disease, motion sickness, nausea, neurodegeneration, neuropathic pain, neuropathy, Taxane Induced Peripheral Neuropathy, obesity, obsessive compulsive disorder (OCD), osteoporosis, Parkinson's, prion diseases, Mad Cow disease, post-traumatic stress disorder (PTSD), rheumatism, schizophrenia, sickle cell anemia, skin conditions (e.g., psoriasis, dermatitis, allergic inflammation, chronic pruritus), sleep disorders (e.g., sleep-wake disorders, apnea), spinal cord injury, stress, stroke, and traumatic brain injury (TBI), behavioral problems in children with ASD, Hyperalgesia in Patients With Deep Endometriosis, Phantom Limb Pain, and reduction of alcohol consumption.
In one aspect the pharmaceutical composition may be administered by injection.
In one aspect the composition may be administered by an ambulatory fluid delivery device. The compositions according to the present invention are particularly suited to administration via a fluid delivery device.
Said fluid delivery device may comprise a hydraulic pump chamber containing and contacting a first amount of a hydraulic fluid and configured to urge a fluid reservoir piston in a fluid reservoir to deliver the generally constant amount of the pharmaceutical composition within the fluid reservoir through a needle to the subject subcutaneously over a period of time.
In one aspect the fluid delivery device may comprise:
    a hydraulic pump chamber having a rigid sidewall containing and contacting a first amount of a hydraulic fluid and configured to urge a fluid reservoir piston in a fluid reservoir to deliver a pharmaceutical composition according to the invention within the fluid reservoir to a patient;
    a first actuator having a first actuator piston;
    a first hydraulic reservoir chamber coupled to the first actuator piston and having a second amount of the hydraulic fluid;
    a flow restrictor fluidly coupling the first hydraulic reservoir chamber and the hydraulic pump chamber to one another; a second hydraulic reservoir chamber having a third amount of the hydraulic fluid and fluidly coupled with the hydraulic pump chamber, independent of the first hydraulic reservoir; and a second actuator having a second actuator piston coupled to the second hydraulic reservoir chamber.

BRIEF DESCRIPTION OF THE DRAWINGS

The foregoing summary, as well as the following detailed description of embodiments of the compositions and fluid delivery devices, will be better understood when read in conjunction with the appended drawings of an exemplary embodiment. It should be understood, however, that the invention is not limited to the precise arrangements and instrumentalities shown.

DETAILED DESCRIPTION OF THE INVENTION

Figure 1:
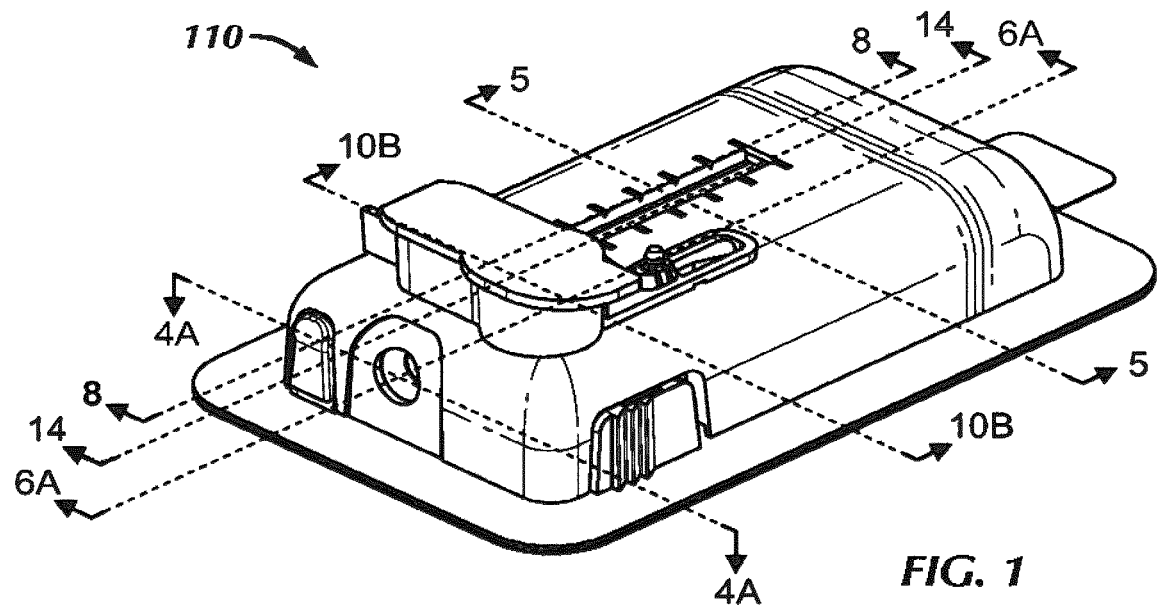
FIG. 1 is a perspective view a fluid delivery device in accordance with an exemplary embodiment of the present invention.

The methods and compositions provided herein relate to subcutaneous administration of a cannabinoid, which advantageously enables a patient to receive a lower dosage of a cannabinoid therapy, thereby avoiding possible adverse events associated with oral administration. As the compositions of the present invention are designed to increase bioavailability of cannabidiol, the amount of cannabidiol administered during any given administration may be reduced (e.g., as compared to administration methods that result in low bioavailability of cannabidiol).

*Cannabis sativa* contains more than a hundred phytocannabinoid compounds, including CBD, a non-psychotomimetic compound. CBD is of significant interest due to its anti-inflammatory, anti-oxidative and anti-necrotic protective effects, positioning it as a novel and promising therapeutic candidate in epilepsy, ophthalmology, cardiovascular disease, neurodegenerative disease, cancer, addiction, and other indications. However, current orally-directed CBD therapeutics have significant challenges as a result of poor bioavailability, short half-life, and liver toxicity concerns. Subcutaneous infusion avoids the first pass effect, providing an alternative route of administration for drugs with oral delivery challenges.

The pharmaceutical methods and compositions described herein increase the bioavailability of cannabinoid (e.g., cannabidiol (CBD)) in a patient. CBD has poor oral bioavailability—approximately 94% can be lost in the liver through the digestion. The low oral bioavailability of CBD means that greater amounts of CBD needed to be consumed orally, thus making liver damage a concern as the liver breaks down CBD into toxic metabolites. Furthermore, the liver removes the metabolites fast so the half-life of the CBD is very short when orally consumed. A non-oral CBD formulation is contemplated. A subcutaneous delivery of a CBD formulation can solve many of the problems associated with an oral delivery of CBD. With subcutaneous delivery, it is contemplated that less active ingredient (e.g., cannabinoid) can be used, there is a lower risk of liver damage, and/or the pharmaceutical composition can be produced at a lower cost as less active ingredient is needed in the formulation. The devices, methods and compositions provided herein allow a patient to receive lower dosages of a therapy thereby avoiding possible adverse events, and are designed to increase bioavailability of cannabinoid (e.g., cannabidiol) and deliver a pharmaceutical composition over a period of time.

The short half-life of CBD from the rapid metabolizing by the liver of orally administered CBD results in significant fluctuations in the bioavailability. The fluctuations in bioavailability can be detrimental to therapies especially in neurological indications. The devices and methods of the present disclosure may provide a steady supply of the pharmaceutical composition avoiding the impact from the liver eliminating the detrimental results fluctuations of pharmaceutical composition bioavailability. The subcutaneous delivery of a CBD composition further ensures a more constant exposure to CBD with less variability as demonstrated in example 2. This could potentially mean that a higher dose of CBD can be administered subcutaneously with less adverse events.

In addition, the pharmaceutical composition of the present invention may be used with a simple, easy to use, disposable device configured to deliver a continuous and/or generally constant amount of the pharmaceutical composition to a subject over a given period of time. While existing devices can be difficult to use (e.g., requiring the subject to assemble the device), expensive (e.g., having costly electrical components, and require cleaning or maintenance (e.g., re-useable devices), the devices described herein may be generally easy to use (e.g., no assembly), inexpensive (e.g., having no electronic components), and may be disposable (e.g., one time use). In addition, patients biased against using cannabinoid e.g. by smoking, can administer the pharmaceutical composition in a discreet manner by subcutaneously administration e.g. by use of a device configured to deliver a continuous and/or generally constant amount of the pharmaceutical composition to a patient over a given period of time.

In one aspect the invention provides invention provides a pharmaceutical composition for subcutaneous administration, said composition comprising:

a cannabinoid;

one or more vehicles;

and, optionally, one or more excipients, wherein the concentration of the cannabinoid in the composition is at least about 25 grams per liter (g/L), and wherein the viscosity of the composition is less than about 420 centipoise (cP), as measured at 25 degrees Celsius.

The cannabinoid may be selected from the group consisting of cannabidiol (CBD), cannabinol (CBN), cannabichromene (CBC), cannabigerol (CBG), cannabidivarin (CBV), and a derivative thereof. In a preferred aspect the cannabinoid is cannabidiol.

In a further preferred aspect the vehicle is preferably propylene glycol and/or transcutol. The ratio of the propylene glycol to the transcutol is preferably in the range of about 95:5 volume by volume (v/v) to about 85:15 v/v.

In a preferred aspect the concentration of the cannabinoid in the composition is at least about 50 or about 100 grams per liter (g/L).

In a preferred aspect the viscosity of the composition is less than about 50 or about 100 centipoise (cP), as measured at 25 degrees Celsius.

The pharmaceutical composition may preferably be administered continuously and/or as a bolus (for example administration may be generally by continuous infusion plus additional individual bolus administration if the patient requires additional cannabinoid). Bolus administration is different to continuous administration or infusion in that it is a discrete administration. The pharmaceutical composition is preferably administered by injection, more preferably by an ambulatory fluid delivery device as described herein. Such device allows bolus administration of the pharmaceutical composition by the patient activating the bolus release button when additional administration of cannabinoid is needed, e.g. in case of severe pain.

The pharmaceutical composition may be used in therapy, preferably for the treatment or prevention of one or more conditions selected from the group consisting of ALS, Alzheimer's, antibacterial resistant infections, anxiety, atherosclerosis, arthritis, asthma, cancer, colitis, Crohn's, diabetes, depression, endocrine disorders, epilepsy, seizures, fibromyalgia, glaucoma, heart disease, Huntington's, inflammation, irritable bowel syndrome (IBS), kidney disease, liver disease, motion sickness, nausea, neurodegeneration, neuropathic pain, neuropathy, Taxane Induced Peripheral Neuropathy, obesity, obsessive compulsive disorder (OCD), osteoporosis, Parkinson's, prion diseases, Mad Cow disease, post-traumatic stress disorder (PTSD), rheumatism, schizophrenia, sickle cell anemia, skin conditions (e.g., psoriasis, dermatitis, allergic inflammation, chronic pruritus), sleep disorders (e.g., sleep-wake disorders, apnea), spinal cord injury, stress, stroke, and traumatic brain injury (TBI), behavioral problems in children with ASD, Hyperalgesia in Patients With Deep Endometriosis, Phantom Limb Pain, reduction of alcohol consumption. The invention is described below in further detail. All of the definitions provided below may be applied to the present invention.

Definitions

As used herein, the term "a", "an", or "the" generally is construed to cover both the singular and the plural forms.

As used herein, the term "about" generally refers to a particular numeric value that is within an acceptable error range as determined by one of ordinary skill in the art, which will depend in part on how the numeric value is measured or determined, i.e., the limitations of the measurement system. For example, "about" can mean a range of ±20%, ±10%, or ±5% of a given numeric value.

The term "substantially" as used herein can refer to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "generally constant" as used herein can refer to a value being maintained over a period of time. In certain embodiments, a value is generally constant if the variation in the value is within ±0.5%, ±1%, ±3%, ±5%, ±10%, or ±25% over the period of time. In other embodiments, a value is generally constant if the variation in the value is within ±0.5%, ±1%, ±3%, ±5%, ±100%, or ±25% over a substantial portion (e.g., greater than 50%, 60%, 70%, 80%, 90%, 95%, or 99%) of the period of time. The period of time can be any given period of time. For example, the given period of time can be on the order of seconds, minutes, hours, days, weeks, months, or years. In some embodiments, the given period of time can be at least 1 minute (min), 5 min, 10 min, 30 min, 60 min, 2 hours, 3 hours, 4, hours, 5 hours, 6 hours, 12 hours, 24 hours, 2 days, 3 days, 5 days, 7 days, 2 weeks, 4 weeks, 2 months, 4 months, or 6 months.

As used herein, "*Cannabis*" can refer to a genus of flowering plants that includes a single species, *Cannabis sativa*, which is sometimes divided into two additional species, *Cannabis* indica and *Cannabis ruderalis*. These three taxa are indigenous to Central Asia, and South Asia. *Cannabis* has long been used for fiber (hemp), for seed and seed oils, for medicinal purposes, and as a recreational drug. Various extracts including hashish and hash oil are also produced from the plant. Suitable strains of *Cannabis* include, e.g., Indica-dominant (e.g., Blueberry, BC Bud, Holland's Hope, Kush, Northern Lights, Purple, and White Widow), Pure *sativa* (e.g., Acapulco Gold and Malawi Gold (Chamba)), and *Sativa*-dominant (e.g., Charlotte's Web, Diesel, Haze, Jack Herer, Shaman, Skunk, Sour, and Te Puke Thunder). The *Cannabis* can include any physical part of the plant material, including, e.g., the leaf, bud, flower, trichome, seed, or combination thereof. Likewise, the *Cannabis* can include any substance physically derived from *Cannabis* plant material, such as, e.g., kief and hashish.

As used herein, "cannabinoid" can refer to a class of diverse chemical compounds that act on cannabinoid receptors on cells that repress neurotransmitter release in the brain. These receptor proteins include the endocannabinoids (produced naturally in the body by humans and animals), the phytocannabinoids (found in *Cannabis* and some other plants), and synthetic cannabinoids (manufactured chemically). The most notable cannabinoid is the phytocannabinoid Δ9-tetrahydrocannabinol (THC), the primary psychoactive compound of *Cannabis*. Cannabidiol (CBD) is another major constituent of the plant, representing up to 40% in extracts of the plant resin. There are at least 85 different cannabinoids isolated from *Cannabis*, exhibiting varied effects. As used herein, "Cannabinoid" can refer to, but is not limited to, cannabidiol (CBD), cannabinol (CBN), cannabichromene (CBC), cannabigerol (CBG), cannabidivarin (CBV), or a derivative thereof. A cannabinoid can be obtained by chemical synthesis, chemical modification, or obtained from plant materials derived from one or more *Cannabis* plants. In a preferred aspect of the invention the cannabinoid is cannabidiol (CBD).

As used herein, "terpenoid" or "isoprenoid" can refer to a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. These lipids can be found in all classes of living things, and are the largest group of natural products. Plant terpenoids are used extensively for their aromatic qualities. They play a role in traditional herbal remedies and are under investigation for antibacterial, antineoplastic, and other pharmaceutical functions. Terpenoids contribute to the scent of eucalyptus, the flavors of cinnamon, cloves, and ginger, the yellow color in sunflowers, and the red color in tomatoes. Well-known terpenoids include citral, menthol, camphor, salvinorin A in the plant *Salvia divinorum*, the cannabinoids found in *Cannabis*, ginkgolide and bilobalide found in *Ginkgo biloba*, and the curcuminoids found in turmeric and mustard seed.

As used herein, "flavonoid" can refer to a class of plant secondary metabolites. Flavonoids were referred to as Vitamin P (probably because of the effect they had on the permeability of vascular capillaries) from the mid-1930s to early 50s, but the term has since fallen out of use. According to the IUPAC nomenclature, they can be classified into: flavonoids or bioflavonoids; isoflavonoids, derived from 3-phenylchromen-4-one (3-phenyl-1,4-benzopyrone) structure; and neoflavonoids, derived from 4-phenylcoumarine (4-phenyl-1,2-benzopyrone) structure.

As used herein, a pharmaceutically active ingredient (synonymously, active pharmaceutical ingredient or active ingredient) can be "substantially free of THC" if the ingredient contains less than 0.3% (w/v) of delta-9 tetrahydrocannabinol. A pharmaceutical composition comprising a pharmaceutically active ingredient is "substantially free of THC" if the pharmaceutical composition contains less than 0.3% (w/v) of delta-9 tetrahydrocannabinol. In a preferred aspect of the invention the pharmaceutical composition is substantially free of THC.

As used herein, a "*Cannabis sativa* extract" can refer to a composition obtained from *Cannabis sativa* plant materials by fluid and/or gas extraction, for example by supercritical fluid extraction (SFE) with $CO_2$. The *Cannabis sativa* extract can contain cannabinoids, selected terpenes, and also other terpenes, phytocannabinoids, and secondary metabolites. For example, the *Cannabis sativa* extract can include one or more of bisabolol, humulene, terpinene, caryophyllene, camphene, geraniol, guaiol, isopulegoll, ocimene, cymene, eucalyptol, terpinolene, and myrcene.

The *Cannabis* plant material contains suitable and desirable compounds, useful in the pharmaceutical dosage forms and methods of medical treatment described herein. The suitable and desirable compounds fall within one or more the following classes of compounds: cannabinoids, terpenoids, and flavonoids. These compounds can be obtained from the *Cannabis* in a pure or partially pure state. The compounds obtained from the *Cannabis* can be in the form of an extract of *Cannabis*, or a concentrate of *Cannabis*.

As used herein, "solvent system" can refer to one or more solvents that dissolves a solute (a chemically different liquid, solid or gas), resulting in a solution. The maximum quantity of solute that can dissolve in a specific volume of solvent system varies with temperature and pressure. The solvent system can have a specified polarity and proticity. As such, solvent system can be polar, nonpolar, protic, or aprotic, wherein each of these terms is used in a relative manner.

As used herein, "polarity" can refer to a separation of electric charge leading to a molecule or its chemical groups having an electric dipole or multipole moment Polar molecules interact through dipole-dipole intermolecular forces and hydrogen bonds. Molecular polarity is dependent on the difference in electronegativity between atoms in a compound and the asymmetry of the compound's structure. Polarity underlies a number of physical properties including surface tension, solubility, and melting- and boiling-points.

As used herein, "polar" or "polar solvent" can refer to a molecule having a net dipole as a result of the opposing charges (i.e., having partial positive and partial negative charges) from polar bonds arranged asymmetrically. Water ($H_2O$) is an example of a polar molecule since it has a slight positive charge on one side and a slight negative charge on the other. The dipoles do not cancel out resulting in a net dipole. Due to the polar nature of the water molecule itself, polar molecules are generally able to dissolve in water. Another example includes sugars (like sucrose), which have many polar oxygen-hydrogen (—OH) groups and are overall highly polar.

As used herein, "nonpolar" or "nonpolar solvent" can refer to a molecule having an equal sharing of electrons between the two atoms of a diatomic molecule or because of the symmetrical arrangement of polar bonds in a more complex molecule. For example, the boron trifluoride molecule ($BF_3$) has a trigonal planar arrangement of three polar bonds at 120°. This results in no overall dipole in the molecule. In methane, the bonds are arranged symmetrically (in a tetrahedral arrangement) so there is no overall dipole. In the methane molecule ($CH_4$) the four C—H bonds are arranged tetrahedrally around the carbon atom. Each bond has polarity (though not very strong). However, the bonds are arranged symmetrically so there is no overall dipole in the molecule. The diatomic oxygen molecule ($O_2$) does not have polarity in the covalent bond because of equal electronegativity, hence there is no polarity in the molecule Depending on the method/route of administration, pharmaceutical dosage forms come in several types. These include many kinds of liquid, solid, and semisolid dosage forms. Common pharmaceutical dosage forms include pill, tablet, or capsule, drink or syrup, and natural or herbal form such as plant or food of sorts, among many others. Notably, the route of administration (ROA) for drug delivery is dependent on the dosage form of the substance in question. A liquid pharmaceutical dosage form is the liquid form of a dose of a chemical compound used as a drug or medication intended for administration or consumption.

Exemplary pharmaceutical dosage forms include, e.g., pills, osmotic delivery systems, elixirs, emulsions, hydrogels, suspensions, syrups, capsules, tablets, orally dissolving tablets (ODTs), gel capsules, thin films, adhesive topical patches, lollipops, lozenges, chewing gum, dry powder inhalers (DPIs), vaporizers, nebulizers, metered dose inhalers (MDIs), ointments, transdermal patches, intradermal implants, subcutaneous implants, and transdermal implants.

As used herein, "dermal delivery" or "dermal administration" can refer to a route of administration wherein the pharmaceutical dosage form is taken to, or through, the dermis (i.e., layer of skin between the epidermis (with which it makes up the cutis) and subcutaneous tissues).

As used herein, "Subcutaneous delivery" can refer to a route of administration wherein the pharmaceutical dosage form is to or beneath the subcutaneous tissue layer. This is the administration route according to the present invention.

As used herein "infusion" refers to a route of administration where a pharmaceutical composition is given over a specific period, for example over 24 hours, e.g. by use of an infusion pump. As used herein, the terms "infusion", "continuous infusion" and "continuous administration" are used interchangeably.

As used herein "subcutaneous infusion" refers to a route of administration wherein a pharmaceutical composition is given subcutaneously over a specific period, for example over 24 hours, e.g. by use of an infusion pump.

As used herein, "oral delivery" or "oral administration" can refer to a route of administration wherein the pharmaceutical dosage form is taken through the mouth. Oral administration is a part of enteral administration, which also includes buccal (dissolved inside the cheek), sublabial (dissolved under the lip) and sublingual administration (dissolved under the tongue). Enteral medications come in various forms, including: tablets to swallow, chew or dissolve in water or under the tongue; capsules and chewable capsules (with a coating that dissolves in the stomach or bowel to release the medication there); time-release or sustained-release tablets and capsules (which release the medication gradually); powders or granules; teas; drops; and liquid medications or syrups.

As used herein, "ophthalmic delivery" or "ophthalmic administration" can refer to a route of administration wherein the pharmaceutical dosage form is taken to, or through, the eye.

As used herein, "pill" can refer to a small, round, solid pharmaceutical oral dosage form of medication that was in use before the advent of tablets and capsules. Pills were historically made by mixing the active ingredients with an excipient such as glucose syrup in a mortar and pestle to form a paste, then rolling the mass into a long cylindrical shape (called a "pipe"), and dividing it into equal portions, which were then rolled into balls, and often coated with sugar to make them more palatable. Today, pills include tablets, capsules, and variants thereof like caplets-essentially anything with medication that can be digested, minus the liquid forms, falls into the pill category.

"Carrier" or "vehicle" as used herein refer to carrier materials suitable for drug administration. Carriers and vehicles useful herein include any such materials known in the art, e.g., any liquid, gel, solvent, liquid diluent, solubilizer, surfactant, or the like, which is nontoxic and which does not interact with other components of the composition in a deleterious manner.

The term "therapeutically effective amount" can generally refer to the amount (or dose) of a compound or other therapy that is minimally sufficient to prevent, reduce, treat or eliminate a condition, or risk thereof, when administered to a subject in need of such compound or other therapy. In some instances, the term "therapeutically effective amount" can refer to that amount of compound or other therapy that is sufficient to have a prophylactic effect when administered to a subject. The therapeutically effective amount can vary; for example, it can vary depending upon the subject's condition, the weight and age of the subject, the severity of the disease condition, the manner of administration (e.g., subcutaneous delivery) and the like, all of which can be determined by one of ordinary skill in the art.

As used herein, "treating" or "treat", or "preventing" or "prevent", includes: (i) preventing a pathologic condition from occurring (e.g. prophylaxis); (ii) inhibiting the pathologic condition or arresting its development; (iii) relieving the pathologic condition; and/or (iv) diminishing symptoms associated with the pathologic condition.

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the disclosure is contemplated. Supplementary active ingredients can also be incorporated into the compositions.

The term "pharmaceutically acceptable excipient" is intended to include vehicles and carriers capable of being co-administered with a compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multi-binding compounds also falls within the scope of the present invention.

Subjects

The terms "subject" and "patient" are intended to have the same meaning and are used interchangeably herein. A patient treated by any of the methods or compositions described herein can be of any age and can be an adult, infant or child. In some cases, the patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). The patient can be a human or non-human subject, preferably a human subject.

Any of the compositions disclosed herein can be administered to a non-human subject, such as a laboratory or farm animal. Non-limiting examples of a non-human subject include laboratory or research animals, a dog, a goat, a guinea pig, a hamster, a mouse, a pig, a non-human primate (e.g., a gorilla, an ape, an orangutan, a lemur, or a baboon), a rat, a sheep, or a cow.

Formulations & Administration

The methods and compositions provided herein enable a patient to receive a lower dosages of a therapy thereby avoiding possible adverse events. As the compositions of the present invention are designed to increase bioavailability of cannabinoid, such as cannabidiol, the amount of cannabinoid, such as cannabidiol, administered during any given administration can be reduced (e.g., as compared to administration methods that result in low bioavailability of cannabidiol). The compositions of the present invention can be used to achieve a more constant exposure to cannabidiol, e.g. with less variability as demonstrated in example 2. This may result in less adverse events which could lead to that administration of higher doses could be tolerated.

In certain embodiments, the concentration of cannabinoid (or any derivative thereof) administered within the pharmaceutical composition can be about 0.1 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 150 mg/mL, 200 mg/mL, 300 mg/mL, 350 mg/mL, 400 mg/mL, 450 mg/mL, 500 mg/mL, 750 mg/mL, 1 g/mL, 5 g/mL, 10 g/mL, or more. Preferably, the concentration of cannabinoid (or any derivative thereof) within the pharmaceutical composition is at least about 25 mg/mL, more preferably at least about 50 mg/mL, and more preferably still at least about 100 mg/mL.

In one embodiment of the invention, the concentration of cannabinoid (or any derivative thereof) administered within the pharmaceutical composition can be about 50 mg/mL, 60 mg/mL, 70 mg/mL, 80 mg/mL, 90 mg/mL, 100 mg/mL, 125 mg/mL or 150 mg/mL.

The daily fixed dose of cannabinoid (e.g., cannabidiol) described herein, or collective dose of a combination of cannabinoids can be less than 0.1 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 150 mg, 200 mg, 300 mg, 350 mg, 400 mg, 450 mg, 500 mg, 750 mg of the cannabinoid (e.g., cannabidiol), or any derivative thereof. Preferably the daily fixed dose of cannabinoid is about 300 mg to about 500 mg, more preferably about 300 mg to about 400 mg The daily fixed dose of cannabinoid (e.g., cannabidiol) described herein, or collective dose of a combination of cannabinoids can be administered based on the weight of the patient and can be about 0.1 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 100 mg/kg, 150 mg/kg, 200 mg/kg, 300 mg/kg, 350 mg/kg, 400 mg/kg, 450 mg/kg, 500 mg/kg, 750 mg/kg of the cannabinoid (e.g., cannabidiol), or any derivative thereof. Preferably the daily fixed dose of cannabinoid (e.g. cannabidiol) is about 1 mg/kg to about 50 mg/kg, such as about 1 mg/kg to about 30 mg/kg or about 1 mg/kg to about 1 to about 10 mg/kg.

In some cases, administering a pharmaceutical composition herein to a patient can comprise administering a daily dose of 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 500 mg, 750 mg, or 1 g of cannabidiol (or any derivative thereof) to a patient.

In some cases, administering a pharmaceutical composition herein to a patient can comprise administering a daily dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 100 mg/kg, 500 mg/kg, 750 mg/kg, or 1 g/kg of cannabidiol (or any derivative thereof) to a patient.

In another example, administering a pharmaceutical composition to a patient can comprise administering a co-formulation of a first cannabinoid with a second cannabinoid. In some cases, administering a pharmaceutical composition herein to a patient can comprise administering a daily dose of 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 500 mg, 750 mg, or 1 g of the first cannabinoid and/or the second cannabinoid (or any derivative thereof) to a patient.

In further example, administering a pharmaceutical composition to a patient can comprise administering a co-formulation of a first cannabinoid with a second cannabinoid. In some cases, administering a pharmaceutical composition herein to a patient can comprise administering a daily dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 100 mg/kg, 500 mg/kg, 750 mg/kg, or 1 g/kg of the first cannabinoid and/or the second cannabinoid (or any derivative thereof) to a patient.

In certain embodiments, the volume of the pharmaceutical composition injected in a single administration (e.g., a bolus) is about 0.1 microliters (μL), 0.5 μL, 1 μL, 5 μL, 10 μL, 15 μL, 20 μL, 25 μL, 30 μL, 35 μL, 40 μL, 45 μL, 50 μL, 60 μL, 70 μL, 80 μL, 90 μL, 100 μL, 125 μL, 150 μL, 175 μL, 200 μL, 225 μL, 250 μL, 300 μL, 400 μL, 500 μL, 600 μL, 700 μL, 800 μL, 900 μL, 1 milliliter (mL), or greater than about 1 mL. In certain embodiments, the volume of the pharmaceutical composition injected in a single administration is less than about 1 milliliter (mL), 900 microliters (μL), 800 μL, 700 μL, 600 μL, 500 μL, 400 μL, 300 μL, 250 μL, 225 μL, 200 μL, 175 μL, 150 μL, 125 μL, 100 μL, 90 μL, 80 μL, 70 μL, 60 μL, 50 μL, 45 μL, 40 μL, 35 μL, 30 μL, 25 μL, 20 μL, 15 μL, 10 μL, 5 μL, 1 μL, 0.5 μL, 0.1 μL, or less than about 0.1 μL.

In certain embodiments, the volume of the pharmaceutical composition injected in a continuous administration over a given period of time is about 0.1 microliters (μL), 0.5 μL, 1 μL, 5 μL, 10 μL, 15 μL, 20 μL, 25 μL, 30 μL, 35 μL, 40 μL, 45 μL, 50 μL, 60 μL, 70 μL, 80 μL, 90 μL, 100 μL, 125 μL, 150 μL, 175 μL, 200 μL, 225 μL, 250 μL, 300 μL, 400 μL, 500 μL, 600 μL, 700 μL, 800 μL, 900 μL, 1 milliliter (mL), or greater than about 1 mL. In one embodiment the volume of the pharmaceutical composition injected in a continuous administration over a given period of time is about 500 μL, 600 μL, 700 μL, 800 μL, 900 μL, 1 mL, 1.5 mL, 2.0 mL, 2.5 mL, 3 mL, 3.5 mL, 4 mL, 4.5 mL, 5 mL, 5.5 mL, 6 mL, 6.5 mL, 7 mL, 7.5 mL, 8 mL, 8.5 mL, 9 mL, 9.5 mL or about 10 mL. The time period may be in the range of about 1 hour to about 48 hours, such as about 10 hours to about 14 hours, about 22 to about 24 hours, about 34 to about 36 hour or about 47 to about 48 hours. In one embodiment, the time period is about 24 hours. In certain embodiments, the volume of the pharmaceutical composition injected in a continuous administration over a given period of time is less than about 1 milliliter (mL), 900 microliters (μL), 800 μL, 700 μL, 600 μL, 500 μL, 400 μL, 300 μL, 250 μL, 225 μL, 200 μL, 175 μL, 150 μL, 125 μL, 100 μL, 90 μL, 80 μL, 70 μL, 60 μL, 50 μL, 45 μL, 40 μL, 35 μL, 30 μL, 25 μL, 20 μL, 15 μL, 10 μL, 5 μL, 1 μL, 0.5 μL, 0.1 μL, or less than about 0.1 μL.

In certain embodiments, the devices, methods and pharmaceutical composition of the present invention are designed to provide generally constant amount of a pharmaceutical composition to a subject over a period of time (e.g., basal dosage). In certain embodiments, the pharmaceutical composition is delivered to a subject at a generally constant rate of about 0.001 microliters per minute (μL/min), 0.005 μL/min, 0.01 μL/min, 0.05 μL/min, 0.1 μL/min, 0.2 μL/min, 0.3 μL/min, 0.4 μL/min, 0.5 μL/min, 0.6 μL/min, 0.7 μL/min, 0.8 μL/min, 0.9 μL/min, 1 μL/min, 2 μL/min, 3 μL/min, 4 μL/min, 5 μL/min, 10 μL/min, 15 μL/min, 20 μL/min, 25 μL/min, 50 μL/min, 75 μL/min, 100 μL/min, 250 μL/min, or greater than 250 μL/min.

In a preferred embodiment the pharmaceutical composition is delivered to a subject at a generally constant rate of about 0.1 μL/min, 0.2 μL/min, 0.3 μL/min, 0.4 μL/min, 0.5 μL/min, 0.6 μL/min, 0.7 μL/min, 0.8 μL/min, 0.9 μL/min, 1 μL/min, 2 μL/min, 5 μL/min, 10 μL/min, 15 μL/min, 20 μL/min, 30 μL/min, 40 μL/min, or 50 μL/min.

In one embodiment, the pharmaceutical composition comprises cannabinoid in a concentration of about 100 g/L and may be delivered to a subject at a generally constant rate of about 0.1 μL/min, 0.2 μL/min, 0.3 μL/min, 0.4 μL/min, 0.5 μL/min, 0.6 μL/min, 0.7 μL/min, 0.8 μL/min, 0.9 μL/min, 1 μL/min, 2 μL/min, 5 μL/min, 10 μL/min, 15 μL/min, 20 μL/min, 30 μL/min, 40 μL/min, or 50 μL/min.

In a more preferred embodiment, the pharmaceutical composition comprises CBD in a concentration of about 100 g/L is delivered to a subject at a generally constant rate of about 0.1 μL/min, 0.2 μL/min, 0.3 μL/min, 0.4 μL/min, 0.5 μL/min, 0.6 μL/min, 0.7 μL/min, 0.8 μL/min, 0.9 μL/min, 1 μL/min, 2 μL/min, 5 μL/min, 10 μL/min, 15 μL/min, 20 μL/min, 30 μL/min, 40 μL/min, or 50 μL/min.

Dosage Regimens

In certain embodiments, a pharmaceutical composition of the present invention can be administered to a patient as either a continuous infusion over time and/or as a bolus injection. For example, the patient may receive a continuous infusion (basal dosage), but may also receive an additional bolus administration, e.g. in the event the patient requires additional cannabinoid. One or more bolus administrations may also be delivered to the patient in addition to the continuous infusion, for example 1, 2, 3, 4, 5, 6, 7, 8, 9, or 10 additional bolus administrations over a given period of time. In one embodiment, the additional bolus administration is delivered to the patient for about 1-100 times over a given period of time, such as about 20-80 additional bolus administrations, about 30-60 additional bolus administrations or about 30-50 additional bolus administrations. The time period may be in the range of about 1 hour to about 48 hours, such as about 10 hours to about 14 hours, about 22 to about 24 hours, about 34 to about 36 hour or about 47 to about 48 hours. In one embodiment, the time period is about 24 hours.

The pharmaceutical methods and compositions described herein prevent, reduce, or eliminate disease-induced symptoms and/or side effects from medications taken by a patient to prevent, reduce, or eliminate disease-induced symptoms. Accordingly, the methods and compositions provided herein enable a patient to receive a therapy more frequently without having the dosage regimen significantly altered. The daily dose of a cannabinoid (e.g., cannabidiol) within the pharmaceutical composition provided herein can be administered to a patient in one or more doses per day. In some cases, the daily dose of the cannabinoid (e.g., cannabidiol) can be administered in a single dose. In some cases, the daily dose of the cannabinoid (e.g., cannabidiol) can be divided into about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, or greater than about 50 doses per day. For example, the daily dose of cannabinoid (e.g., cannabidiol) can be divided into 3 doses per day. In some cases, the daily dose of the cannabinoid (e.g., cannabidiol) can be divided into at least 1, 2, 3, 4, 5, 6, 7, 8, 9, 10, 15, 20, 25, 30, 35, 40, 45, 50, 55, or 60 infusions per hour. In some cases, each infusion of a composition comprising a cannabinoid (e.g., cannabidiol) may last for at least 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours, 4 hours, 4.5 hours, 5 hours, 5.5 hours, 6 hours, 12 hours, 24 hours, 48 hours, 1 week, 2 weeks, 3 weeks, 4 weeks, 2 months, 6 months, or 12 months.

The pharmaceutical compositions described herein can be administered to a patient one or more times per day. In some cases, the pharmaceutical composition can be administered to a patient one time per day. In some cases, the pharmaceutical composition can be administered to a patient at least 2 times, 3 times, 4 times 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, or 24 times per day. For example, a pharmaceutical composition can be administered to a patient 3 times per day.

The pharmaceutical compositions described herein can be administered to a patient for one or more days. In some cases, the pharmaceutical composition can be administered to a patient for one day. In some cases, the pharmaceutical composition can be administered to the patient for at least 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years, 30 years, 40 years, or 50 years. For example, an epilepsy patient can be administered a pharmaceutical formulation comprising cannabidiol for a period of at least 1 year. In some cases, the pharmaceutical composition can be administered to a patient for two or more consecutive days. In some cases, the pharmaceutical composition can be administered to a patient for two or more non-consecutive days. For example, a patient can be administered a pharmaceutical composition every day, consecutively, for 4 days. In another example, a patient can be administered a pharmaceutical composition on day 1, day 3, day 7, and day 15. In some cases, when a patient is administered a pharmaceutical composition over a period of time, the dosage amount administered to the patient on one day can be different from the dosage amount administered to the patient on a subsequent day. For example, a patient can be administered 5 mg of a pharmaceutical composition on the first day, and administered 10 mg of a pharmaceutical composition on a subsequent day, or a patient can be administered e.g. 5 mg of a pharmaceutical composition on the first day and can supply the administration with bolus injections when a need therefore is determined. The pharmaceutical compositions described herein can be effective over time. In some cases, the pharmaceutical composition can be effective for one or more days. In some cases, the duration of efficacy of the pharmaceutical composition is over a long period of time. In some cases, the efficacy of the pharmaceutical composition can be greater than 2 days, 3 days, 4 days, 5 days, 6 days, 1 week, 2 weeks, 3 weeks, or 1 month.

In some cases, the administration of any of the pharmaceutical compositions described herein can reduce the likelihood of experiencing an adverse event (e.g., disease-induced symptoms and/or side effects from medications taken by a patient to prevent, reduce, or eliminate disease-induced symptoms) across a patient pool by as much as 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. For example, if there is an 80% likelihood that Parkinson's patients in a patient pool that are administered L-dopa will experience tremors, administering to the patients a formulation comprising cannabidiol can reduce the likelihood of experiencing tremors by 75%, resulting in a 20% likelihood that the patients will experience tremors. This greater protective effect may also enable a larger population of patients, including those with pre-existing conditions, to receive treatment to which they would otherwise be precluded.

In some cases, administering a pharmaceutical composition described herein to a patient can comprise administering a dose of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 71 mg/kg, 72 mg/kg, 73 mg/kg, 74 mg/kg, 75 mg/kg, 76 mg/kg, 77 mg/kg, 78 mg/kg, 79 mg/kg, 80 mg/kg, 81 mg/kg, 82 mg/kg, 83 mg/kg, 84 mg/kg, 85 mg/kg, 86 mg/kg, 87 mg/kg, 88 mg/kg, 89 mg/kg, 90 mg/kg, 90 mg/kg, 95 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 300 mg/kg, 400 mg/kg, 500 mg/kg of a cannabinoid (e.g., cannabidiol). In one embodiment, the patient is administered subcutaneously with a cannabinoid (e.g., cannabidiol) at 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 60 mg/kg, 70 mg/kg, 80 mg/kg, 90 mg/kg, or 100 mg/kg, 150 mg/kg, or 200 mg/kg.

The pharmaceutical methods and compositions described herein generally reduce the risk that the patient will experience adverse events with the administration of a cannabinoid-based treatment. In some cases, the pharmaceutical methods and compositions described herein can reduce the risk of adverse events in the patient by 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%. In some cases, the pharmaceutical methods and compositions disclosed herein may reduce the risk of adverse events in the patient by greater than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The pharmaceutical composition of the present invention comprises one or more vehicles. Suitable vehicles may be chosen based on the active ingredient in the pharmaceutical composition. For example, CBD is severely hydrophobic, and may not readily dissolve into an aqueous solution in a stable manner. Accordingly, a vehicle may be chosen to provide a stable vehicle with which to deliver the active ingredient. It is also contemplated that one or more vehicles may be chosen to control the concentration of the active ingredient (e.g., a vehicle capable of delivering a higher dose of an active ingredient in a single administration of the pharmaceutical composition).

In a preferred aspect the one or more vehicles comprises propylene glycol. In a further preferred aspect the one or more vehicles comprises transcutol. In a further preferred aspect the one or more vehicles comprises a plurality of vehicles, and the plurality of vehicles comprises propylene glycol and transcutol. The ratio of the propylene glycol to the transcutol is preferably about 95:5 volume by volume (v/v). In one aspect the ratio of the propylene glycol to the transcutol is preferably about 85:15 volume by volume (v/v). The ratio of the propylene glycol to the transcutol is preferably in the range of about 95:5 v/v to about 85:15 v/v.

The pharmaceutical composition of the invention may optionally comprise one or more excipient. In making the compositions of this disclosure, the active ingredient can be diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art. The active ingredient in the pharmaceutical composition of the present invention is a cannabinoid, preferably CBD. In one embodiment of the invention, the pharmaceutical composition of the invention may comprise about 25 to about 100 mg/ml of cannabidiol in a vehicle comprising propylene glycol and transcutol in a ratio of about 95:5 v/v to about 85:15 v/v. In another embodiment of the invention, the pharmaceutical composition of the invention may comprise about 50 to about 100 mg/ml of cannabidiol in a vehicle comprising propylene glycol and transcutol in a ratio of about 95:5 v/v to about 85:15 v/v. In another embodiment of the invention, the pharmaceutical composition of the invention may comprise about 75 to about 100 mg/ml of cannabidiol in a vehicle comprising propylene glycol and transcutol in a ratio of about 95:5 v/v to about 85:15 v/v. In a preferred embodiment, the pharmaceutical composition of the invention may comprise about 25 to about 100 mg/ml of cannabidiol in vehicle of 95% propylene glycol and 5% Transcutol. In a more preferred embodiment, the pharmaceutical composition of the invention may comprise about 50 to about 100 mg/ml of cannabidiol in vehicle of 95% propylene glycol and 5% Transcutol. In an even more preferred embodiment, the pharmaceutical composition of the invention may comprise about 75 to about 100 mg/ml of cannabidiol in vehicle of 95% propylene glycol and 5% Transcutol. In a preferred aspect, the pharmaceutical composition of the invention may comprise 100 mg/ml of cannabidiol in vehicle of 95% propylene glycol & 5% Transcutol. The active ingredient in a pharmaceutical composition of the present disclosure can be any active ingredient known to a person of skill in the art (e.g., Apomorphine). For example, a pharmaceutical composition of the present disclosure can comprise 25 mg/ml of Apomorphine in a vehicle of 30% propylene glycol, 5% Labrasol, 0.1% sodium bisulfite & and 64.9% Sterile Water for Injection In some cases, the pharmaceutical compositions described herein may comprise an excipient that can provide long term preservation, bulk up a formulation that contains potent active ingredients, facilitate drug absorption, reduce viscosity, add flavoring, or enhance the solubility of the pharmaceutical composition. Non-limiting examples of excipients can include anti-adherents, binders (e.g., sucrose, lactose, starches, cellulose, gelatin, or polyethylene glycol), coatings (e.g., hydroxypropyl methylcellulose or gelatin), disintegrants, dyes, flavors (e.g., mint, peach, raspberry, or vanilla), glidants, lubricants, preservatives (e.g., acids, esters, phenols, mercurial compounds, or ammonium compounds), or sorbents. A pharmaceutical composition of the present invention can comprise about 1%, 2%, 3%, 4%, 5%, 6%, 7%, 8%, 9%, 10%, 15%, 20%, 25%, 30%, 35%, 40%, 45%, 50%, or greater than about 50% of the excipient by weight or by volume. For example, a pharmaceutical composition can comprise 5% of an excipient by volume. In another example, a pharmaceutical composition can comprise 8% of an excipient by weight.

In certain embodiments, a pharmaceutical composition of the present invention can comprise one or more solubilizers. As used herein, "solubilizers" include compounds such as triacetin, triethylcitrate, ethyl oleate, ethyl caprylate, sodium lauryl sulfate, sodium doccusate, vitamin E TPGS, dimethylacetamide, N-methylpyrrohdone, N-hydroxyethylpyrrolidone, polyvinylpyrrolidone, hydroxypropylmethyl cellulose, hydroxypropyl cyclodextrrns, ethanol, n-butanoL isopropyl alcohol, cholesterol, bile salts, polyethylene glycol 200-600, glycofurol, transcutol, propylene glycol, and dimethyl isosorbide and the like. A pharmaceutical composition of the present invention can comprise about 1%, 2%, 3%, 4%, 5%, 6%, 7%, 8%, 9%, 10%, 15%, 20%, 25%, 30%, 35%, 40%, 45%, 50%, or greater than about 50% of the solubilizer by weight or by volume. For example, a pharmaceutical composition can comprise 10% of a solubilizer by volume. In another example, a pharmaceutical composition can comprise 5% of a solubilizer by weight.

Generally, the solubility of any ingredient in the pharmaceutical composition is selected to control the rate of release of the pharmaceutical composition from a fluid delivery device of the present invention. In certain embodiments, the solubility of the cannabinoid in the pharmaceutical composition is about 0.1 grams per liter (g/L), about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 13 g/L, about 14 g/L about 15 g/L, about 20 g/L, about 25 g/L, about 50 g/L, about 100 g/L, about 250 g/L, about 500 g/L, about 1 kilogram per liter (kg/L), or greater than about 1 kg/L. In certain embodiments, the solubility of the cannabinoid in the pharmaceutical composition is between about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L about 0.4 to about 2 g/L, about 0.4 to about 3 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, about 11 g/L to about 12 g/L, about 12 g/L to about 20 g/L, about 20 g/L to about 50 g/L, or about 50 g/L to about 100 g/L.

In certain embodiments, the solubility of the vehicle in the pharmaceutical composition is about 0.1 grams per liter (g/L), about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 13 g/L, about 14 g/L about 15 g/L, about 20 g/L, about 25 g/L, about 50 g/L, about 100 g/L, about 250 g/L, about 500 g/L, about 1 kilogram per liter (kg/L), or greater than about 1 kg/L. In certain embodiments, the solubility of the vehicle in the pharmaceutical composition is between about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L about 0.4 to about 2 g/L, about 0.4 to about 3 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, about 11 g/L to about 12 g/L, about 12 g/L to about 20 g/L, about 20 g/L to about 50 g/L, or about 50 g/L to about 100 g/L.

In certain embodiments, the solubility of the excipient in the pharmaceutical composition is about 0.1 grams per liter (g/L), about 0.2 g/L, about 0.3 g/L, about 0.4 g/L, about 0.5 g/L, about 0.6 g/L, about 0.7 g/L, about 0.8 g/L, about 0.9 g/L, about 1 g/L, about 1.5 g/L, about 2 g/L, about 2.5 g/L, about 3 g/L, about 3.5 g/L, about 4 g/L, about 4.5 g/L, about 5 g/L, about 5.5 g/L, about 6 g/L, about 6.5 g/L, about 7 g/L, about 7.5 g/L, about 8 g/L, about 8.5 g/L, about 9 g/L, about 9.5 g/L, about 10 g/L, about 10.5 g/L, about 11 g/L, about 12 g/L, about 13 g/L, about 14 g/L about 15 g/L, about 20 g/L, about 25 g/L, about 50 g/L, about 100 g/L, about 250 g/L, about 500 g/L, about 1 kilogram per liter (kg/L), or greater than about 1 kg/L. In certain embodiments, the solubility of the excipient in the pharmaceutical composition is between about 0.2 g/L to about 0.5 g/L, about 0.2 g/L to about 1 g/L, about 0.2 to about 2 g/L, about 0.3 g/L to about 0.6 g/L, about 0.3 g/L to about 1 g/L, about 0.3 to about 2 g/L, about 0.4 to about 0.7 g/L, about 0.4 to about 1 g/L about 0.4 to about 2 g/L, about 0.4 to about 3 g/L, about 0.5 g/L to about 1 g/L, about 0.5 g/L to about 2 g/L, about 0.5 g/L to about 3 g/L, about 0.5 g/L to about 4 g/L, about 0.5 g/L to about 5 g/L, about 0.5 g/L to about 6 g/L, about 0.5 g/L to about 7 g/L, about 0.5 g/L to about 8 g/L, about 0.5 g/L to about 9 g/L, about 0.5 g/L to about 10 g/L, about 0.5 g/L to about 11 g/L, about 0.5 g/L to about 12 g/L, about 1 g/L to about 2 g/L, about 1 g/L to about 3 g/L, about 1 g/L to about 4 g/L, about 1 g/L to about 5 g/L, about 1 g/L to about 6 g/L, about 1 g/L to about 7 g/L, about 1 g/L to about 8 g/L, about 1 g/L to about 9 g/L, about 1 g/L to about 10 g/L, about 1 g/L to about 11 g/L, about 1 g/L to about 12 g/L, about 2 g/L to about 3 g/L, about 2 g/L to about 4 g/L, about 2 g/L to about 5 g/L, about 2 g/L to about 6 g/L, about 2 g/L to about 7 g/L, about 2 g/L to about 8 g/L, about 2 g/L to about 9 g/L, about 2 g/L to about 10 g/L, about 2 g/L to about 11 g/L, about 2 g/L to about 12 g/L, about 3 g/L to about 4 g/L, about 3 g/L to about 5 g/L, about 3 g/L to about 6 g/L, about 3 g/L to about 7 g/L, about 3 g/L to about 8 g/L, about 3 g/L to about 9 g/L, about 3 g/L to about 10 g/L, about 3 g/L to about 11 g/L, about 3 g/L to about 12 g/L, about 4 g/L to about 5 g/L, about 4 g/L to about 6 g/L, about 4 g/L to about 7 g/L, about 4 g/L to about 8 g/L, about 4 g/L to about 9 g/L, about 4 g/L to about 10 g/L, about 4 g/L to about 11 g/L, about 4 g/L to about 12 g/L, about 5 g/L to about 6 g/L, about 5 g/L to about 7 g/L, about 5 g/L to about 8 g/L, about 5 g/L to about 9 g/L, about 5 g/L to about 10 g/L, about 5 g/L to about 11 g/L, about 5 g/L to about 12 g/L, about 6 g/L to about 7 g/L, about 6 g/L to about 8 g/L, about 6 g/L to about 9 g/L, about 6 g/L to about 10 g/L, about 6 g/L to about 11 g/L, about 6 g/L to about 12 g/L, about 7 g/L to about 8 g/L, about 7 g/L to about 9 g/L, about 7 g/L to about 10 g/L, about 7 g/L to about 11 g/L, about 7 g/L to about 12 g/L, about 8 g/L to about 9 g/L, about 8 g/L to about 10 g/L, about 8 g/L to about 11 g/L, about 8 g/L to about 12 g/L, about 9 g/L to about 10 g/L, about 9 g/L to about 11 g/L, about 9 g/L to about 12 g/L, about 10 g/L to about 11 g/L, about 10 g/L to about 12 g/L, about 11 g/L to about 12 g/L, about 12 g/L to about 20 g/L, about 20 g/L to about 50 g/L, or about 50 g/L to about 100 g/L.

In some embodiments, the compositions described herein include excipients, other medicinal or pharmaceutical agents, carriers, adjuvants, such as preserving, stabilizing, wetting or emulsifying agents, solution promoters, and salts for regulating the osmotic pressure, osmolarity, and/or osmolality of the pharmaceutical composition. In other embodiments, the excipients, carriers, adjuvants, are useful in forming a pharmaceutically acceptable thickened composition. In some embodiments, the compositions comprise a stabilizing agent. In some embodiments, stabilizing agent is selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In a further embodiment, the chosen stabilizer changes the hydrophobicity of the composition (e.g., oleic acid, waxes), or improves the mixing of various components in the composition (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof; waxes), and/or improves the compatibility of the formula with a fluid delivery device of the present disclosure. In another embodiment, some of these stabilizers are used as solvents/co-solvents (e.g., ethanol). Other useful compositions include one or more antioxidants to enhance chemical stability where required. Suitable antioxidants include, by way of example only, ascorbic acid and sodium metabisulfite. In one embodiment, antioxidants are selected from metal chelating agents, thiol containing compounds and other general stabilizing agents.

Still other useful compositions include one or more surfactants to enhance physical stability or for other purposes. Suitable nonionic surfactants include polyoxyethylene fatty acid glycerides and vegetable oils, polyoxyethylene, hydrogenated castor oil, polyoxyethylene alkylethers, alkylphenyl ethers, octoxynol 10, and octoxynol 40.

In some embodiments, the composition comprises a suspending agent. Useful suspending agents include for example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

In some embodiments, the composition comprises an additional surfactant (co-surfactant) and/or buffering agent and/or solvent. In some embodiments, the surfactant and/or buffering agent and/or solvent is a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcelhilose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as quaternary ammonium compounds, benzalkonium chloride, cetyltrimethylammonium bromide, and lauryldimethylbenzyl-ammonium chloride. It is contemplated that the solvent may be chosen with the intended subject in mind. For example, Cremophor may be used as a solvent in a composition formulated for humans, but not for canines.

In some embodiments, the compositions described herein comprise a diluent. In some embodiments, the diluent is a salt dissolved in buffered solutions (e.g. phosphate buffered saline solution), lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylnethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, or combinations thereof. A pharmaceutical composition of the present invention can comprise about 1%, 2%, 3%, 4%, 5%, 6%, 7%, 8%, 9%, 10%, 15%, 20%, 25%, 30%, 35%, 40%, 45%, 50%, or greater than about 50% of the diluent by weight or by volume. For example, a pharmaceutical composition can comprise 5% of a diluent by volume. In another example, a pharmaceutical composition can comprise 8% of a diluent by weight.

In some embodiments, the compositions disclosed herein are isotonic. Isotonic compositions are provided by the addition of a tonicity agent. Suitable tonicity agents include, but are not limited to any pharmaceutically acceptable sugar, salt or any combinations or mixtures thereof, such as, but not limited to, dextrose and sodium chloride. In further embodiments, the tonicity agents are present in an amount from about 100 mOsm/kg to about 500 mOsm/kg.

Useful compositions also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the compositions disclosed herein comprise preservatives. Suitable preservatives for use in the compositions described herein include, but are not limited to benzoic acid, boric acid, p-hydroxybenzoates, phenols, chlorinated phenolic compounds, alcohols, quaternary compounds, quaternary ammonium compounds (e.g. benzalkonium chloride, cetyltrimethylammonium bromide or cetylpyridinium chloride), stabilized chlorine dioxide, mercurials (e.g. merfen or thiomersal), or mixtures thereof. In some embodiments, the preservative is methyl paraben. In some embodiments, the methyl paraben is at a concentration of about 0.05% to about 1.0%, about 0.1% to about 0.2%.

It may be desirable in some embodiments to reduce the viscosity of the pharmaceutical composition. In some embodiments, reducing the viscosity of the pharmaceutical composition allows for a smaller gauge needle and/or a reduced impact on delivery rate. In some embodiments, the viscosity of the pharmaceutical composition is less than about 2 cP (centipoise), less than about 50 cP, less than about 100 cP, less than about 200 cP, less than about 300 cP, less than about 420 cP, about 50 cP to about 500 cP, or about 90 cP to about 200 cP, or about 300 cP to about 500 cP, or about 300 cP to about 500 cP, and wherein the viscosity is measured at 25 degrees Celsius. In specific embodiments, the viscosity of the pharmaceutical composition is about 50 cP. In a preferred embodiment the viscosity of the pharmaceutical composition is in the range of about 1 to about 420 cP, such as in the range of about 1 to about 400 cP, in the range of about 1 to about 300 cP, in the range of about 1 to about 200 cP, in the range of about 1 to about 100 cP, in the range of about 1 to about 75 cP or in the range of about 1 to about 50 cP.

The viscosity of the pharmaceutical composition can be selected to control the rate of release of the pharmaceutical composition from fluid delivery device. In certain embodiments, the viscosity of the pharmaceutical composition is selected such that the pharmaceutical composition is released from the fluid delivery device at a rate of about 0.001 microliters per minute (μL/min), 0.005 μL/min, 0.01 μL/min, 0.05 μL/min, 0.1 μL/min, 0.2 μL/min, 0.3 μL/min, 0.4 μL/min, 0.5 μL/min, 0.6 μL/min, 0.7 μL/min, 0.8 μL/min, 0.9 μL/min, 1 μL/min, 2 μL/min, 3 μL/min, 4 μL/min, 5 μL/min, 10 μL/min, 15 μL/min, 20 μL/min, 25 μL/min, 50 μL/min, 75 μL/min, 100 μL/min, 250 μL/min, or greater than 250 μL/min. In certain embodiments, the viscosity of the pharmaceutical composition is selected such that the pharmaceutical composition is released from the fluid delivery device at a rate of about 0.001 μL/min to about 0.01 μL/min, about 0.1 μL/min to about 0.5 μL/min, about 0.2 μL/min to about 0.4 μL/min, about 0.25 μL/min to about 0.3 μL/min, about 1 μL/min to about 5 μL/min, about 1 μL/min to about 10 μL/min, about 5 μL/min to about 10 μL/min, about 5 μL/min to about 25 μL/min, about 10 μL/min to about 20 μL/min, about 10 μL/min to about 50 μL/min, or about 50 μL/min to about 250 μL/min.

The viscosity of the pharmaceutical composition of the present invention is less than about 420 centipoise (cP), as measured at 25 degrees Celsius. The viscosity may be less than about 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 90, 80, 70, 60, 50, 40, 30, 20 or 10 centipoise (cP), as measured at 25 degrees Celsius. Preferably, the viscosity of the pharmaceutical composition of the invention is less than about 100 cP as measured at 25 degrees Celsius. More preferably, the viscosity of the pharmaceutical composition of the invention is less than about 50 cP as measured at 25 degrees Celsius.

In some embodiments, a pharmaceutical composition of the present invention can comprise a base, and the base can include sodium stearyl fumarate, diethanolamine cetyl sulfate, isostearate, polyethoxylated castor oil, benzalkoniura chloride, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin, pharmaceutical acceptable salts thereof, combinations thereof, or derivatives thereof.

In certain embodiments, the pharmaceutical compositions of the present invention can comprise a plurality of vehicles, excipients, carriers, solubilizers, and the like. In any embodiment, the ratio (volume by volume or weight by weight) of a first vehicle, excipient, carrier, or solubilizer to a second vehicle, excipient, carrier, or solubilizer is less than about 1:10000, about 1:10000, about 1:5000, about 1:2500, about 1:1000, about 1:500, about 1:250, about 1:200, about 1:150, about 1:100, about 1:90, about 1:80, about 1:70, about 1:60, about 1:50, about 1:40, about 1:30, about 25:1, about 1:20, about 1:10, about 1:5, about 1:1, about 5:1, about 10:1, about 15:1, about 20:1, about 25:1, about 30:1, about 40:1, about 50:1, about 60:1, about 70:1, about 80:1, about 90:1, about 100:1, about 150:1, about 200:1, about 250:1, about 500:1, about 1000:1, about 2500:1, about 5000:1, about 10000:1, or greater than about 10000:1. For example, in one embodiment, the ratio of polypropylene glycol to transcutol is 95:5. In another embodiment, the ratio of polypropylene glycol to transcutol is 85:15.

In some embodiments, a pharmaceutical composition can comprise a cannabinoid (e.g., cannabidiol) in a solvent, and the solvent can comprise two or more ingredients. For example, a pharmaceutical composition of the present invention can comprise 100 mg/ml of cannabidiol in vehicle of 95% propylene glycol & 5% Transcutol. In another example, a pharmaceutical composition of the present invention can comprise 25 mg/ml of apomorphine in a vehicle of 30% propylene glycol, 5% labrasol, 0.1% sodium bisulfite & and 64.9% sterile water.

In one embodiments, the invention concerns a pharmaceutical composition for subcutaneous administration, said composition comprising:

a cannabinoid, e.g. cannabidiol;

a vehicle comprising propylene glycol and transcutol in a
      ratio of about 95:5 v/v to about 85:15 v/v;

wherein the concentration of the cannabinoid in the
      composition is at least about 25 grams per liter (g/L),
      and wherein the viscosity of the composition is less than about
      100 centipoise (cP), as measured at 25 degrees Celsius.

In one embodiments, the invention concerns a pharmaceutical composition for subcutaneous administration, said composition comprising:

a cannabinoid, e.g. cannabidiol;

a vehicle comprising propylene glycol and transcutol in a
      ratio of about 95:5 v/v;

wherein the concentration of the cannabinoid in the composition is at least about 25 grams per liter (g/L), and wherein the viscosity of the composition is less than about 100 centipoise (cP), as measured at 25 degrees Celsius.

Indications

Compositions of the present invention can be used to treat or prevent various diseases or conditions in subjects (e.g., humans, mammals, vertebrates), including but not limited to ALS, Alzheimer's, antibacterial resistant infections, anxiety, atherosclerosis, arthritis, asthma, cancer, colitis, Crohn's, diabetes, depression, endocrine disorders, epilepsy, seizures, fibromyalgia, glaucoma, heart disease, Huntington's, inflammation, irritable bowel syndrome (IBS), kidney disease, liver disease, motion sickness, nausea, neurodegeneration, neuropathic pain, neuropathy, Taxane Induced Peripheral Neuropathy, obesity, obsessive compulsive disorder (OCD), osteoporosis, Parkinson's, prion diseases, Mad Cow disease, post-traumatic stress disorder (PTSD), rheumatism, schizophrenia, sickle cell anemia, skin conditions (e.g., psoriasis, dermatitis, allergic inflammation, chronic pruritus), sleep disorders (e.g., sleep-wake disorders, apnea), spinal cord injury, stress, stroke, and traumatic brain injury (TBI), behavioral problems in children with ASD, Hyperalgesia in Patients With Deep Endometriosis, Phantom Limb Pain, reduction of alcohol consumption.

Epilepsy

It is contemplated that embodiments of the present invention (e.g., pharmaceutical compositions) can be used to treat, reduce the symptoms of, or prevent epilepsy by administering to the patient a therapeutically effective amount of a pharmaceutical composition of the invention. Epilepsy is a central nervous system (neurological) disorder in which brain activity becomes abnormal, causing seizures or periods of unusual behavior, sensations, and sometimes loss of awareness. Anyone can develop epilepsy. Epilepsy affects both males and females of all races, ethnic backgrounds and ages. Seizure symptoms can vary widely. Some people with epilepsy simply stare blankly for a few seconds during a seizure, while others repeatedly twitch their arms or legs. Having a single seizure does not mean you have epilepsy. At least two unprovoked seizures are generally required for an epilepsy diagnosis.

Central Pain

It is contemplated that embodiments of the present invention (e.g., pharmaceutical compositions) can be used to treat, reduce, or prevent central pain by administering to the patient a therapeutically effective amount of a pharmaceutical composition of the invention. Central pain is neuropathic pain caused by lesion or dysfunction of the central nervous system, for example, post-stroke, multiple sclerosis, neuromyelitis optica, idiopathic inflammatory transverse myelitis, spinal cord injury, brachial-radial pain syndrome, and central craniofacial pain. Cannabinoids have demonstrated activity in central pain associated with multiple sclerosis.

Fibromyalgia

It is contemplated that embodiments of the present invention (e.g., pharmaceutical compositions) can be used to treat, reduce or prevent fibromyalgia by administering to the patient a therapeutically effective amount of a pharmaceutical composition of the invention. Fibromyalgia (FM) is a common, chronic, idiopathic condition characterized by diffuse body pain and the presence of pressure allodynia.

Migraine

It is contemplated that embodiments of the present invention (e.g., pharmaceutical compositions) can be used to treat, reduce or prevent migraines by administering to the patient a therapeutically effective amount of a pharmaceutical composition of the invention. Migraine is a common episodic disorder of head and facial pain. Migraine attacks can be acutely treated with NSAIDs, acetaminophen, a variety of triptans (e.g., sumatriptan), and antiemetics, but some migraine sufferers have pain unresponsive to existing treatment options.

Multiple Sclerosis

It is contemplated that embodiments of the present invention (e.g., pharmaceutical compositions) can be used to treat, reduce or prevent multiple sclerosis by administering to the patient a therapeutically effective amount of a pharmaceutical composition of the invention. Nearly all multiple sclerosis (MS) patients of all subtypes have one or more symptoms of spasticity, pain, disturbed sleep, bladder dysfunction, and fatigue. Disease modifying therapies do not improve symptoms. Spasticity affects over 80% of MS patients; 34% have moderate, severe, or total spasticity. Severe spasticity is related to cost and level of care, and is independently related to quality of life in MS.

Functional Chest Pain

It is contemplated that embodiments of the present invention (e.g., pharmaceutical compositions) can be used to treat, reduce or prevent functional chest pain by administering to the patient a therapeutically effective amount of a pharmaceutical composition of the invention. Functional chest pain, sometimes called non-GERD, non-cardiac chest pain, is a functional gastrointestinal disorder where discomfort of upper GI structures is perceived in the chest. In addition to consuming medical resources to rule out other treatable conditions, functional chest pain causes distress for patients. It may be treated with tricyclic antidepressants or serotonin norepinephrine reuptake inhibitors, but not all patients respond.

Rheumatoid Arthritis and Osteoarthritis

It is contemplated that embodiments of the present invention (e.g., pharmaceutical compositions) can be used to treat, reduce or prevent rheumatoid arthritis by administering to the patient a therapeutically effective amount of a pharmaceutical composition of the invention.

Alzheimer's Disease

It is contemplated that embodiments of the present invention (e.g., pharmaceutical compositions) can be used to treat, reduce or prevent Alzheimer's disease by administering to the patient a therapeutically effective amount of a pharmaceutical composition of the invention. Alzheimer's disease (AD) is the most common cause of dementia, affecting −5.3 million people in the US. Agitation and aggression are risk factors for institutionalization of patients with dementia. It is contemplated that cannabinoids can improve anorexia and decrease agitation in AD patients and reduced nighttime agitation.

Inflammatory Bowel Disease

It is contemplated that embodiments of the present invention (e.g., pharmaceutical compositions) can be used to treat, reduce or prevent inflammatory bowel disease by administering to the patient a therapeutically effective amount of a pharmaceutical composition of the invention. Inflammatory bowel disease (IBD) involves chronic inflammation of all or part of the digestive tract. IBD primarily includes ulcerative colitis and Crohn's disease. Both usually involve severe diarrhea, pain, fatigue, and weight loss. IBD can be debilitating and sometimes leads to life-threatening complications.

Skeletal Muscle Contusion

It is contemplated that embodiments of the present invention (e.g., pharmaceutical compositions) can be used to treat, reduce or prevent skeletal muscle contusion by administering to the patient a therapeutically effective amount of a pharmaceutical composition of the invention. Skeletal muscle contusion indicates a direct, blunt, compressive force to a muscle.

Contusions are one of the most common sports-related injuries. The severity of contusions ranges from simple skin contusions to muscle and bone contusions to internal organ contusions.

Tourette Syndrome and Chronic Motor or Vocal Tic Disorders

It is contemplated that embodiments of the present invention (e.g., pharmaceutical compositions) can be used to treat, reduce or prevent Tourette Syndrome and Chronic Motor or Vocal Tic Disorders by administering to the patient a therapeutically effective amount of a pharmaceutical composition of the invention. Tourette syndrome (TS) is a neurodevelopmental condition characterized by chronic motor and vocal tics with an onset before 18 years of age. Tics are rapid, recurrent, purposeless movements or vocalizations. Persistent Motor or Vocal Tic Disorder are two recognized syndromes characterized by isolated motor or vocal tics, respectively. In other aspects, the conditions of Persistent Motor or Vocal Tic Disorder are similar to TS.

TS is largely considered to be a disease of childhood, with onset around 5 years of age. Tics typically increase in severity until mid-teens and then decline in late adolescence and early adult life. An objective re-examination of the persistency of tics into adulthood indicated that 90% of adults diagnosed as children with TS still had tics.

TS is highly heritable with variable expression. Males are more commonly affected than females, with the male-to-female ratio between three and four to one. TS frequently occurs together with attention deficit hyperactivity disorder (ADHD) and obsessive-compulsive disorder (OCD). The impact of TS is substantial, with a decreased quality of life often associated with unemployment, underachievement, increased tic severity, the presence of co-morbidities such as OCD, ADHD, anxiety and depression.

Attention Deficit and Hyperactivity Disorder (ADHD)

It is contemplated that embodiments of the present invention (e.g., pharmaceutical compositions) can be used to treat, reduce or prevent ADHD by administering to the patient a therapeutically effective amount of a pharmaceutical composition of the invention. ADHD is a chronic mental health condition with inattention, hyperactivity and impulsive behavior that occur in multiple settings and affect function in academic, social or occupational activities. Symptoms start in childhood and may persist into adulthood. It is estimated that from 8 to 11% of US school age children have ADHD and 4% of US adults have adult ADHD. Diagnosis can be made according to criteria in the Diagnostic and Statistical Manual of Mental Disorders, Version 5. Target symptoms can be monitored through ADHD-specific rating scales. Adults with ADHD can have an improvement in symptoms when using *cannabis*.

Obsessive-Compulsive Disorder (OCD)

It is contemplated that embodiments of the present invention (e.g., pharmaceutical compositions) can be used to treat, reduce or prevent OCD by administering to the patient a therapeutically effective amount of a pharmaceutical composition of the invention. Obsessive-compulsive disorder (OCD) is a chronic mental health condition characterized by recurrent intrusive thoughts, images, or urges (obsessions) that typically cause anxiety or distress, and by repetitive mental or behavioral acts (compulsions) that the individual feels driven to perform. OCD typically starts in adolescence, persists throughout a person's life, and produces substantial impairment in functioning due to the severe and chronic nature of the illness. A lifetime prevalence of 2% is estimated in the US. Diagnosis can be made according to criteria in the Diagnostic and Statistical Manual of Mental Disorders, Version 5. Target symptoms can be monitored through OCD-specific rating scales. Numerous lines of evidence suggest the cortico-striato-thalamo-cortical circuits to the pathophysiology of OCD. Patients with OCD frequently have the diagnoses of an anxiety disorder. Treatments targeted towards anxiety are often considered for OCD treatment.

Traumatic Brain Injury (TBI)

It is contemplated that embodiments of the present invention (e.g., pharmaceutical compositions) can be used to treat, reduce or prevent TBI by administering to the patient a therapeutically effective amount of a pharmaceutical composition of the invention. Traumatic brain injury (TBI) is a leading cause of death in North America for younger than 45. Survivors may live with significant disabilities, resulting in major socioeconomic burden.

The pathophysiology of TBI-related brain injury is divided into two separate concepts of primary brain injury and secondary brain injury. The acute brain damage after traumatic brain injury TBI results from primary injury, which is the result of the external mechanical force leading to contusion, laceration, and coagulopathy.

Secondary brain injury immediately follows the primary injury, which is mediated with a complex cascade of molecular, cellular and immune responses, resulting in neuroinflammation, excitotoxicity, oxidative stress, disruption of calcium homeostasis, mitochondrial dysfunction, neuronal injury, and neuronal death. Repetitive bouts of mild TBI are found in military combatants and sporting events, and can lead to chronic traumatic encephalopathy or 'dementia pugilistica'. Chronic traumatic encephalopathy (CTE) is clinically marked by memory impairment, emotional lability, personality changes and may eventually progress to dementia. Pathologically, these changes are characterized by atrophy, deposits of abnormal proteins composed of beta-amyloid, phosphorylated tau and transactivation response DNA-binding protein 43 (TDP-43). Similar pathological changes may be seen years after a single episode of TBI. Interruption of the process of secondary brain injury has been the focus of neuroprotective treatments to prevent the consequences of TBI.

In the responses to secondary damage, the inflammatory response associated with other processes likely plays a key role in causing neuropathology following TBI. Inflammation has been recognized to be one of the important hallmarks in TBI. Proinflammatory markers such as cytokines interleukin (TL)-ip, IL-6, and tumor necrosis factor alpha (T Fa), and chemokines released from activated astroglial cells and infiltrated leukocytes in the brain and cerebrospinal fluid are robustly elevated after TBI, and may be correlated with the outcome. Histological changes found in the chronic state demonstrate neurofibrillary tangles and aggregates of tau protein. Chronic traumatic encephalopathy is now considered a 'tauopathy', with histological similarity to features observed in other degenerating diseases with aggregates of tau protein.

Appropriate and timely intervention during this critical window following the primary injury after TBI may significantly reduce secondary brain damage and eventually prevent occurrence of CTE.

Stroke

It is contemplated that embodiments of the present invention (e.g., pharmaceutical compositions) can be used to treat, reduce the occurrence of or prevent stroke by administering to the patient a therapeutically effective amount of a pharmaceutical composition of the invention. Stroke causes neuronal death when the blood supply to a portion of the brain is blocked. Ischemic stroke is more common than hemorrhagic stroke, and atherosclerosis is the most common cause of local disease within the arteries that supply the brain. Like Traumatic Brain Injury, the pathophysiology of stroke is conceptually divided into two areas, a primary area strictly dependent on the interrupted blood supply, and a secondary area of brain at risk due to the elaboration of factors due to dying neurons, activated glial and astrocytic cells, and inflammatory cellular influx.

Amyotrophic Lateral Sclerosis (ALS)

It is contemplated that embodiments of the present invention (e.g., pharmaceutical compositions) can be used to treat, reduce or prevent ALS by administering to the patient a therapeutically effective amount of a pharmaceutical composition of the invention. Amyotrophic Lateral Sclerosis (ALS), also known as Lou Gehrig's disease, is a rapidly progressive, neurodegenerative disorder characterized by the selective loss of motor neurons in the brain and spinal cord, leading to complete paralysis and death usually within 3-5 years from diagnosis. While the majority of ALS cases are sporadic, a growing number of familial forms of the disease (~10% of total cases) are recognized, including those caused my mutations to the genes encoding superoxide dismutase-1 (SOD-1), TAR-DNA binding protein-43 (TDP-43), or FUS (fused in sarcoma) protein, as well as by a hexanucleotide repeat expansion in the non-coding region of the gene C90RF72. The disease still lacks an effective treatment for symptoms and/or disease progression.

Huntington's Disease

It is contemplated that embodiments of the present invention (e.g., pharmaceutical compositions) can be used to treat, reduce or prevent Huntington's Disease by administering to the patient a therapeutically effective amount of a pharmaceutical composition of the invention. Huntington's Disease (HD) is a genetic, fatal, progressive neurodegenerative disorder characterized by cognitive, psychiatric, and motor disturbances. HD is caused by a polymorphic trinucleotide CAG repeat expansion in the huntingtin gene and is inherited in an autosomal dominant manner. There are approximately 30,000 people in the US presenting with the disease, with another 200,000 at risk of inheriting it. Medications for symptomatic relieve in HD are currently available but limited, and no treatment can prevent the decline associated with the disease.

Glaucoma

It is contemplated that embodiments of the present invention (e.g., pharmaceutical compositions) can be used to treat, reduce or prevent Glaucoma by administering to the patient a therapeutically effective amount of a pharmaceutical composition of the invention. Glaucoma is a group of optic neuropathies characterized by selective loss of retinal ganglion cells (RGCs) and progressive optic nerve damage leading to irreversible visual field loss and blindness. Elevated intraocular eye pressure (IOP) constitutes a major risk factor for optic nerve damage in glaucoma. All currently approved glaucoma treatments work by modulating IOP without directly preventing RGC loss.

Atopic Dermatitis (AD)

It is contemplated that embodiments of the present invention (e.g., pharmaceutical compositions) can be used to treat, reduce or prevent AD by administering to the patient a therapeutically effective amount of a pharmaceutical composition of the invention. Atopic Dermatitis (AD), also known as eczema, is a common chronic inflammatory skin disorder associated with dysfunction of the body's immune system. AD affects up to 20% of children but can extend to adulthood affecting up to 3% of adults. In AD the skin becomes extremely itchy. Excessive scratching leads to redness, swelling, cracking, "weeping" clear fluid and crusting of the skin. A functional cannabinoid signaling system is present in the skin and mediates multiple aspects of skin biology.

Parkinson's Disease (PD)

It is contemplated that embodiments of the present invention (e.g., pharmaceutical compositions) can be used to treat, reduce or prevent PD by administering to the patient a therapeutically effective amount of a pharmaceutical composition of the invention. Parkinson's Disease (PD) is a progressive neurodegenerative disorder that affects the basal ganglia. Characteristic motor symptoms of PD include tremor, rigidity, bradykinesia and muscle stiffness. The motor symptoms of PD are caused predominantly by alterations in the substantia nigra, including death of nigral dopaminergic neurons. Current treatment of PD, such as dopamine replacement therapies, serve to alleviate symptoms, but no disease-modifying therapies are available. Exogenous cannabinoids have been found to have beneficial effects on PD symptoms.

Autism

It is contemplated that embodiments of the present invention (e.g., pharmaceutical compositions) can be used to treat, reduce or prevent Autism by administering to the patient a therapeutically effective amount of a pharmaceutical composition of the invention. Autism spectrum disorder (ASD) is a group of common neurodevelopmental disorders characterized by repetitive behaviors and impairments with social interaction and communication. Autism affects approximately 22 million people worldwide and approximately 1.5% of children in the United States. Symptoms vary greatly between individuals but begin in early childhood and affect daily functioning. Autism has a strong genetic link and numerous genes have been associated with the disorder, including more than 30 mutations in genes for neuroligin 1-4, which are postsynaptic cell-adhesion molecules that control synaptic properties.

Dystonias

It is contemplated that embodiments of the present invention (e.g., pharmaceutical compositions) can be used to treat, reduce or prevent Dystonia by administering to the patient a therapeutically effective amount of a pharmaceutical composition of the invention. Dystonias are a heterogeneous group of movement disorders, conceptually recharacterized in the late 1980s by purported involvement of the basal ganglia and clinically characterized by sustained or intermittent muscle contractions causing abnormal, often repetitive, movements, postures, or both. Dystonic movements are typically patterned, twisting, and may be tremulous. Dystonia is often initiated or worsened by voluntary action and associated with overflow muscle activation.

Dystonias may be classified based on clinical characteristics (age at onset, body distribution, temporal pattern, coexistence of other movement disorders, and other neurologic manifestations) and etiologic characteristics (other nervous system pathology and the pattern of inheritance). Primary dystonias arise in children, are often systemic, and may be accompanied by other clinical features, such as spasticity or encephalopathy, and may have a genetic basis. Primary dystonias in adults are usually isolated, related to practiced activities, and more common than those of children, and are idiopathic and not progressive. Example primary isolated dystonias are blepharospasm, cervical dystonia (torticollis), and writer's cramp. There is unmet need in dystonias for oral medications that improve function.

Patient Sub-Groups

In one aspect of the invention, the pharmaceutical composition may be administered to a particular sub-group of patients. For example, in one embodiment the patient may be unable to tolerate oral administration, or inhalation of the cannabinoid. In one aspect the patient may have nausea and/or vomiting, or any other symptom that precludes them from oral administration or inhalation of a cannabinoid as described herein. In one aspect the patient may not wish to be seen taking the cannabinoid via oral or inhalation routes e.g. in view of social considerations. The present invention is advantageous where the patient cannot, or will not (or does not wish to), take the cannabinoid via other routes, for example oral or inhalation routes.

Methods of Treatment

The present invention encompasses methods of treatment corresponding to all pharmaceutical composition and uses thereof as described herein. For example, the invention encompasses a pharmaceutical composition as described herein in a method of treating a patient as described herein, wherein said method comprises administering a pharmaceutical composition as described herein to said patient. Said administration may be by any of the routes or dosage regimens as described herein. Said method of treatment may involve a step of administering said pharmaceutical composition to said patient subcutaneously, for example by continuous infusion, and optionally by bolus administration. All of the aspects as described herein are equally applicable to corresponding methods of treatment.

Device & Methods of Use

The device as described herein may be used to administer any of the pharmaceutical compositions of the invention described herein, and which is referred to as a fluid below.

Referring to the drawings in detail, wherein like reference numerals indicate like elements throughout, there is shown in FIGS. 1-23C a fluid delivery device, generally designated 110, in accordance with an exemplary embodiment of the present invention. The fluid delivery device 110 can include one or more features described herein which facilitate or improve accurate delivery of a fluid and ease of use by a user or patient. The benefits provided by these features translate readily to improved patient compliance and improved therapeutic outcome.

In one embodiment, the fluid delivery device 110 is a discrete ambulatory delivery pump. The fluid delivery device 110 can be single use, disposable and incapable of reuse. In preferred embodiments, the fluid delivery device 110 is completely mechanical and hydraulic and has no electronic components or aspects. The fluid delivery device 110 can provide excellent therapeutic capability in a small, single use, disposable package and can be produced using high volume manufacturing fabrication (e.g., injection molding) and assembly processes, allowing for low cost-of goods. Devices as described herein can be used for a broad range of applications, including, but not limited to, clinical applications (administration of medicaments, etc.) and bio-medical research (e.g., microinjection into cells, nuclear or organelle transplantation, isolation of single cells or hybridomas, etc.).

The fluid delivery device 110 is a device for dispensing, delivering, or administering the fluid or agent to the user or patient. The fluid can be any therapeutic agent. In one embodiment, the fluid is a low viscosity gel agent. In one embodiment, the fluid is an analgesic agent. In other embodiments, the fluid can be, but is not limited to, opiates and/or other palliatives or analgesics, hormones, psychotropic therapeutic compositions, or any other drug or chemical whose continuous dosing is desirable or efficacious for use in treating patients. Single fluids and combinations of two or more fluids (admixed or co-administered) can be delivered using the fluid delivery device 110. As used herein "patients" or "user" can be human or non-human animals; the use of the fluid delivery device 110 is not confined solely to human medicine, but can be equally applied to veterinarian medicine. In a preferred aspect the patient or user is a human.

The fluid delivery device 110 can dispense the fluid over a sustained period of time (i.e., basal delivery). In one embodiment, the fluid delivery rate is continuously or near continuously delivered to the user over the sustained period of time. The fluid delivery device 110 can also be capable of dispensing a supplementary amount of fluid, in addition to the basal amount, on demand, under patient control (i.e., bolus delivery). In one embodiment, as discussed further below, the bolus amount delivered in a single, selectable administration is pre-determined. In preferred embodiments, the fluid delivery device 110 is hydraulically actuated and comprises one or more reservoirs or chambers containing hydraulic fluid of a suitable viscosity for transferring power from one or more actuators to the fluid and controlling the delivery rate as discussed further below.

Figure 3:
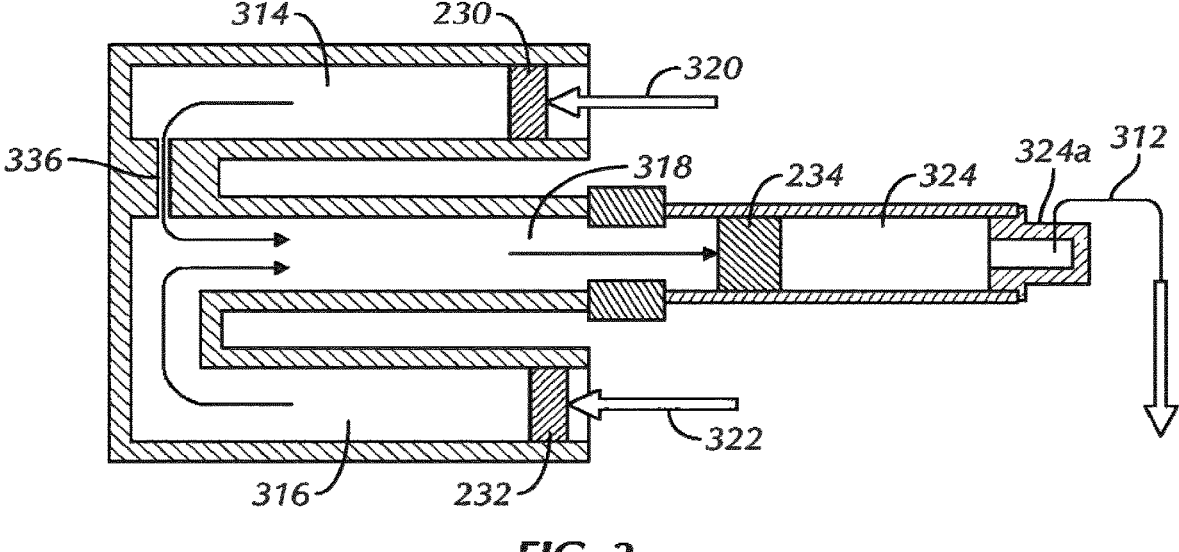
FIG. 3 is a schematic top, cross sectional view of a fluid delivery device in accordance with an exemplary embodiment of the present invention.

One exemplary embodiment of the fluid delivery device 110 is shown in the schematic of FIG. 3, illustrating select components and their relationships. The fluid delivery device 110 can have a first operable state for dispensing or delivering the fluid through an infusion set or needle 312 at a continuous or sustained basal dosage and a second operable state for delivering the fluid through the needle 312 at a bolus dosage. In some embodiments, the fluid delivery device can be in both the first and second operable states concurrently, i.e., delivering a bolus dose in addition to a basal dose of fluid. In one embodiment, the bolus dosage is a fixed incremental dosage. In another embodiment, the bolus function is capable of delivering multiple discrete bolus increments when activated by the user. In certain embodiments, the basal rate of delivery is predetermined and preset.

In one embodiment, the fluid delivery device 110 contains three hydraulic reservoirs or chambers, a hydraulic basal chamber 314, a hydraulic bolus chamber 316 and a hydraulic pump chamber 318. In some embodiments, the hydraulic bolus chamber 314 shares a common chamber with the hydraulic pump chamber 318 and/or the flow between the hydraulic bolus chamber 316 and the hydraulic pump chamber 318 is unrestricted as described further herein. In a preferred embodiment, the hydraulic basal and bolus chambers 314, 316 are separately and independently actuated by separate and independent basal and bolus actuators 320, 322.

Referring to FIG. 3, in one embodiment, the hydraulic basal and bolus chambers 314, 316 act on the hydraulic pump chamber 318 which in turn acts on a fluid reservoir or delivery chamber 324, containing the fluid. In other embodiments, the hydraulic basal and bolus chambers 314, 316 each act on a distinct pump chamber and each pump chamber is functionally connected to a separate fluid reservoir (not shown).

Figure 2:
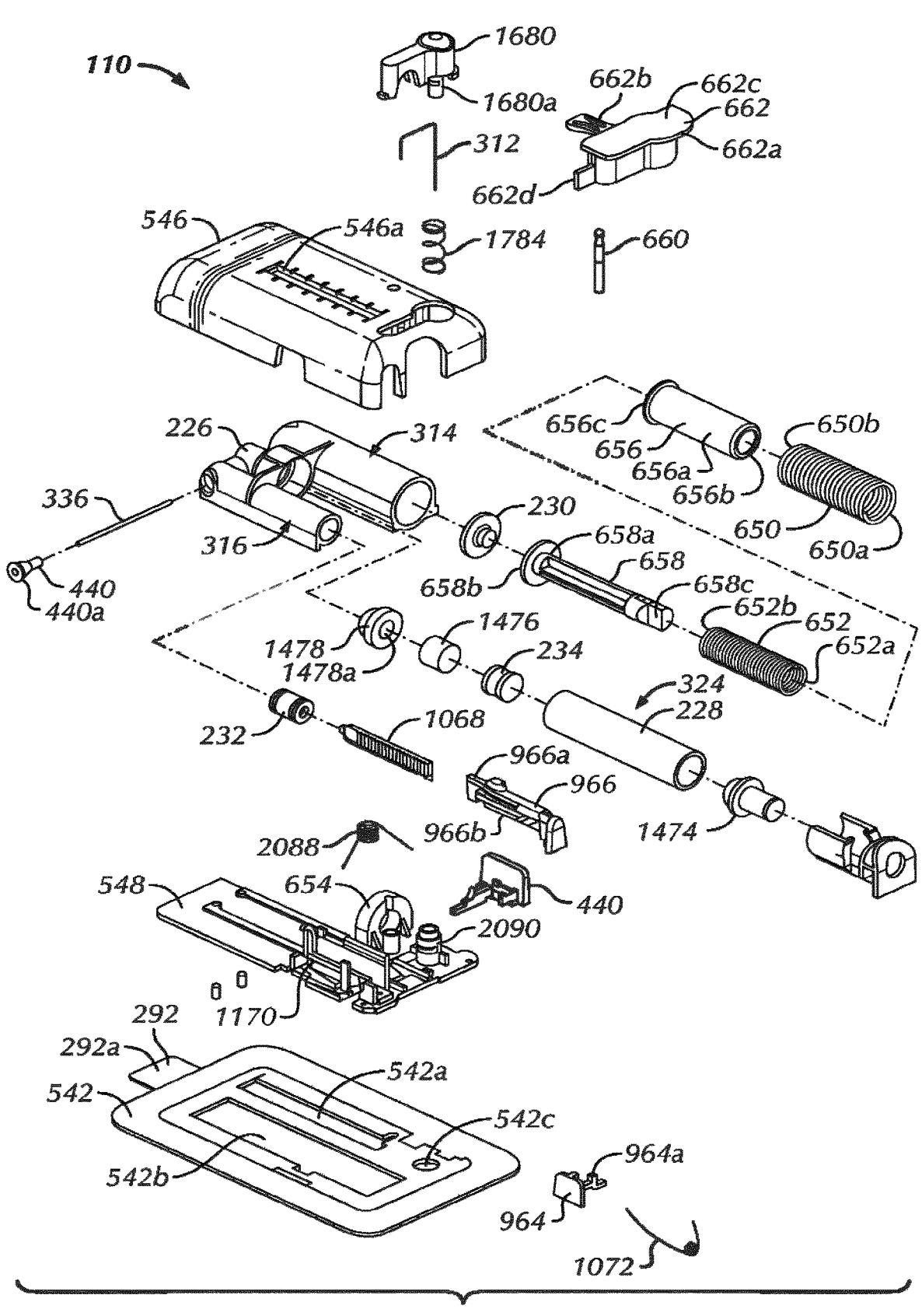
FIG. 2 is an exploded perspective view of the fluid delivery device shown in FIG. 1.

Referring to FIG. 2, the hydraulic basal, bolus and pump chambers 314, 316, 318 can be defined by a manifold 226. In one embodiment, the manifold 226 is an integral one piece component 226. In one embodiment, the manifold 226 is comprised of a polymer. In one embodiment, the manifold 226 is comprised of polyvinyl chloride (PVC). In one embodiment, the fluid reservoir 324 and a portion of the hydraulic pump chamber 318 are defined by a fluid cartridge 228. In one embodiment, the fluid cartridge 228 is comprised of a polymer. In one embodiment, the fluid cartridge 228 is comprised of Topas 6017 S-04. The hydraulic basal, bolus and pump chambers 314, 316, 318 and the fluid reservoir 324 can be cylindrical. In other embodiments, the hydraulic pump chambers 314, 316, 318 and the fluid reservoir 324 have any cross sectional shape such as square, rectangular or triangular. In one embodiment, a first moveable barrier 230 separates the basal actuator 320 and the hydraulic basal chamber 314. In one embodiment, a second moveable barrier 232 separates the bolus actuator 322 and the hydraulic bolus chamber 316. In one embodiment, a third moveable barrier 234 separates the hydraulic pump chamber 318 and the fluid reservoir 324. The first, second and third moveable barriers 230, 232, 234 can be pistons as described further below. In other embodiments, the first, second and third moveable barriers 230, 232, 234 are any barriers that can transfer movement between two chambers such as membranes or expandable walls.

The hydraulic basal and bolus chambers 314, 316 can be parallel, spaced on either side of and generally aligned with the hydraulic pump chamber 318 and the fluid reservoir 324 as illustrated in order to provide a more compact configuration. In one embodiment, the hydraulic pump chamber 318 is provided toward one side of the fluid delivery device 110. In other embodiments, the hydraulic basal, bolus and pump chambers 314, 316, 318 are arranged in any configuration that allows fluid communication and achieves the desired outer shape of the fluid delivery device 110 such as stacked in a triangle configuration.

The basal actuator 320 can act on the hydraulic basal chamber 314 containing a hydraulic fluid to pressurize the hydraulic basal chamber 314 and force a hydraulic fluid through a flow restrictor 336 into the hydraulic pump chamber 318. Generally, but not necessarily, the hydraulic fluid in hydraulic pump chamber 318 can be identical or similar in composition to the hydraulic fluid in hydraulic basal chamber 314. Actuation of the basal actuator 320 can result in a flow of hydraulic fluid from hydraulic basal reservoir 320 into the hydraulic pump chamber 318 at a reduced rate as compared to if the flow restrictor 336 was not provided. As the volume of hydraulic fluid in the hydraulic pump chamber 318 increases, the third moveable barrier 234 is displaced, compressing or reducing the volume of the fluid reservoir 324 and causing the fluid contained therein to be expelled through an output orifice or needle 312 at a sustained basal rate. In one embodiment, the basal rate is substantially constant.

In some embodiments, a bolus actuator 322 independently acts on the hydraulic bolus chamber 316. In one embodiment, the bolus actuator 322 acts directly on the hydraulic pump chamber 318. It should be understood, however, that the invention is not limited to devices comprising both a basal and a bolus capability. Devices for use according to the invention having one or more features described herein can comprise a basal capability, a bolus capability, or both basal and bolus capabilities.

Both hydraulic bolus chamber 316 and hydraulic pump chamber 318 can contain hydraulic fluid of an appropriate viscosity. Generally, but not necessarily, the composition of the hydraulic fluid in hydraulic pump chamber 318 will be identical or similar to the composition of the hydraulic fluid in hydraulic basal and bolus chambers 314, 316. Actuation or displacement of the bolus actuator 322 independently displaces the third moveable barrier 234, compressing or reducing the volume of fluid reservoir 324 and causing the fluid contained therein to be expelled through an output orifice such as the needle 312. Concurrent operation of both the basal and bolus actuators 320, 322 causes compression of fluid reservoir 324 by an amount greater than operation of either actuator alone.

When present, both the basal and bolus actuators 320, 322 can be integrated within the hydraulically actuated system in a manner that allows each function to provide independent displacement force onto a common movable barrier 234, which in turn displaces fluid from within a common fluid reservoir 324 to dispense the fluid from the device. In other embodiments, the basal and bolus actuators 320, 322 can be integrated within the hydraulically actuated system in a manner that allows each function to provide independent displacement force onto separate moveable barriers (not shown), which in turn displace fluid from within separate fluid reservoirs (not shown). Examples of a multi-cartridge fluid delivery devices for use with the inventions presented herein are disclosed in U.S. Patent Application Publication No. 2009/0240232 which is hereby incorporated by reference in its entirety.

In one embodiment, the fluid delivery device 110 utilizes a combination of force, high, very high or ultra high viscosity fluid, and flow restriction to deliver the fluid on a continuous or sustained basis. The flow restrictor 336 can facilitate continuous delivery of fluid at a basal rate by, among other aspects, creating a large pressure differential or pressure drop between the hydraulic basal chamber 314 and the hydraulic pump chamber 318, allowing the system to tolerate a wider range of frictional variations in the system such as movement of the third movable barrier 234 within the fluid cartridge 228, tolerate small changes in the resistance to flow, and overcome potential occlusions in the flow path. In one embodiment, the pressure differential between the hydraulic basal chamber 314 and the hydraulic pump chamber 318 during use is approximately 10:1. In one embodiment, the pressure differential between the hydraulic basal chamber 314 and the hydraulic pump chamber 318 during use is approximately 46:1. In one embodiment the hydraulic basal chamber 314 operates at a pressure between approximately 20 psi and between 70 psi. In one embodiment, the hydraulic basal chamber 314 operates at a pressure of approximately 46.8 psi. In one embodiment, the hydraulic pump chamber 318 operates at a pressure of approximately 0.5 psi to approximately 5 psi. In one embodiment, the hydraulic pump chamber 318 operates at a pressure of approximately 1.2 psi.

The flow restrictor 336 is dimensionally adapted to control the rate of fluid flow there through. In one embodiment, the flow restrictor 336 has a diameter of approximately 1-1000 μm. It should be understood that all ranges provided herein encompass both the beginning and end points of the range (e.g., includes 1 and 1000 μm in a range of from about 1 to about 1000 μm), as well as all values in between. Whatever the shape of the flow restrictor 336, the cross sectional area and the length of the opening will be sized to achieve the flow rate desired. For example, the flow restrictor 336 can be about one-ten thousandths of an inch (or 2-3 μm) in diameter. Depending on use, the flow restrictor 336 size can be anything, including but not limited to a diameter between 200 nm-500 nm, or 500 nm-1000 nm, or 1-2 μm, or 5-10 μm, or 10-1000 μm. In one embodiment, the outer diameter of the flow restrictor 336 is approximately 0.026 inches and the inner diameter of the flow restrictor 336 is one of approximately 0.00758 inches, 0.00708 inches and 0.00638 inches. In one embodiment, the length and outer diameter of the flow restrictor 336 remains constant from device to device based on the size of the manifold 226 and the inner diameter of the flow restrictor 336 can be altered to achieve the desired flow rate. Other sizes and dimensions of the flow restrictor 336 can be selected, and the size and dimension selected will depend upon the application at hand and, in particular, the viscosity of the hydraulic fluid and the force applied by the basal actuator 320. In one embodiment, the flow restrictor 336 is comprised of topaz. Having a flow restrictor 336 comprised of topaz can help to ensure that the flow restrictor 336 has a substantially accurate and constant cross sectional size and shape. Those of skill in the art will understand that any suitable flow restrictor 336 can be employed, and that the size and the shape of the flow restrictor 336 can vary to achieve the desired flow rate of the fluid being mediated under the expected conditions, including temperature and ambient pressure. The flow restrictor 336 need not be circular in cross sectional shape, and can be an oval, a square, a rectangle, a triangle, a polygon, or irregular in shape. The size and shape of the flow restrictor 336 can be determined empirically by testing the fluid flow of selected fluids at conditions of interest.

Figures 4A, 4B:
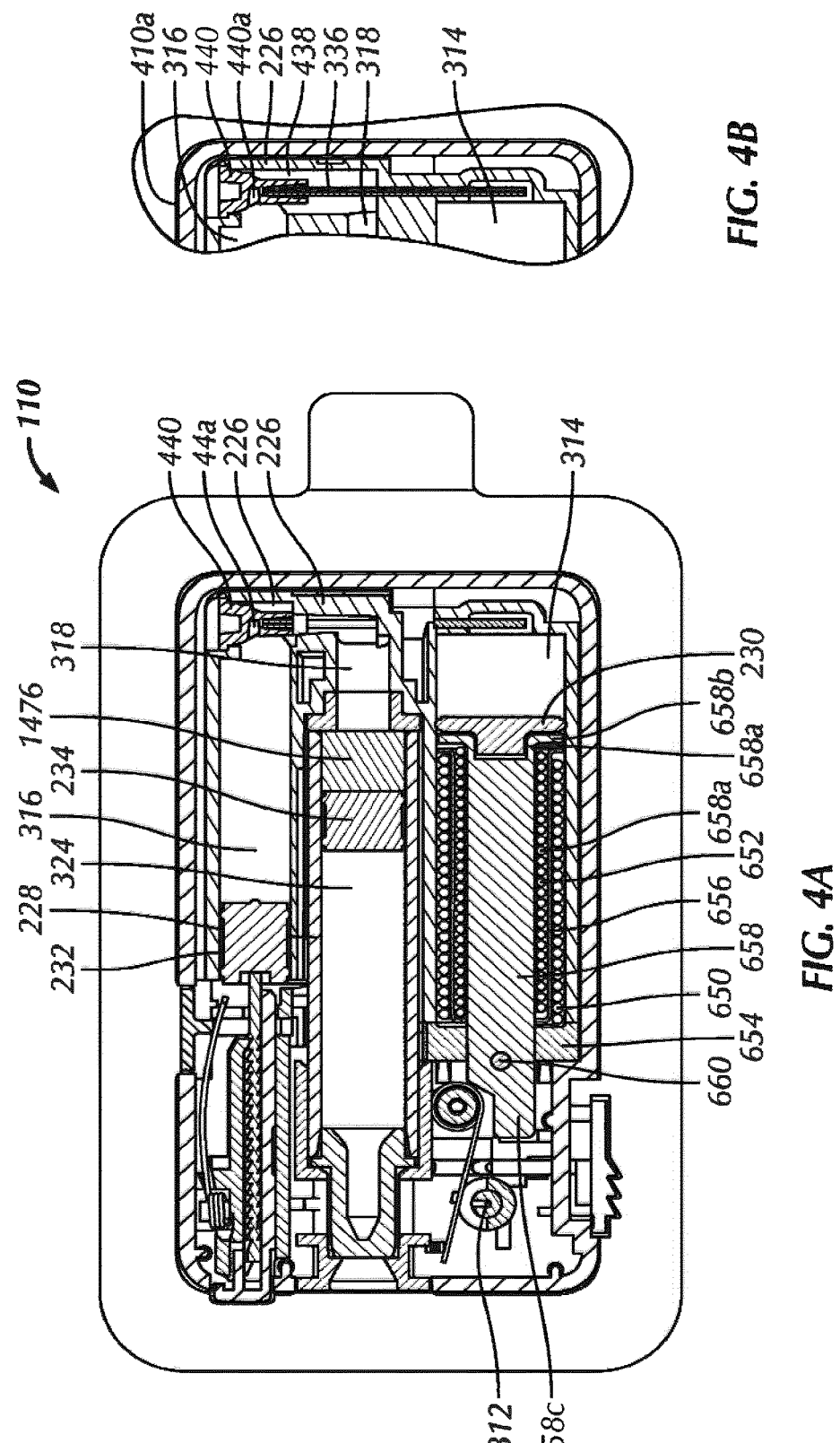
FIG. 4A is a top cross sectional view of the fluid delivery device shown in FIG. 1 taken along line 4A-4A of FIG. 1.
FIG. 4B is a top partial cross sectional view of the fluid delivery device shown in FIG. 1 taken along a length of a flow restrictor.

Referring to FIG. 4B, in one embodiment, the flow restrictor 336 extends through a side 410a of the fluid delivery device 110. In one embodiment, the flow restrictor 336 extends through the hydraulic bolus chamber 316 such that the hydraulic bolus chamber 316 is in fluid communication with the hydraulic basal chamber 314 through the flow restrictor 336 and the hydraulic basal and bolus chambers 314, 316 are both in fluid communication with the hydraulic pump chamber 318 through a nonrestrictive fluid passageway 438. In an alternative embodiment, the fluid passageway 438 is restrictive in order to retard the delivery rate of the bolus dose rather than having the delivery rate be nearly equal to the rate of movement of the bolus actuator 322.

With continued reference to FIG. 4B, in one embodiment, the flow restrictor 336 includes a guide plug 440. In one embodiment, the guide plug 440 is sealed with the manifold 226 and positions the flow restrictor 336 within the fluid passageway 438. In one embodiment, the guide plug 440 includes an opening 440a for fluidly coupling the flow restrictor 336 and the hydraulic bolus chamber 316. The flow restrictor 336 can be secured to the manifold 226 by an epoxy. In one embodiment, the guide plug 440 and the flow restrictor 336 are comprised of generally translucent materials such that the flow restrictor 336 can be fixed to the manifold 226 by a UV curable resin after inserting the flow restrictor 336 and the guide plug 440 within the manifold 226.

When the fluid delivery device 110 is activated, the basal actuator 320 acts on the hydraulic fluid, increasing the pressure within the hydraulic basal chamber 314. As a result of this pressure increase, the hydraulic liquid within the hydraulic basal chamber 314 begins to flow through the flow restrictor 336 into the hydraulic bolus chamber 316. In one embodiment, the bolus actuator 320 prevents expansion of the hydraulic bolus chamber 316 and the hydraulic fluid from the hydraulic basal chamber 314 flows through the fluid passageway 438 and into the hydraulic pump chamber 318 where the hydraulic fluid displaces the third moveable barrier 234 causing the fluid within the fluid reservoir 324 to exit the fluid delivery device 110 at a sustained basal rate. In one embodiment, the basal rate is predetermined or preset by the manufacturer. Embodiments of the fluid delivery device 110 can be used to continuously deliver a fluid over a range of time such as but limited to 1 min, 1 hr, 6 hrs, 12 hrs, 1 day, 3 days, 5 days, 10 days, one month, etc. In certain embodiments, the fluid is expelled from the fluid delivery device 110 at a basal rate selected from but not limited to: about 0.1 μl to about 10 μl per hour, about 10 to about 100 μl per hour, about 100 μl per hour to about 1 ml per hour, about 1 ml to about 100 ml per hour, or about 100 ml to about 200 ml per hour. The rate and delivery period selected will depend upon the application at hand, and those of skill in the art will be able to determine the proper dosage rate for a given application. In that respect, in accordance with one embodiment, the basal rate may be between 10 μl/hour to 5 ml/hr. In accordance with some particular embodiments, the basal rate may be at least 10 μl/hour, 20 μl/hour, 25 μl/hour, or 50 μl/hour. Similarly, alongside or instead of any such lower bound basal rates, in accordance with some particular embodiments, the basal rate may equally be no more than 5 ml/hr, 3 ml/hr, 2 ml/hr, 1 ml/hr and/or 500 μl/hour.

Referring to FIG. 3, embodiments of the fluid delivery device 110 can be connected to an infusion set or needle 312 through a connection point at the distal end 324a of the fluid reservoir 324. In alternative embodiments, the needle 312 can be located on the side wall of fluid reservoir 324. The needle 312 can be substituted with any delivery device such as a lumen, a needle set, a catheter-cannula set or a microneedle or microneedle array attached by means of one or more lumens.

In one embodiment, basal flow rate is preset at the time of manufacture based on the selection of the flow restrictor 336 in combination with the viscosity of the hydraulic fluid and the force supplied on the hydraulic basal chamber 314. Alternatively, the length and/or diameter of the flow restrictor 336 can be adjusted on demand to alter the basal flow rate. In other embodiments, the flow restrictor 336 can be adjustable in size, as by means of an adjustable iris-type aperture or telescoping restrictor passage miniature valve or paired gating slits (not shown). In an alternate embodiment, an electrical motor or piezoelectric device (not shown) can be used to open or close the aperture, thus affecting the rate at which hydraulic fluid flows into pump chamber and displaces the third moveable barrier 234.

The hydraulic fluid can be any non-compressible, flowable material such as gel or a collection of miniature solid beads. In one embodiment, the hydraulic fluid is an ultra pure, bio-inert material. In one embodiment the hydraulic fluid is silicon oil. Useful viscosity of the hydraulic fluid is limited at its upper bound by the size of the flow restrictor 336. At its lower bound, the hydraulic fluid must be viscous enough that the flow of the hydraulic fluid can remain highly regulated by the combination of the pressure from the basal actuator 320 and the size of the flow restrictor 336 under a wide range of environmental conditions, especially in the presence of low atmospheric pressure and/or high ambient temperature (where viscosity tends to decrease).

As used herein, "high viscosity" means the working hydraulic fluid has a viscosity grade of at least about ISO VG 20, or at least about ISO VG 32, or at least about ISO VG 50, or at least about ISO VG 150, or at least about ISO VG 450, or at least about ISO VG 1000, or at least about ISO VG 1500 or more. In one embodiment the hydraulic fluid is very high viscosity fluid. As used herein, "very high viscosity" means the working hydraulic fluid has a viscosity of from about 80,000 to about 180,000 cPs. In one embodiment the hydraulic fluid is ultra high viscosity fluid (e.g., from about 180,000 to about 200 cPs). In one embodiment, the hydraulic fluid has a viscosity of 100,000 centiStokes.

In one embodiment, since viscosity varies inversely with temperature it is important to keep the hydraulic fluid at a generally constant temperature. The fluid delivery device 110 is worn on the user's body for the duration of administration of the fluid. The fluid delivery device 110 can be dimensionally adapted to attach to a user's body via an adhesive patch 542 (see FIG. 5) as described further below. Accordingly, the fluid delivery device 110 will be exposed to a range of environmental conditions commensurate with the patient's lifestyle. Without appropriate control of the variation in temperature of the hydraulic fluid, higher environmental temperatures can cause a reduction in viscosity, resulting in an increase in fluid flow and lower environmental temperatures can cause an increase in viscosity, resulting in a decrease in fluid flow. In one embodiment, the hydraulic fluid is brought to a generally constant temperature corresponding to the temperature of the user's skin. Thus, in some embodiments, the configuration of the fluid delivery device 110 reduces the effect of environmental temperature on the temperature of hydraulic fluid in the device. In one embodiment, because the temperature of the user's skin is likely higher than the storage temperature of the hydraulic fluid, the initial fluid delivery rate is ramped up to the sustained basal delivery rate.

Figure 5:
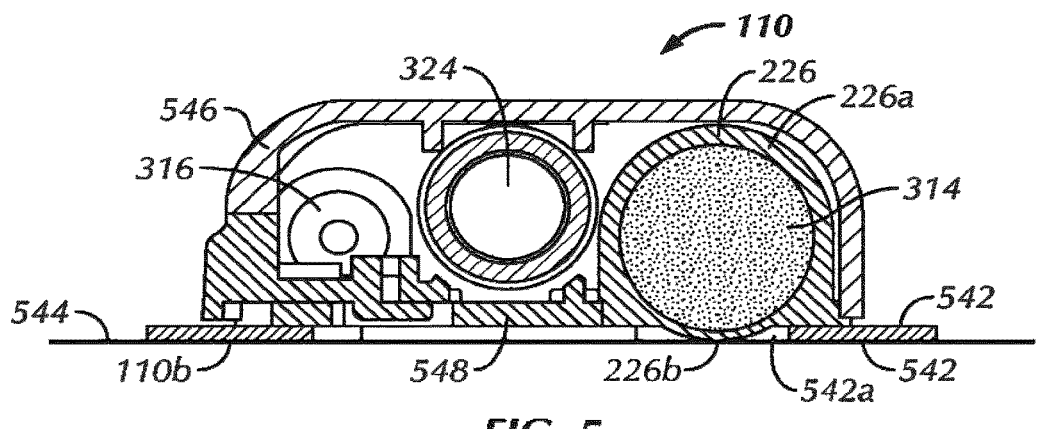
FIG. 5 is a front cross sectional view of the fluid delivery device shown in FIG. 1 taken along line 5-5 of FIG. 1.

Referring to FIG. 5, the fluid delivery device 110 can comprise a conductive thermal couple between the hydraulic fluid in the fluid delivery device and the body of the wearer. The thermal couple utilizes the consistent temperature of the body to regulate or moderate the temperature of the hydraulic fluid which might otherwise be subject to wide variation as a result of environmental temperature changes. This modulation reduces variation in the viscosity of the hydraulic fluid, thereby reducing undesired variation in the flow or delivery of the fluid caused by changes in ambient temperature. Similarly, the fluid delivery device can comprise a thermal couple between the pharmaceutical composition in the fluid reservoir and the body of the wearer. The thermal couple utilizes the consistent temperature of the body to regulate or moderate the temperature of the pharmaceutical composition which might otherwise be subject to wide variation as a result of environmental temperature changes.

In one embodiment, a thermally conductive path is provided between a hydraulic basal chamber 314 and the skin. The fluid delivery device can have an attachment surface 542a having a first thermal conductance configured to engage with a skin surface 544. In one embodiment, the manifold 226 housing the hydraulic basal chamber 314 has an outer wall 226a. In one embodiment, the outer wall 226a has a portion 226b proximate the attachment surface 542a having a second thermal conductance; the second thermal conductance being greater than the first thermal conductance of the attachment surface 542a. The portion 226b of the manifold proximate the attachment surface 542a can be in direct contact with the skin surface 544 to allow for the hydraulic fluid within the hydraulic basal chamber to be kept at a substantially constant temperature corresponding to the temperature of the skin surface 544. In one embodiment, the attachment surface 542a is integral with an outer housing

546. In one embodiment, the attachment surface 542a is integral with a base 548 that is attached to the housing 546 (see FIG. 2). As used herein, the base 548 can be considered to be part of the housing 546.

In another embodiment, thermal insulation is provided around the remaining surfaces of the hydraulic basal chamber 314 that are exposed, directly or indirectly such as through the housing 546 to the outside environment. The thermal insulation can be any thermally conductive material and or an air space as shown. In a preferred embodiment, a thermally conductive path is coupled with thermal insulation against the outside environment (FIG. 5). In order to optimize the conductive coupling between the skin surface 544 body and the hydraulic fluid, the hydraulic basal chamber 314 can be positioned in direct contact with the body of the wearer. The fluid delivery device 110 can also be worn on the belly of the user and covered with clothing to help further reduce the impact of changes in the ambient temperature.

As shown in FIG. 5, the portion 226b of the manifold 226 housing the hydraulic basal chamber 314 can be proud of the surrounding surface of the base 548. In one embodiment, the portion 226b of the manifold 226 extending from the base 548 is generally tangent with attachment surface 542a of the adhesive patch 542 such the entire bottom surface 110b of the fluid delivery device 110 is substantially planar. If present, the adhesive patch or pad 542 that affixes the fluid delivery device 110 to the skin surface 544 is preferably relieved in this area, relief area 542a to further assure contact between the outer reservoir wall and the skin (see also FIG. 2). The adhesive patch 542 can partially extend below or over the manifold 226 to prevent the side of the manifold from extending through relief area 542a upon movement of adhesive patch extending outwardly from the fluid delivery device 110. In one embodiment, the outer wall of the manifold 226 can be thinned (as shown) or the housing or other materials can be relieved in the area which contacts the skin surface 544 proximate the hydraulic basal chamber 314 in order to reduce the mass of material separating the hydraulic fluid and the user to increase the thermal couple between the body and the hydraulic fluid.

In order to further reduce the influence of the outside environmental temperature on the temperature of the hydraulic fluid, one or more additional features can be incorporated into the device to insulate and isolate the hydraulic fluid from the outside environment. The hydraulic basal chamber 314 can be a separate or isolated component from the remainder of the manifold (not shown). In one embodiment, the manifold 226 and the housing 546 can be separated by an open air gap in the areas that face toward the outside environment. To further isolate the hydraulic liquid, the air gap between the hydraulic basal chamber and the housing 546 can be divided into separate air pockets to further decouple or insulate the air within this gap. In one embodiment, the fluid reservoir 324 is thermally isolated from the skin surface 544. In one embodiment, the air gap within the housing 546 substantially surrounds the fluid reservoir 324 to keep the fluid at a cooler temperature than the skin surface 544.

In one embodiment, one or more of the above configurations permits the fluid delivery device 110 to operate within a temperature range of 40° F. (5° C.) to 104° F. (40° C.). In the absence of a thermal coupling and if the hydraulic liquid were exposed to this full temperature range during operation, the amount of resulting flow variation as a result of the change in the viscosity of the hydraulic liquid (typically on the order of a 1% shift in viscosity per a 1° F. shift in temperature) could introduce too large a variation in the flow of the hydraulic fluid through the flow restrictor 336 yielding unacceptable drug delivery performance. In one embodiment, the improved temperature regulation features of the fluid delivery device 110 result in less than a 1% shift in viscosity per a 1° F. shift in ambient temperature. For example, the features can result in a change of about 0.15%, 0.10% or 0.05% shift in viscosity per 1° F. shift in temperature. In one embodiment, only an approximate 6° F. difference exists between the skin surface 544 and the hydraulic liquid at the low temperature limit and little to no difference exists between the two measurements at the high temperature limit. As a result of this efficient couple between the skin surface 544 and the hydraulic liquid, a change in temperature of less than 10° F. can be observed in the hydraulic liquid over a 65° F. change in ambient (environmental) temperature.

Figure 6A:
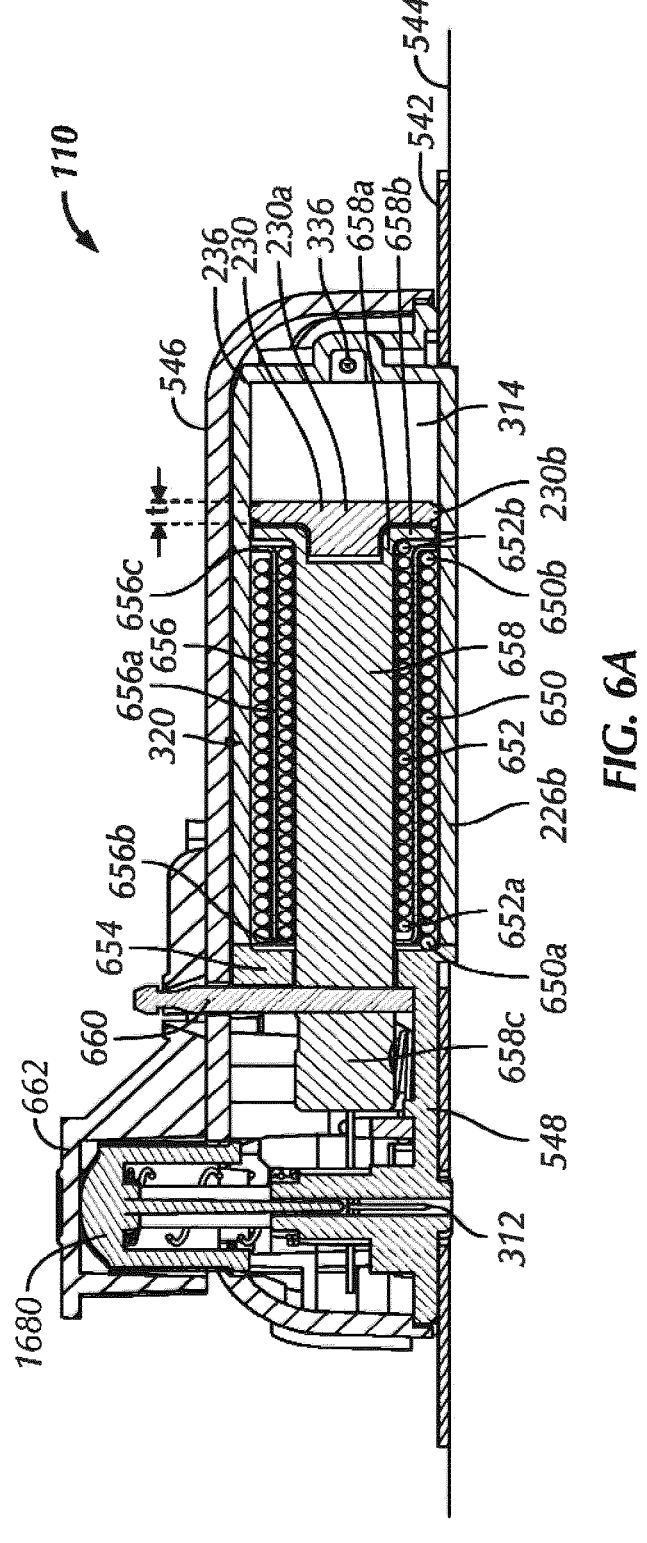
FIG. 6A is a side cross sectional view of a basal hydraulic chamber and biasing members of the fluid delivery device shown in FIG. 1 taken along line 6A-6A of FIG. 1 show in an initial position.
Figures 6B, 6C:
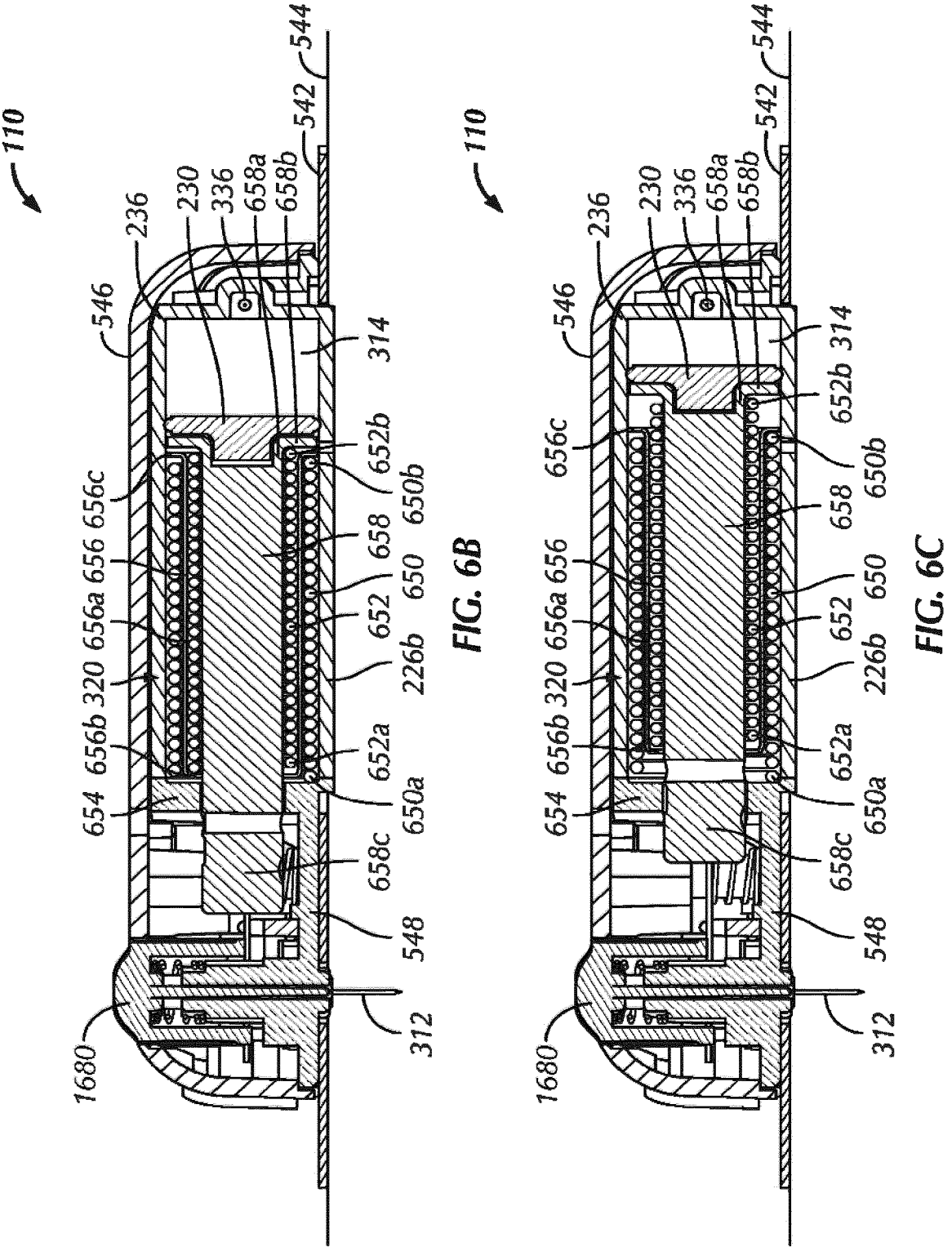
FIG. 6B is the side cross sectional view of FIG. 6A shown in the engaged position.
FIG. 6C is the side cross sectional view of FIG. 6A shown in the engaged position after a length of time in use.

Referring to FIGS. 6A-6C, in one embodiment, the basal actuator 320 exerts a force on the hydraulic basal chamber 314 to pressurize the hydraulic fluid. The basal actuator 320 can be any device that applies a force on the hydraulic basal chamber 314 such as, but not limited to a peristaltic actuator, miniaturized bellows crank, or paired rollers bearing on hydraulic basal chamber 314, ratchet or stepper motor driven units that compress plates or other structures bearing on the hydraulic basal chamber 314, electrically driven or piezo-electric mechanisms, expanding gas volume, thermal energy, or any other device or process capable apply a pressure, either directly or indirectly, to the fluid being delivered. In one embodiment, the basal actuator 320 is open loop such that no electronics are required and the fluid delivery device 110 can be purely mechanical.

In one embodiment, the basal actuator 320 is comprised of one or more biasing members such as a first biasing member 650 and a second biasing member 652. In one embodiment, the one first and second biasing members 650, 652 are springs. In one embodiment, the first and second biasing members 650, 652 are helical compression springs. The force exerted by a spring in a compressed state at the start of travel is greater than the force exerted by the spring in a less compressed state toward the end of travel. The resulting force differential can impact the flow of hydraulic fluid within the fluid delivery device 110 and thus impact the flow of the fluid being delivered.

In one embodiment, the difference in the force exerted by the first and second biasing members 650, 652 between the initial compressed state and the less compressed state is reduced, thus reducing the amount of possible variation in the device's ability to achieve a sustained fluid delivery rate. In one embodiment, the force differential between the compressed and less compressed state is minimized by reducing the spring rate (force/deflection) of the spring. The spring rate can be reduced by increasing the length of the spring. In one embodiment, in order to keep the fluid deliver device 110 as compact in size as possible and prevent the basal actuator 320 from having a decreased forced from beginning to end, multiple, coaxial stacked biasing members are used. In an alternative embodiment, the second biasing member 652 is coupled to the first biasing member 650 in parallel. However, overlapping the first and second biasing members 650, 652 further reduces the size of the fluid delivery device 110. In one embodiment, the cross sectional area of the hydraulic basal chamber 314 is larger than the cross sectional area of the fluid reservoir 324 to move the third moveable barrier 234 a greater axial distance than the axial distance traveled by the first moveable barrier 230 (see e.g. FIG. 4A). Reducing the spring force attenuation that occurs over the total travel of the spring (stroke) during operation and maintaining a more constant spring force on the hydraulic fluid produces a more consistent flow of fluid from the device.

Referring to FIG. 6A, in one embodiment, the second biasing member 652 is coupled to the first biasing member 650 in series and at least partially overlaps the first biasing member 650. In one embodiment, the first biasing member 650 is co-axial with the second biasing member 652. A co-axial arrangement of the first biasing member 650 and the second biasing member 652 can be preferred over a parallel arrangement. In one embodiment, a proximal end 650*a* of the first biasing member 650 is coupled to the housing 546. In one embodiment, the proximal end 650*a* abuts against a stop 654 extending from the base 548 (see also FIG. 2). In one embodiment, a sleeve 656 couples a distal end 650*b* of the first biasing member with a proximal end 652*a* of the second biasing member 652, the sleeve 656 having a length generally equal to the length of overlap between the first and second biasing members 650, 652. In one embodiment, the sleeve 656 has a body 656*a*, a first flanged end 656*c* and a second flanged end 656*b*. The first flanged end 656*c* can extend radially outwardly from the body 656*a* of the sleeve 656 to engage the distal end 650*b* of the first biasing member 650. The second flanged end 656*b* of the sleeve 656 can extend radially inwardly from the body 656*a* of the sleeve 656 to engage a proximal end 652*a* of the second biasing member 652. The body 656*a* of the sleeve 656 can be generally hollow to allow the second biasing member 652 to extend through the sleeve 656 and engage the second flanged end 656*b*. In one embodiment, the first and second biasing members 650, 652 have substantially equal spring rates such that the sleeve 656 "floats" between the first and second biasing members 650, 652 as they both expand. If one biasing member were stronger than the other, the stronger biasing member can dominate, preventing the other biasing member from expanding and negating the benefit of the multi-biasing member configuration. In one embodiment, the difference in spring rate between the first and second biasing members 650, 652 is no greater than approximately 10%. In one embodiment, the difference in spring rate between the first and second biasing members 650, 652 is no greater than approximately 3%.

The basal actuator 320 can include a plunger 658 extending through the first and second biasing members 650, 652. In one embodiment, the distal end 658*a* of the plunger 658 has a radially outwardly extending flange 658*b*. The flange 658*b* of the plunger 658 can engage the first moveable barrier 230 and the distal end 652*b* of the second biasing member 652. A proximal end 658*c* of the plunger 658 can be releasably coupled with the stop 654. The plunger 658 can extend through the stop 654 and be releasably coupled to the housing with a pin 660. In one embodiment, the pin 660 extends through the housing 546 and at least partially through the plunger 658 and abuts against the stop 654 such that the pin 660 prevents the plunger 658 from extending further into the hydraulic basal chamber 314 due to the force of the first and second biasing members 650, 652 and can be removed from outside of the housing 546. In one embodiment, the pin 660 is tapered to facilitate easier removal of the pin 660. The pin 660 can be coupled with a button cover 662 such that removal of the button cover 662 releases the plunger 658 in one step by the user as described further below. FIGS. 6A-6C illustrate the basal actuator 320 in the initial position (FIG. 6A), immediately after removing the pin 660 to activate or initiate the basal actuator 320 (FIG.

6B) and the basal actuator 320 in use after a period of delivering the fluid (FIG. 6C).

Figure 7:
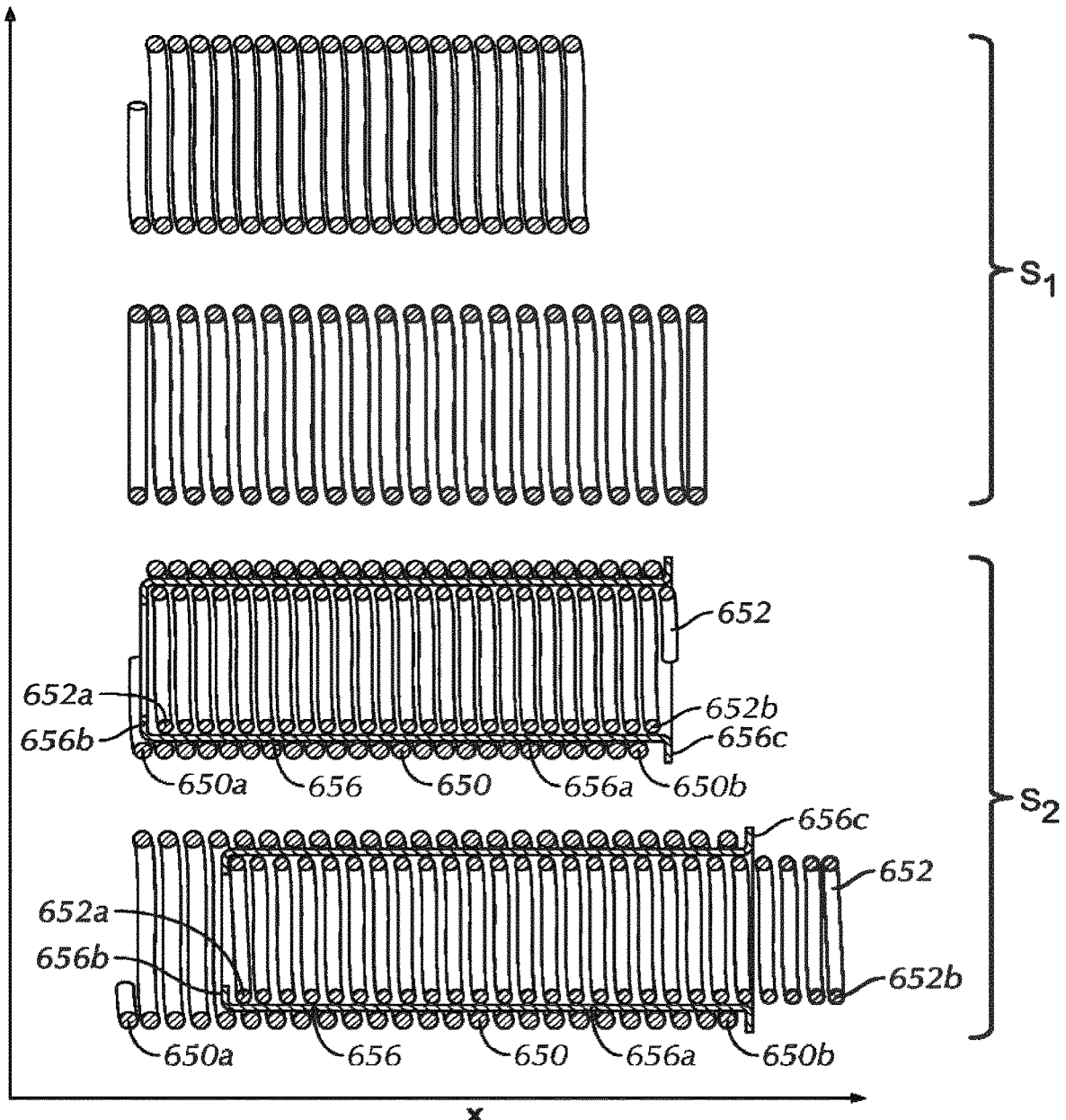
FIG. 7 includes side cross sectional views of first and second biasing members of the fluid delivery Device shown in FIG. 1 in comparison with side cross sectional views of a conventional single biasing member.

Referring to FIG. 7, in one embodiment the configuration of the first and second biasing members 650, 652 reduces the drop in force applied to the hydraulic basal chamber 314 due to the expansion of the first and second biasing members 650, 652. For example, a single compression spring $S_1$ compressed to a height of 0.75 inches will apply a force of 5.7 pounds. When this single spring $S_1$ extends to a height of 0.935 inches, the force applied drops to 5.34 pounds. This 6.3% drop in force would result in a proportional drop in hydraulic flow rate and in turn basal delivery rate of fluid from the fluid delivery device 110. To increase the volume of the fluid displaced by the fluid delivery device 110 without increasing the drop in force, the basal actuator 320 would need to be lengthened proportional to the volume increase required. In one exemplary embodiment, a dual overlapped spring configuration $S_2$ compressed to a height of 0.945 inches will apply a force of 5.7 pounds. When the dual springs $S_2$ extend to a height of 1.283 inches, the force drops to 5.34 pounds. This 6.3% drop in force would be proportional to the drop in flow rate; however, unlike the single spring $S_1$ the displacement volume is 83% greater while the length of the spring assembly is only 25% greater. The dual spring assembly $S_2$ provides an additional 83% increase in spring extension for a given loss of 0.36 pounds in spring force. This provides additional basal capacity without increasing losses due to spring extension. Conversely, the dual spring $S_2$ could be used to deliver an equivalent volume (as compared with a single spring embodiment $S_1$), with far less losses due to spring extension over an equivalent extension length (approximately a 45% decrease in the force drop over an equivalent extension length). It is understood that a dual spring arrangement as shown is but one embodiment, and that three or more springs can also be utilized.

In one embodiment, the basal actuator 320 has less than a 10% drop in force applied to the hydraulic basal chamber 314 from beginning of delivery to end of delivery. In one embodiment, the basal actuator 320 has less than an 8% drop in force applied to the hydraulic basal chamber 314 from beginning of delivery to end of delivery. In one embodiment, the basal actuator 320 has less than a 6% drop in force applied to the hydraulic basal chamber 314 from beginning of delivery to end of delivery. In one embodiment, the basal actuator 320 has less than a 5% drop in force applied to the hydraulic basal chamber 314 from beginning of delivery to end of delivery. In one embodiment, the basal actuator 320 has less than a 4% drop in force applied to the hydraulic basal chamber 314 from beginning of delivery to end of delivery. In one embodiment, the basal actuator 320 has less than a 3% drop in force applied to the hydraulic basal chamber 314 from beginning of delivery to end of delivery.

In one embodiment, the basal actuator 320 has less than a predetermined drop in force applied to the hydraulic basal chamber 314 from beginning of delivery to end of delivery as described above and has a length less than approximately 2 inches. In one embodiment, the basal actuator 320 has less than a predetermined drop in force applied to the hydraulic basal chamber 314 from beginning of delivery to end of delivery as described above and has a length less than approximately 1.5 inches. In one embodiment, the basal actuator 320 has less than a predetermined drop in force applied to the hydraulic basal chamber 314 from beginning of delivery to end of delivery as described above and has a length less than approximately 1 inch. In one embodiment, the basal actuator 320 has less than a predetermined drop in force applied to the hydraulic basal chamber 314 from beginning of delivery to end of delivery as described above and has a length less than approximately 0.8 inches.

Referring to FIG. 4A, in one embodiment, delivery consistency of the fluid is improved by reducing the amount of variation in force required to displace the third moveable barrier 234. In preferred embodiments, the force required to displace the third moveable barrier 234 is reduced or controlled by limiting or controlling one or more of the contact area, contact force and coefficient of friction between the moveable barriers 230, 232, 234 and their chamber walls and the compressibility of the hydraulic fluid and the first moveable barrier 230.

Referring to FIG. 6A, the first moveable barrier 230 can have a thickness t that is the minimum thickness to create a seal. In one embodiment, the first moveable barrier has a thickness t of approximately 0.05 inches. In one embodiment, the first moveable barrier 230 has a projection 230a that extends into the distal end 658a of the plunger 658. In one embodiment, the first moveable barrier 230 includes a rounded outer periphery 230b for contacting the inside surface of the manifold 226. In one embodiment, the outer periphery 230b of the first moveable barrier 230 is integral with the remainder of the first moveable barrier 230. In one embodiment, the first moveable barrier 230 is comprised of Bromo-Butyl Rubber. In one embodiment, the first moveable barrier 230 has a durometer of 40 shore A.

Figure 8:
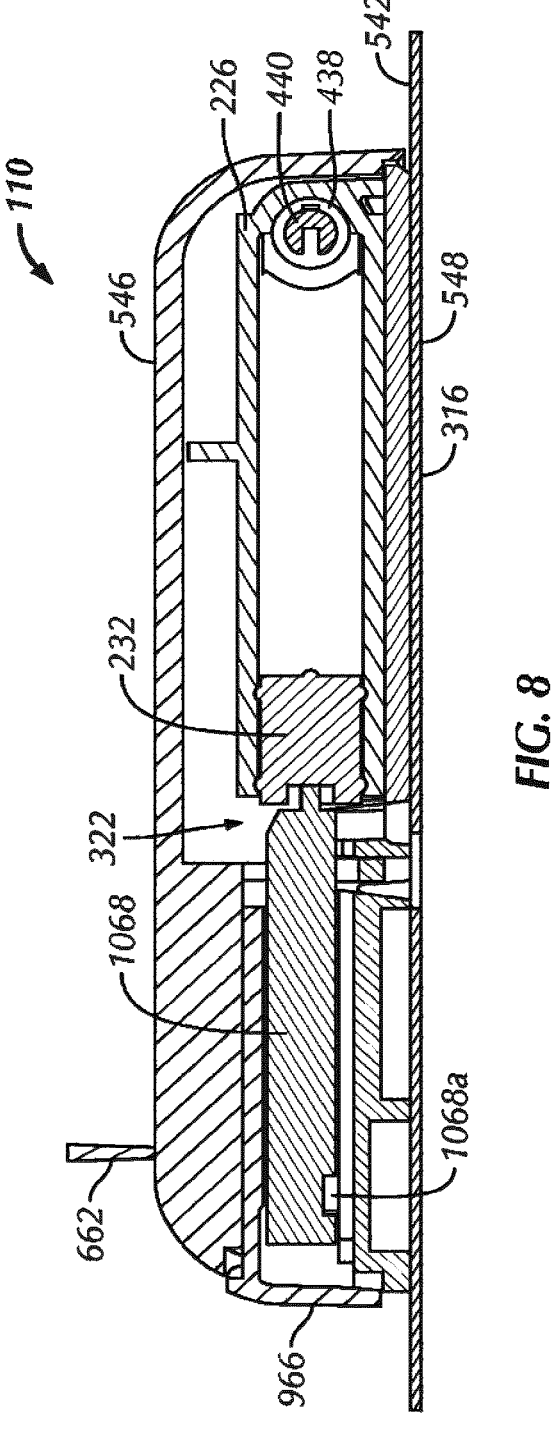
FIG. 8 is a side cross sectional view of a bolus button and a bolus hydraulic chamber of the fluid delivery device shown in FIG. 1 taken along line 8-8 in FIG. 1.
Figure 9A:
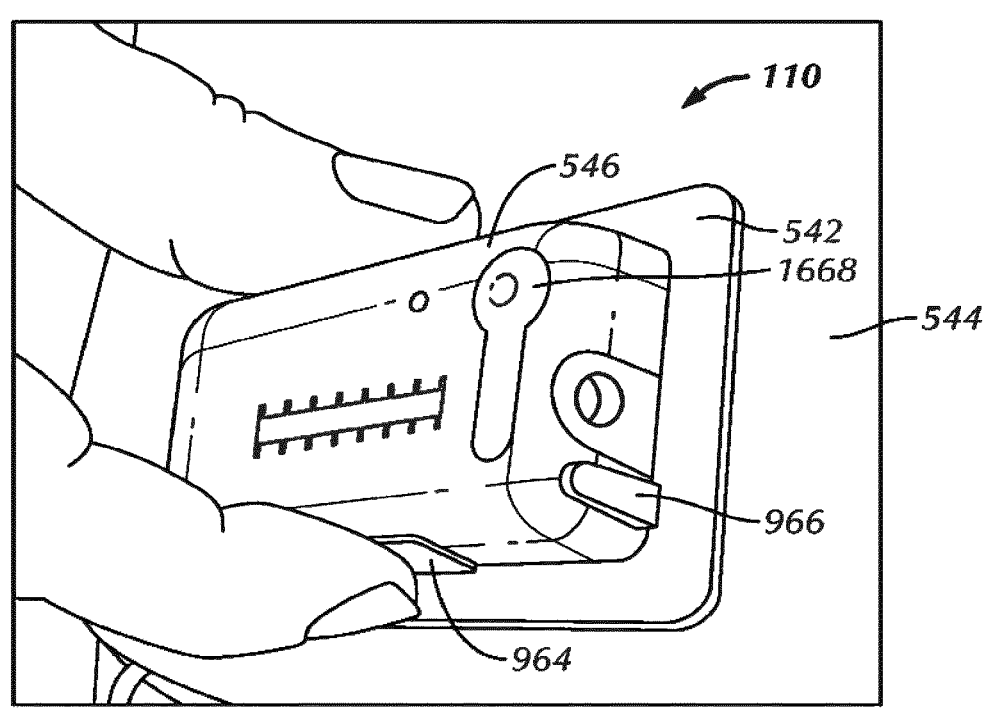
FIG. 9A is an illustrative perspective view of the fluid delivery device shown in FIG. 1 in the engaged position on a user and showing the user unlocking a bolus button.
Figure 9B:
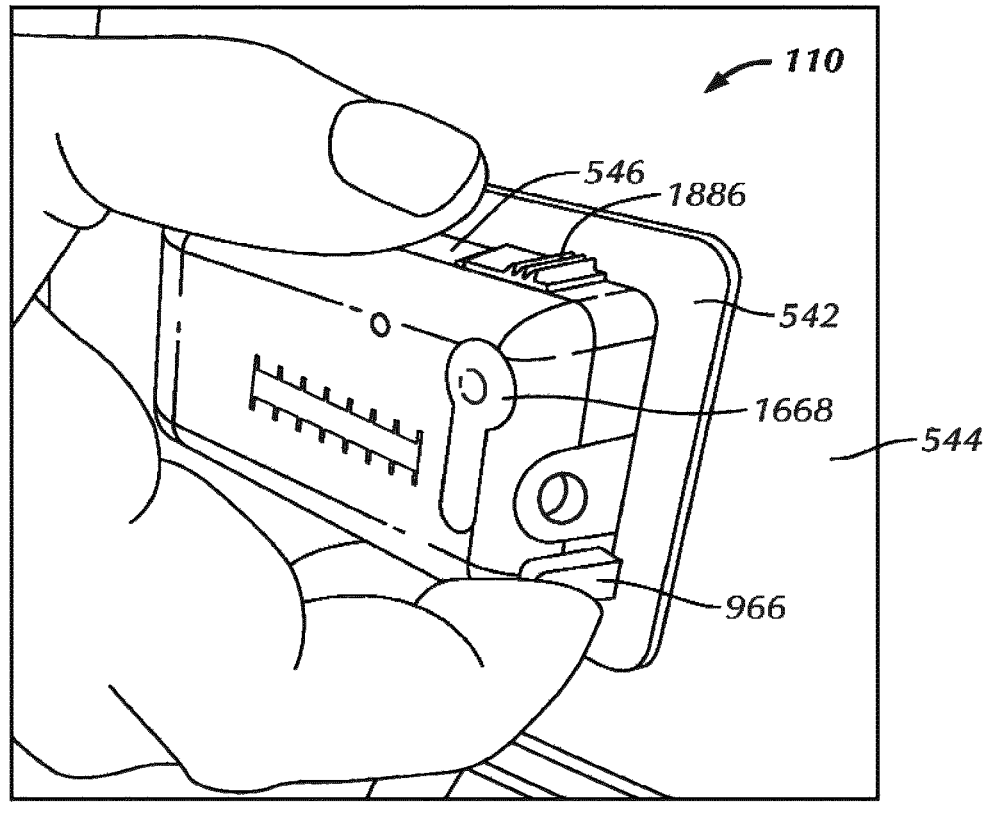
FIG. 9B is an illustrative perspective view of the fluid delivery device shown in FIG. 1 in the engaged position on the user and showing the user pressing the bolus button.

Referring to FIGS. 8-9B, in one embodiment, the fluid delivery device 110 is capable of dispensing fluid continuously or near continuously at a basal rate, as well as dispensing a supplementary amount of fluid or bolus on demand or under patient control. The fluid delivery device 110 can allow for the user to deliver multiple discrete bolus amounts without the user having to look at the fluid delivery device 110 or set the bolus amount for delivery under and through the user's shirt (not shown). Each bolus dose can require two distinct motions to deliver the bolus dose. In one embodiment, a multiple button sequence to be performed by the user to improve deliberate and correct bolus dosing. In a preferred embodiment, the bolus delivery is operated by a cyclic (i.e., common, consistent, routine) mechanical system in which the user executes the same action one or multiple times to achieve one or multiple bolus doses per cycle.

The number of bolus increments as well as the volume or dose per bolus increment can be preset at the time of manufacture based on the selection of component parameters as described further below. The fluid delivery device 110 can be preconfigured in a number of ways (fast/slow basal rate, large/small bolus volume, many/few bolus increments) to facilitate a variety of therapeutic needs.

Referring to FIGS. 9A and 9B, in one embodiment, each bolus delivery is individually and deliberately activated by the user. For example, in one embodiment each bolus delivery requires multiple (two or more) independent actions by the user, such as button actuations (via a bolus release button 964 and a bolus button 966), to insure that each bolus increment (dose) is delivered by deliberate and intentional means and not accidentally, incorrectly, or inadvertently delivered. The bolus button 966 and bolus release button 964 can be located on different sides of the fluid delivery device 110. The user can slide his or her finger along a first side of the fluid delivery device 110 until the bolus release button 964 is depressed and continue sliding their finger up a second side of the fluid delivery device 110 until the bolus button 966 is depressed. The user can slide their finger along the sides of the fluid delivery device 110 in order to find the bolus and bolus release buttons 964, 966 and the direction of movement of the user's finger or orientation of side of the fluid delivery device 110 and/or the configuration of the bolus and bolus release buttons 964, 966 help to indicate to the user which button is being depressed without having to look at the fluid delivery device 110. In one embodiment, the bolus button 966 and the bolus release button 964 are on two different sides of the fluid delivery device 110. In one embodiment, the different sides of the fluid delivery device 110 have different length to facilitate tactile feedback when administering a bolus dose, allowing operation without direct line of sight (e.g., operating the fluid delivery device 110 under one or more articles of clothing). In one embodiment, the bolus button 966 and the bolus release button 964 are located on the same side of the fluid delivery device 110. In addition, an audible "click" feedback provided by depression of either button 964, 966 can further facilitate predictable operation. In one embodiment, the bolus and bolus release buttons 964, 966 each have a distinct sound.

As illustrated in FIGS. 9A and 9B, the bolus release button 964 is depressed (FIG. 9A) prior to depressing the bolus button 966 (FIG. 9B). In one embodiment, the bolus release button 964 enables the bolus actuator 322 for actuation by the bolus button 966 such that the bolus button 966 cannot be activated absent enablement by the bolus release button 964. When the user is ready to deliver a bolus dose of fluid, he or she depresses the bolus release button 964. When depressed, the bolus release button 964 enables the bolus button 966 and after depressing the bolus button 966 causes the bolus actuator 322 to advance one bolus increment.

In some embodiments, the fluid delivery device 110 delivers a discrete dosage unit per actuation; the appropriate dosage unit will vary depending on the fluid to be delivered. At the same time, the fluid delivery device 110 can delivering an additional amount (e.g., 20, 30, 40, etc. units) at the basal rate over the entire delivery period. The total fluid capacity of the fluid delivery device 110 is the sum of the basal and bolus capacities. In some embodiments, the fluid delivery device 110 has a total fluid capacity of 56, 66 or 76 units. In other embodiments, the fluid delivery device has a total fluid capacity of about 1200, 1500, or 2000 units.

Figure 10A:
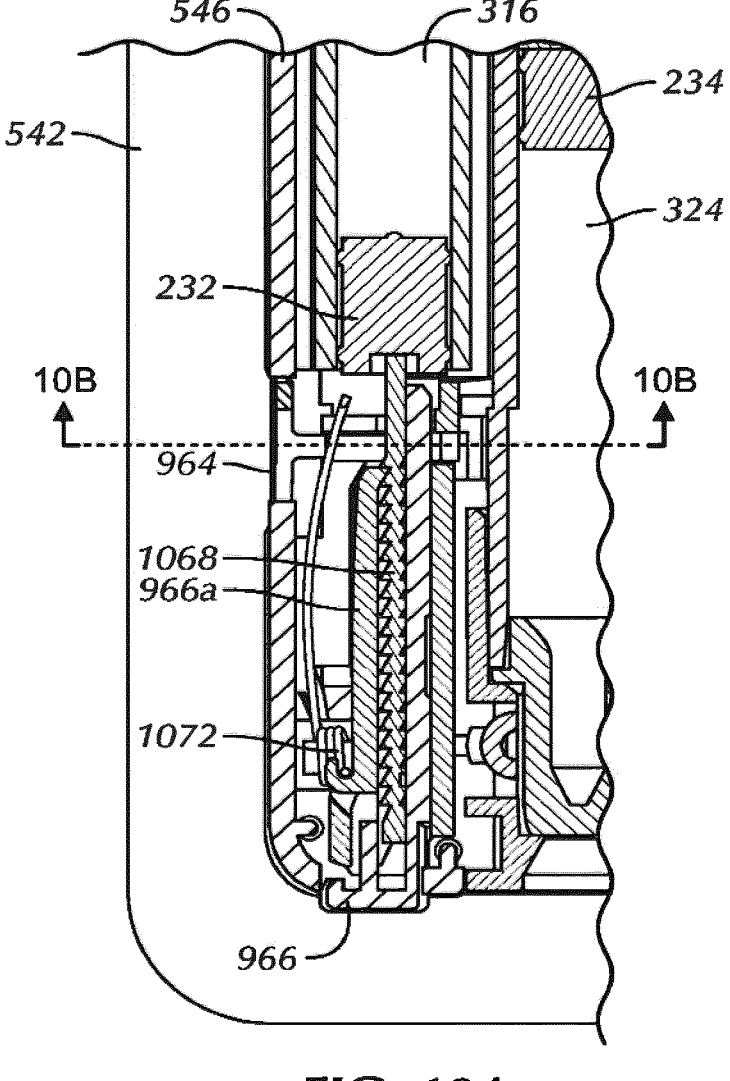
FIG. 10A is a partial, top, cross sectional view of the fluid delivery device shown in FIG. 1 taken along line 4A-4A with the bolus button in an initial locked position.

Referring to FIG. 10A, the bolus actuator 322 can include a position lock or rack 1068 that couples the bolus button 966 and the second moveable barrier 232. In one embodiment, the rack 1068 engages a housing pawl 1170 (see FIGS. 11A and 2) fixed relative to the manifold 226 that prevents the rack 1068 and second moveable barrier 232 from moving outwardly toward the bolus button 966. In one embodiment, the bolus button 966 is spring biased away from the second moveable barrier 232 and includes a pawl 966a that engages with the rack 1068 to advance the rack 1068 one or more predetermined one way ratchets or teeth and resets once permitted.

Figure 10B:
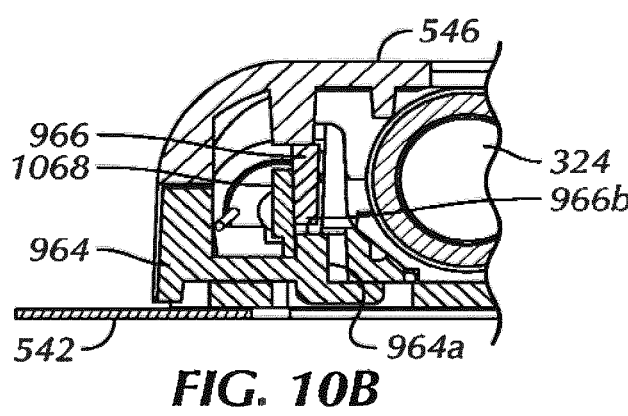
FIG. 10B is a partial, front, cross sectional view of the fluid delivery device shown in FIG. 10A taken along line 10B-10B.
Figure 11A:
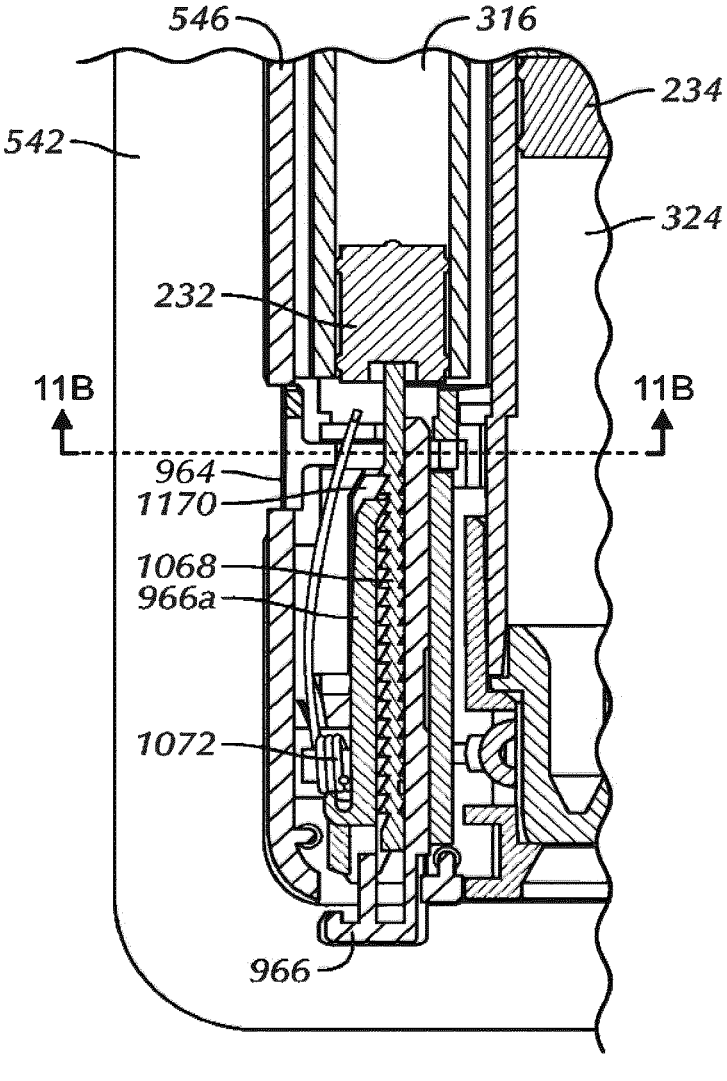
FIG. 11A is a partial, top, cross sectional view of the fluid delivery device shown in FIG. 1 taken along line 4A-4A with the bolus button in the released position.
Figure 11B:
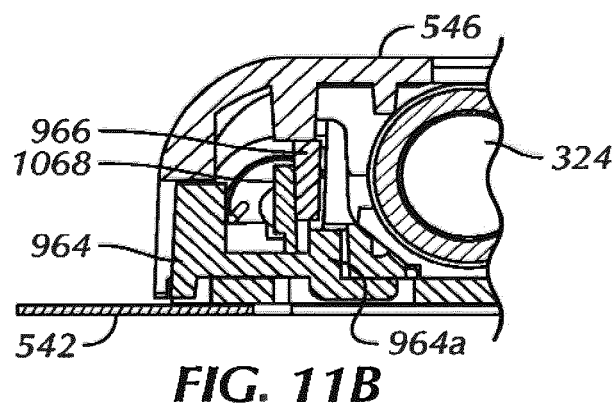
FIG. 11B is a partial, front, cross sectional view of the fluid delivery device shown in FIG. 11A taken along line 11B-11B.
Figure 12A:
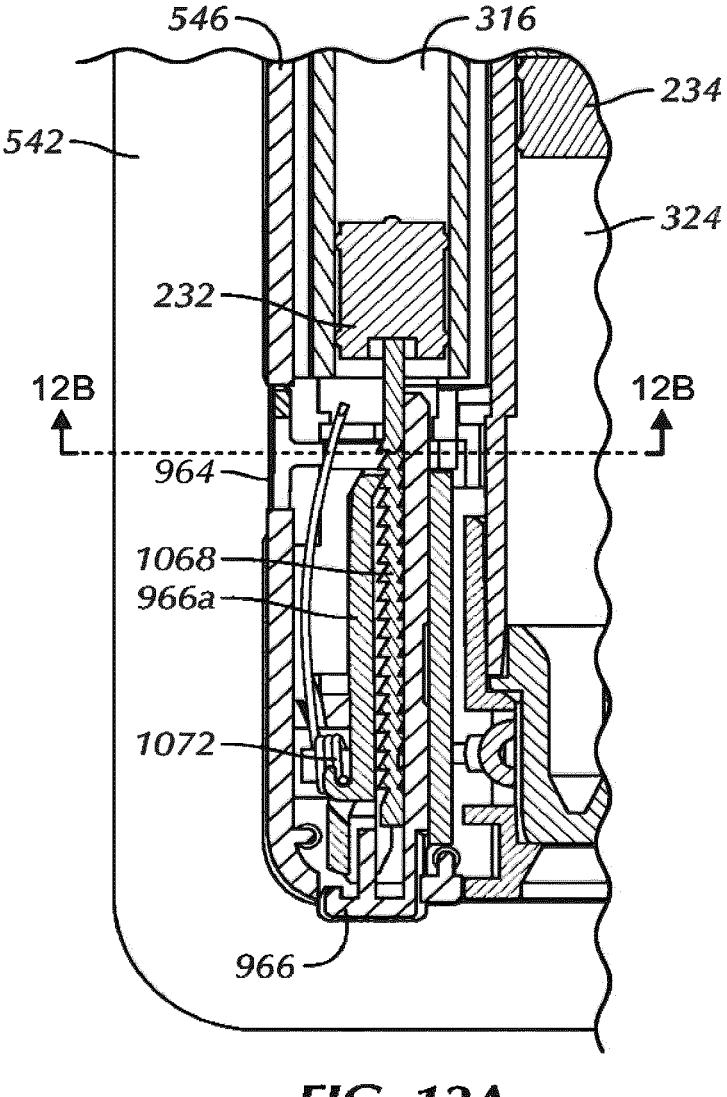
FIG. 12A is a partial, top, cross sectional view of the fluid delivery device shown in FIG. 1 taken along line 4A-4A with the bolus button in a locked position after delivery a bolus dose.
Figure 12B:
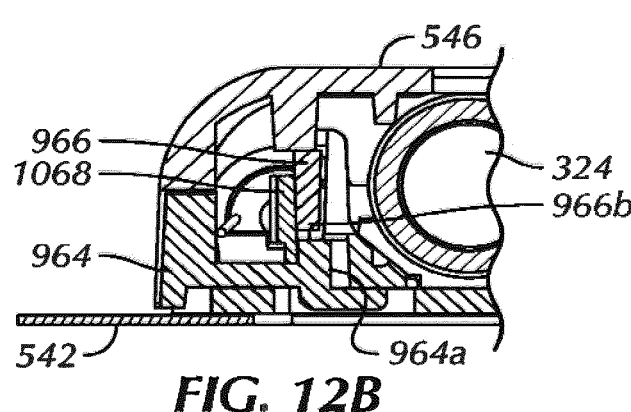
FIG. 12B is a partial, front, cross sectional view of the fluid delivery device shown in FIG. 12A taken along line 12B-12B.
Figure 13A:
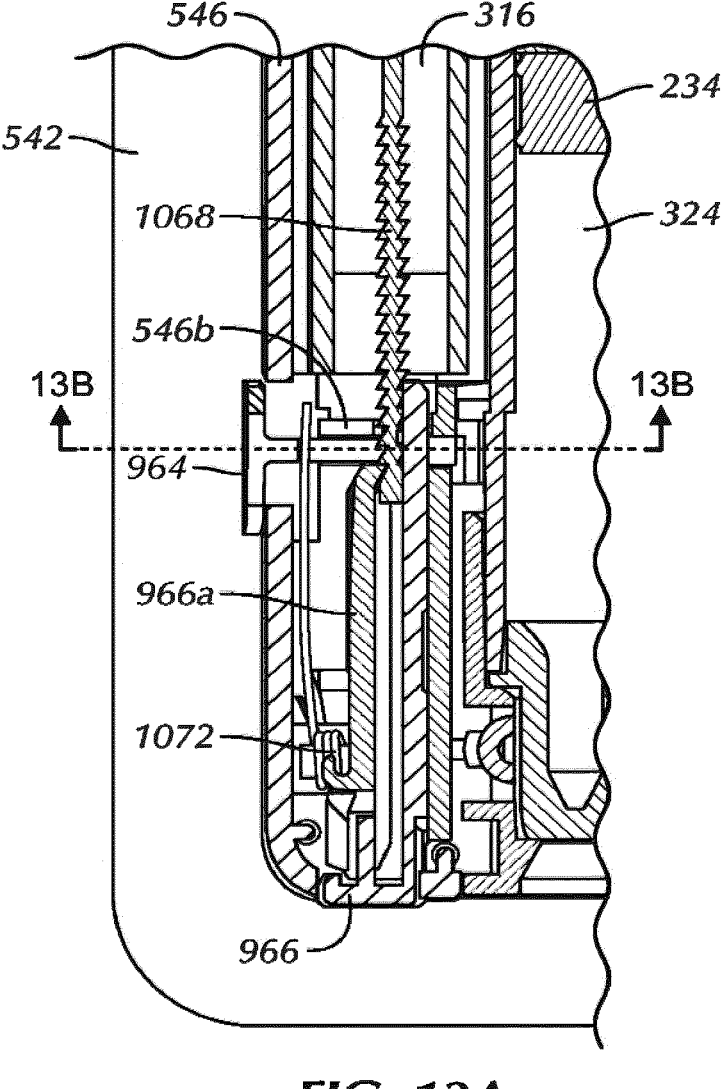
FIG. 13A is a partial, top, cross sectional view of the fluid delivery device shown in FIG. 1 taken along line 4A-4A with the bolus button in the locked position and a release button in a locked position and indicating that the bolus button has been completely deployed.
Figure 13B:
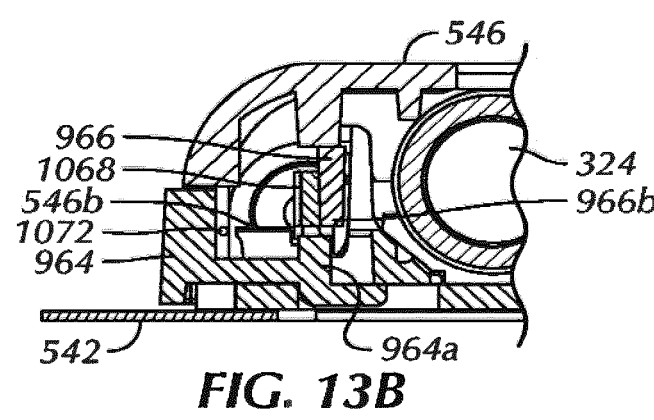
FIG. 13B is a partial, front, cross sectional view of the fluid delivery device shown in FIG. 13A taken along line 13B-13B.

Referring to FIG. 10B, the bolus release button 964 can engage with the bolus button 966 to control when the bolus button 966 is reset. In one embodiment, the bolus release button 964 includes a projection 964a that engages the bolus button 966 by selectively sliding through and being positioned within aperture 966b of the bolus button 966 (shown best in FIG. 2). In one embodiment, when the projection 964a of the bolus release button 964 is within the aperture 966b (as shown in FIGS. 10B, 12B and 13B) bolus button 966 on either end of the aperture 966b abuts against the projection 964a and prevents movement of the bolus button 966 in either direction. In one embodiment, depressing the bolus button 966 moves the projection 964a out of the aperture 966b and allows the bolus button 966 to be reset by the spring bias (as shown in FIG. 11B). In one embodiment, the bolus release button 966 is spring biased such that releasing the bolus release button 966 after depressing the bolus release button 966 biases the projection 964a against the side of the bolus release button 964 adjacent to the aperture 966b and such that once the aperture aligns with the projection 964a upon depressing the bolus button 966 the projection 964a immediately mates with the aperture 966b. In one embodiment, the bolus button 966 is spring biased with a torsion spring 1072. In one embodiment, the same torsion spring 1072 that biases the bolus button 966 spring biases the bolus release button 964.

FIGS. 10A-13B depict an exemplary sequence of events in bolus dosing. FIGS. 10A and 10B depict the position of the bolus button 966 and bolus release button 964 prior to bolus dosing; the bolus release button 964 is in the enabled position, and the bolus button 966 is locked in the depressed position. FIGS. 11A-11B depict the enabling step; the user depresses the bolus release button 964 to its stop position, causing the bolus button 966 to move to the extended position. The bolus button 966 is now enabled for one incremental dose. FIGS. 12A-12B illustrate delivery of a bolus dose; the user depresses the bolus button 966 to the stop position, causing the bolus actuator 322 to advance one increment, displacing the second moveable barrier 232 and dispensing one bolus dose. The bolus release button 964 is returned to the enabled position. FIGS. 13A-13B illustrate delivery of the last bolus dose of the device; the user depresses the bolus button 966 to its stop position, causing the bolus actuator 322 to advance one increment, displacing the second moveable barrier 232 and dispensing the final bolus dose. This activates a lock-out feature of the fluid delivery device 110, causing the bolus release button 964 to slide through an aperture 1068a (see FIG. 8) in the rack 1068 to the lock-out position. In one embodiment, once the bolus release button 964 extends outwardly through aperture 1068a, the torsion spring 1072 slides off a ledge 546b of the housing 546 and extends between the bolus release button 964 and the ledge 546b to retain the bolus release button 964 in the lock-out position (See FIG. 13B). The bolus release button 964 can be locked in place to prevent subsequent operation and to indicate to the user that all of the bolus doses have been delivered.

In one embodiment, the bolus button 966 remains in the depressed position slightly proud of (i.e. raised, projecting or extending from) the outer device surface of the housing 546. As a result of the user's pressing the bolus release button 964, the bolus actuator 322 can engage one bolus increment as the bolus button 966 extends further from the housing 546. When the user then depresses the bolus button 966 back to its original position (i.e., slightly proud of the housing 546), the bolus actuator 322 advances the second moveable barrier 232 a fixed amount or increment. The resulting movement of the second moveable barrier 232 displaces the hydraulic fluid and in turn displaces the third movable barrier 234 by essentially the same volume increment, dispensing a bolus dose of fluid from the fluid delivery device 110.

The second moveable barrier 232 can be capable of maintaining a seal as it translates within the hydraulic bolus chamber 316. In one embodiment, the second moveable barrier 232 is displaced by the rack 1068 by the distance equal to one ratchet spacing at a time per activation of the bolus button 966.

Figure 14:
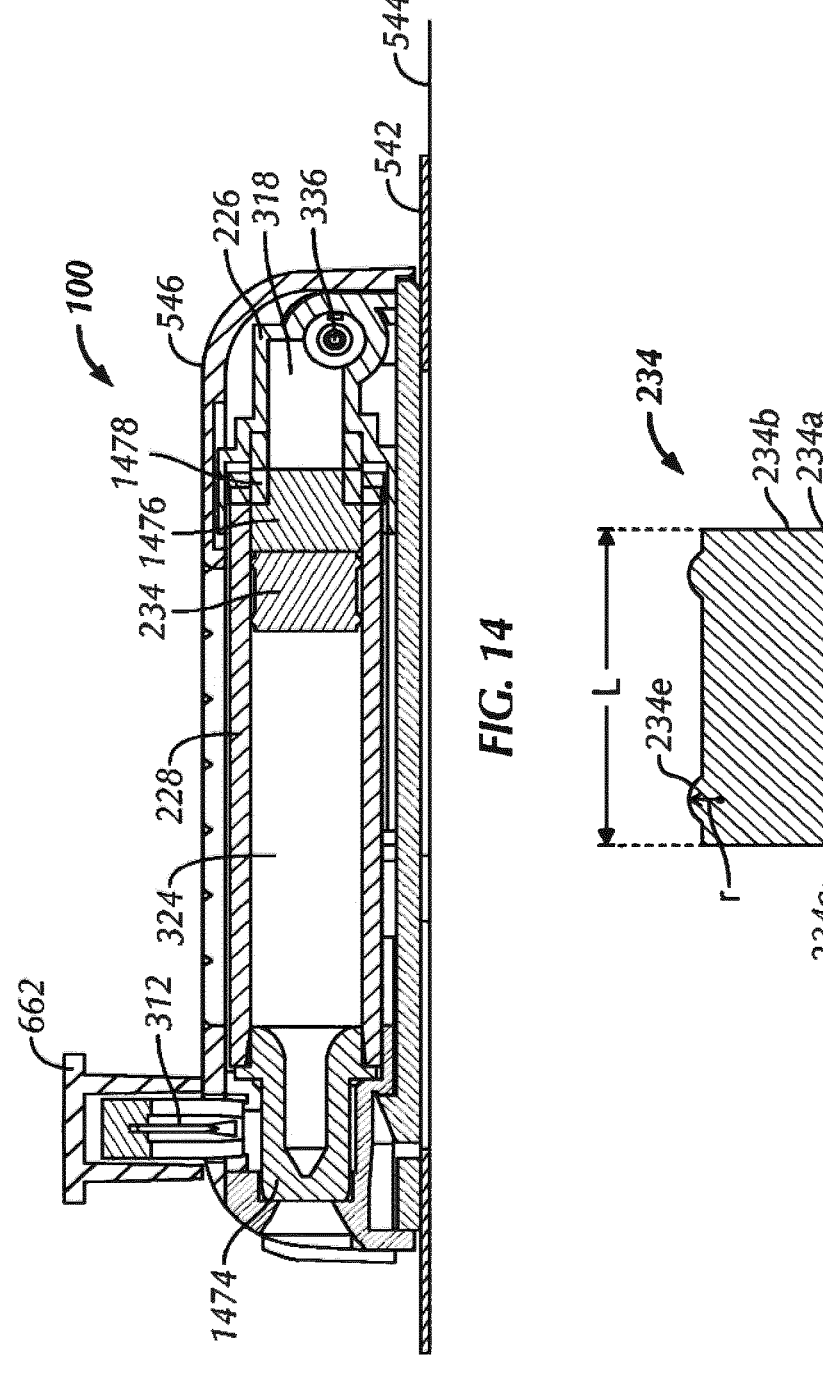
FIG. 14 is a side cross sectional view of a pump chamber, medicinal piston and a fluid reservoir of the fluid delivery device shown in FIG. 1 taken along line 14-14.

Referring to FIG. 14, in one embodiment, the fluid reservoir 324 initially is filled with a quantity of the fluid to be delivered to the user. In another embodiment, the fluid reservoir 324 can be filled by the user prior to use. In one embodiment, the fluid cartridge 228 of the fluid reservoir 324 is comprised of a rigid material. In one embodiment, the fluid cartridge 228 is comprised of Topas 6017 S-04. In some embodiments, the fluid cartridge 228 can be comprised of a polymer due to the reduce length of time of exposure of the fluid to the fluid cartridge 228 (for example, 24 hours after the user fills the fluid cartridge 228 and uses it) where previous fluid cartridges had to be comprised of a glass or other material having lower leachable and extractible properties for storage of the fluid over an extended period of time. Additionally, because known delivery devices include electronics, such devices are not practical for one day disposable use as is a purely mechanical device as disclosed in certain embodiments of the fluid delivery device 110 herein.

In the case of a medicament, the quantity of fluid can be pre-determined by a medical professional in order to provide the necessary dosing over a pre-determined period of time. The volume of the fluid reservoir 324 can be about 100 μl, 500 μl, 1 ml, 3 ml, 5 ml, 10 ml, 30 ml, 50 ml, 100 ml or more. The fluid cartridge 228 can include a septum 1474 within the distal end of the fluid cartridge 228. In one embodiment, the septum 1474 acts as a stopper. In other embodiments, the septum 1474 can be at least portion of the sidewall (not shown). In one embodiment, the fluid cartridge 228 includes a spacer 1476 on the hydraulic fluid side of the third moveable barrier 234 such that the size of the fluid cartridge 228 can adapt to a range of fluid volumes by varying the size of the spacer 1476. In one embodiment, the space 1476 can be brightly colored to help indicate the level of fluid within the fluid cartridge 228. The fluid cartridge 228 can include a seal 1478 that has an opening 1478a (see FIG. 2) such that the seal 1478 seals the fluid cartridge 228 to the manifold 226 while allowing the hydraulic fluid to pass through to either the spacer 1476 and/or the third moveable barrier 234.

In one embodiment, the septum 1474 is composed of a flexible material such as rubber and fits within fluid cartridge 228, forming a seal on the end opposite the third moveable barrier 234. The septum 1474 can be a hollow cylinder open only at the end that is installed in the fluid cartridge 228. The septum can remain stationary and is positioned to align with the needle 312. When the needle 312 pierces the side the septum 1474, the fluid path between the fluid delivery device 110 and the outside environment is opened, allowing the fluid to flow from the fluid delivery device 110. In one embodiment, the septum 1474 is exposed through a side of the housing 546 to allow for the user to fill the fluid reservoir 324. The septum 1474 can have a hardness sufficient to allow the needle 312 to move relative to the remainder of the fluid delivery device 110 as described in further detail below. In one embodiment, the septum 1474 has a hardness of 50 shore A.

Figure 15:
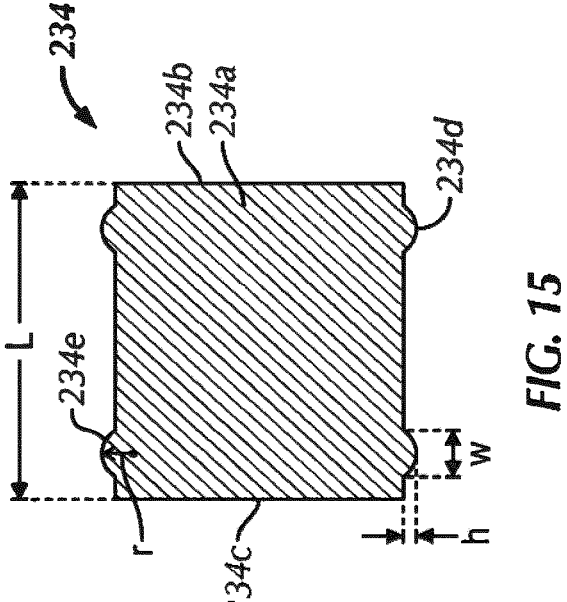
FIG. 15 is an enlarged side cross sectional view of the medicinal piston shown in FIG. 14.

Referring to FIG. 15, the third moveable barrier 234 can be a plunger that slides within the fluid cartridge 228. Typically, pistons can have imprecise sizing and compressibility characteristics because the impact on the delivery rate is not critical. In one embodiment, the third moveable barrier 234 of the fluid delivery device 110 however, is configured to minimize any impact on the fluid delivery rate. In one embodiment, the third moveable barrier 234 is comprised of a flexible material to form a seal between the hydraulic fluid and the fluid to be delivered to the user. In one embodiment, the third moveable barrier 234 has a similar configuration to the second moveable barrier 232. In one embodiment, the axial compressibility is minimized. In one embodiment, the axial compressibility of the second and third moveable barriers 232, 234 can be greater than the axial compressibility of the first moveable barrier 230 due to the lower pressure differentials acting on the second and third moveable barriers 232, 234. In such an embodiment, the lower axial compressibility allows for a thickness or length L that is greater than the thickness t of the first moveable barrier 230 and allows two points of contact. In one embodiment, the third moveable barrier 234 is comprised of a single material having a durometer between approximately 35 and approximately 65 shore A. In one embodiment, the durometer of the third moveable barrier 234 is between approximately 35 and approximately 65 shore A for a fluid cartridge 228 comprised of a polymer. In another embodiment, the durometer of the third moveable barrier 234 is between approximately 35 and approximately 45 shore A for a fluid cartridge 228 comprised of glass. In one embodiment, the durometer of the third moveable barrier 234 is 55 shore A with a fluid cartridge 228 comprised of a polymer. In one embodiment, the third moveable barrier 234 is comprised of Butyl Rubber. In one embodiment, the third moveable barrier 234 is coated with 0.0001 inch parylene C. In one embodiment, the third moveable barrier 234 has a minor diameter of approximately 0.2425 inches and a major diameter of approximately 0.2615 inches f 0.002 inches.

In one embodiment, the third moveable barrier 234 includes a body 234a having a first end 234b and a second end 234c. The third moveable barrier 234 can include a first flange 234d and a second flange 234e. In one embodiment, the first and second flanges 234d, 234e are integral with the body 234a and extend radially outwardly from the body 234a proximate the first end and second ends 234b, 234c respectively, in an uncompressed state. The first and second flanges 234d, 234e can be configured such that contact with the fluid cartridge 228 is minimized. Having the first and second flanges 234d, 234e be integral with the body 234a can prevent roll over and flash points that occur with the use of separate o-rings. In one embodiment, the first and second flanges 234d, 234e have a curved cross sectional periphery in the uncompressed state. In one embodiment, the curve has a substantially constant radius r in the uncompressed state. In one embodiment, the first and second flanges 234d, 234e are spaced from the first and second ends 234b, 234c respectively in order to provide proper support for the first and second flanges 234d, 234e.

In one embodiment, control of the contact area of third moveable barrier 234 to the inner wall of the fluid cartridge 228 is addressed by the structural design of the first and second flanges 234d, 234e. In one embodiment, the first and second flanges 234d, 234e have a circular side cross sectional profile. In this embodiment a circular profile on the outer surface of a plunger constructed of an elastomeric material presents a small contact area that can be deformed with a minimal change in force. Though individual pistons and cylinders vary in size due to manufacturing tolerances, the contact area variation is reduced by the configurations disclosed herein. Providing two flanges provides redundant sealing to insure the isolation of the fluid from the hydraulic fluid.

In additional embodiments, the coefficient of friction between the third moveable barrier 234 and the fluid reservoir 324 is controlled by appropriate selection of contact materials. In this embodiment, one or more suitable coating agents are applied to the outer surface of the third moveable barrier 234 and/or the inner surface of the fluid reservoir 324 to minimize both the coefficient of friction and the variation of the coefficient of friction from device to device. In addition, a coating process using Parylene 'C' material can be used. A film coating with Parylene 'C' material greater than about 0.0001 inch (2.5 microns) has proven to contribute to controlling the movement of the third moveable barrier 234. The Parylene coating is preferably conformal and of uniform thickness and is substantially free of any voids or pinholes. Parylene can be applied at the molecular level by a vacuum deposition process at ambient temperature. Film coatings from about 0.100 to 76 microns are possible in a single operation. In one embodiment, no catalysts or solvents are required, and no foreign substances are introduced that could degrade the coated surface. Parylene 'C' is a modified version of Parylene which can provide a better combination of electrical and physical properties including low moisture and gas permeability.

Figure 16A:
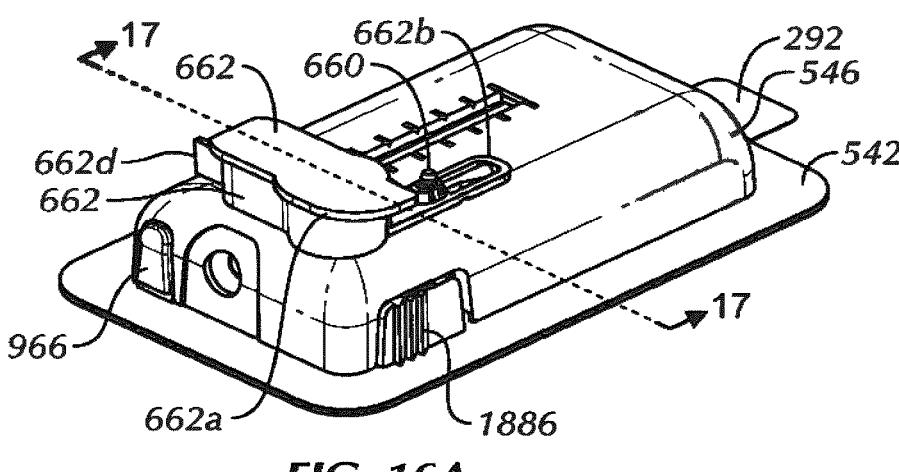
FIG. 16A is a perspective view of the fluid delivery device shown in FIG. 1 in an initial or storage position.
Figure 16B:
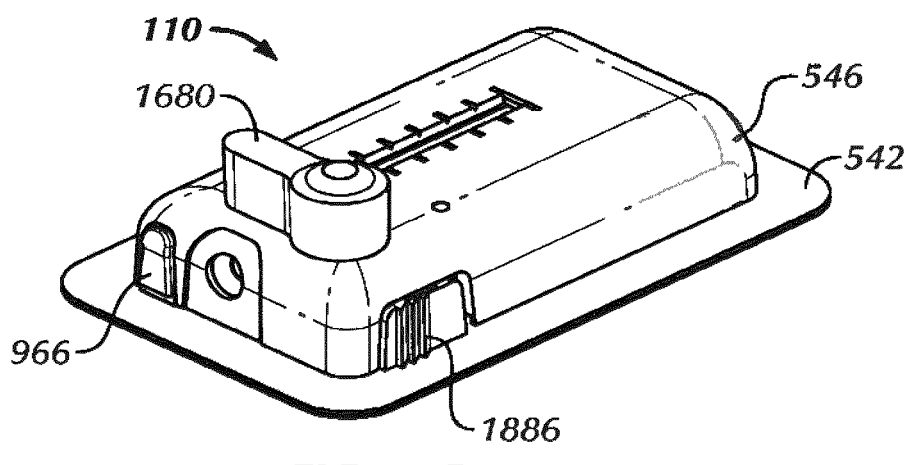
FIG. 16B is a perspective view of the fluid delivery device shown in FIG. 1 with the button cap removed and the biasing members engaged.
Figure 16C:
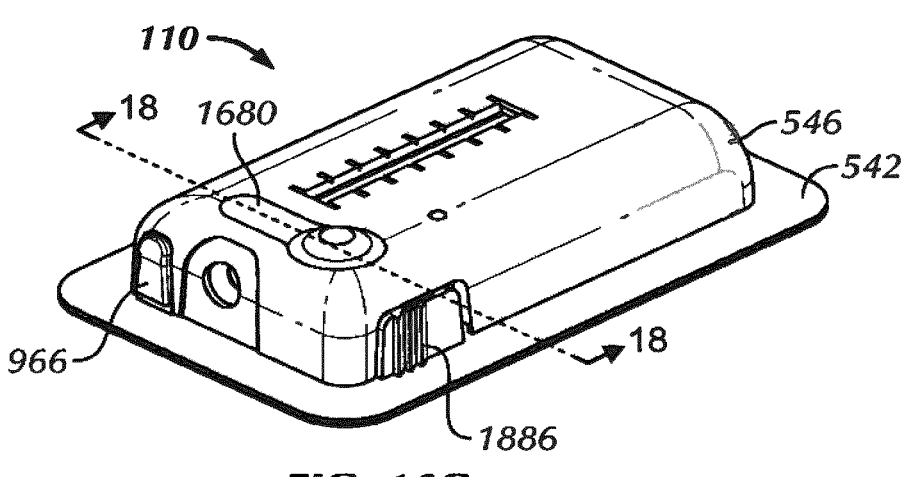
FIG. 16C is a perspective view of the fluid delivery device shown in FIG. 1 in the engaged position.

Referring to FIGS. 16A-16C, in one embodiment, the fluid delivery device 110 has multiple operable states. In a first operable state or storage position (FIG. 16A), the needle 312 is not engaged or is separated from the fluid reservoir 324 and does not extend from the housing 546 (i.e. not inserted into the body). In a second operable state or engageable position (FIG. 16B), the needle 312 is able to be engaged with the fluid reservoir 324. In a third operable state or engaged or activated position (FIG. 16C), the needle 312 is in fluid communication with the fluid to be delivered and is inserted into the body or available for insertion into the body. In a fourth operable state or disengaged or disposable position (not shown), the needle 312 is again separated from the fluid to be delivered, is not inserted into the body, and is fixedly retained (locked) within the housing 546.

In one embodiment, the button cover 662 shrouds the needle 312 preventing accidental depression of the needle 312 during handling and shipping of the fluid delivery device 110. In one embodiment, the button cover 662 includes a flange 662a to facilitate grasping and removing the button cover 662 by the user. In one embodiment, the button cover 662 has a projection 662b for coupling with the pin 660. The button cover 662 can include indicia 662c such as the word "Remove" to indicate what the user should do with the button cover 662 (See FIG. 2). In one embodiment, the button cover 662 includes a tab 662d for providing leverage against the housing 546 as the button cover 662 is removed by holding the flange 662a on the opposite side of the button cover 662. In one embodiment, when the button cover 662 is removed, a needle button 1680 coupled to the needle 312 is exposed (FIG. 16B).

Figure 19:
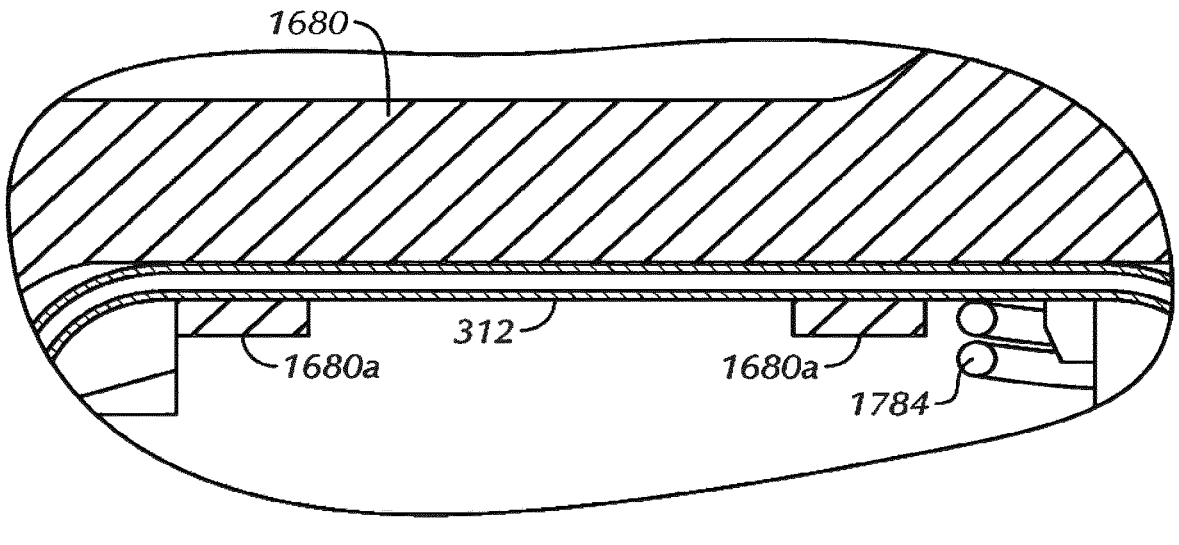
FIG. 19 is an enlarged front cross sectional view of a portion of a needle with a needle cap shown in FIG. 18.

In one embodiment, the needle 312 is fixed to the needle button 1680. In one embodiment, the needle 312 is heat staked to the needle button 1680 at points 1680a as shown in FIG. 19. In other embodiments, the needle 312 is moveable relative to the needle button 1680. In one embodiment, removal of the button cover 662 simultaneously removes the pin 660 from the basal actuator 320 to release or activate the basal actuator 320 such that it acts on the hydraulic fluid. Thus, in preferred embodiments, the button cover 662 performs the dual functions of shrouding and protecting the needle button 1680 to prevent unintentional activation of the needle 312 and simultaneously controls activation of the basal actuator 320.

Figure 17:
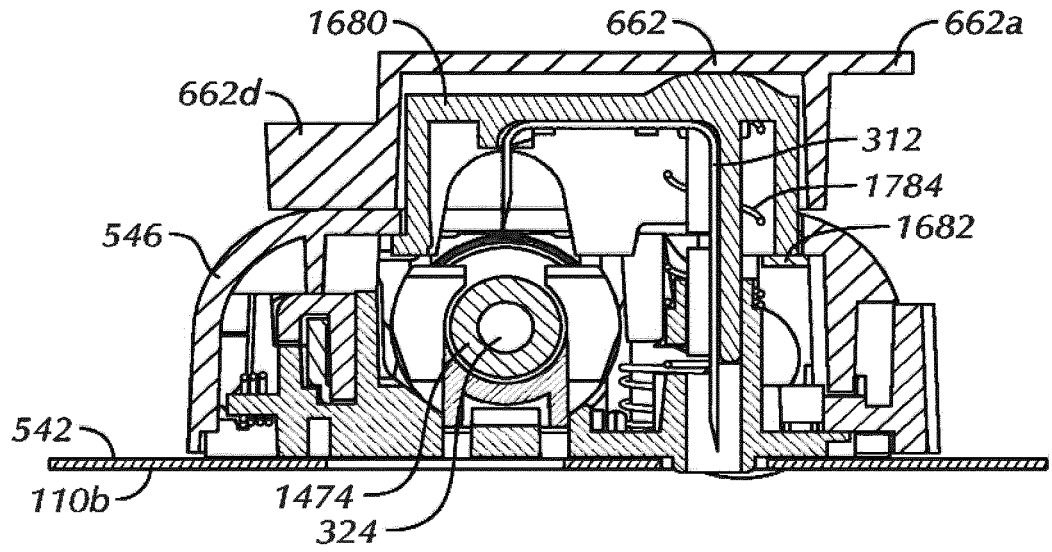
FIG. 17 is a front cross sectional view of the fluid delivery device shown in FIG. 16A taken along line 17-17.
Figure 18:
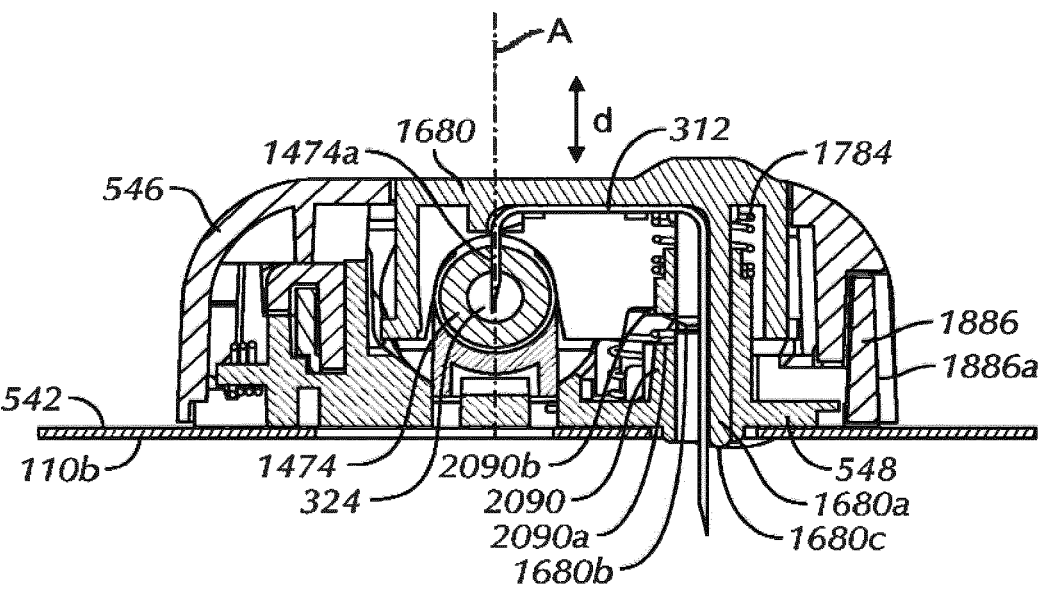
FIG. 18 is a front cross sectional view of the fluid delivery device shown in FIG. 16C taken along line 18-18.

Referring to FIGS. 17 and 18, in one embodiment, the needle button 1680 deploys the needle 312 when depressed (FIG. 18). The needle button 1680 can be spring biased away from the septum 1474. In one embodiment, the needle button 1680 is spring biased by a compression spring 1784 as described further below. A first force can be required to move the needle button 1680 from the initial position. In one embodiment, the first force is greater than a second force that is required to move the needle button 1680 the remainder of way (i.e. at least greater than the force from the spring 1784) to the engaged position to help users overcome the fear of depressing the needle 312 into the skin surface 544. In one embodiment, one or more breakable tabs 1682 extend from the housing 546 such that the tabs 1682 break upon providing the first force in the first direction d such that the user completes the deployment or insertion of the needle 312 quickly and fully after the tabs 1682 release the needle button 1680 and helps to prevent failed or partial insertion or engagement attempts. In the deployable position, the needle 312 can be moveable nearly exclusively in the engagement direction (i.e. toward the septum 1474) such that the needle 312 enters the septum and the user with little to no movement in the transverse direction to help ensure proper engagement. Once the needle 312 is in the engaged position, the needle 312 can then move relative to the remainder of the fluid delivery device 110 to reduce pain caused by movement of the needle 312 relative to the user as described below. In one embodiment, the needle 312 is flexible and restraining movement of the needle 312 during engagement aids in proper engagement of the needle 312.

In one embodiment, the needle 312 extends from the fluid reservoir 324, through the pierceable member or septum 1474 at a connection point 1474a and out of the housing 546. The needle 312 can be moveable relative to the septum 1474 or the fluid delivery device 110 can move relative to the needle 312 such that when the needle 312 extends into the skin surface 544 in the engaged position, movement of the needle 312 relative to the user caused by movement of the fluid delivery device 110 is reduced. Minimizing the movement of the needle 312 relative to the user can help to reduce pain or "pinching" caused by the needle 312.

In one embodiment, the needle 312 is configured to translate in a direction perpendicular to the septum 1474, e.g. direction d in FIG. 18, and pivot about the connection point 1474a in all directions. In one embodiment, the pivot of the needle 312 about the connection point 1474a is within the boundaries of an imaginary hour glass shaped path (not shown) proximate the septum 1474. In one embodiment, the entire needle 312 is configured to pivot about the connection point 1474a due to the flexibility of the septum 1474 and is limited by the connection between the needle button 1680 and the housing 546. In one embodiment, the needle 312 is configured to be entirely within or at least shrouded by the housing 546 and disengaged from the fluid reservoir 324 in an initial position (FIG. 17) and fluidly coupled with the fluid reservoir 324 and extending from the housing 546 in an engaged position (FIG. 18). In one embodiment, the needle 312 is configured to pierce the pierceable member 1474 after extending from the housing 546 when moving the needle 312 from the initial position to the engaged position such that the fluid does not exit onto the skin surface 544 and interfere with the adhesion of the adhesive patch 542. In one embodiment, the needle 312 is configured such that the needle 312 pierces the skin surface 544 approximately simultaneously to when the needle 312 pierces the pierceable member 1474.

In one embodiment, the needle 312 is generally J-shaped such that its two ends are pointing in the same direction but are axially and laterally spaced from one another. In one embodiment, the needle 312 includes two generally perpendicular bends with one end of the needle 312 being shorter than the other. In one embodiment, the septum 1474, or at least a surface tangent to the connection point 1474a, is generally parallel to a bottom surface 110b of the housing from which the needle 312 extends in the engaged position. In one embodiment, the needle 312 is a microneedle. In one embodiment, the needle 312 is a fine gauge needle. In one embodiment, the needle 312 is a 30 gauge needle. A person of skill in the art will appreciate that the gauge of the needle may be adjusted (e.g., increased or decreased) depending on the viscosity of the pharmaceutical composition, and the desired release rate of the pharmaceutical composition from the fluid delivery device. For example, the gauge of the needle may be decreased (e.g., an increase in the diameter of the needle) in order to maintain a given release rate of a more viscous pharmaceutical composition. In another example, the gauge of the needle may be increased (e.g., a decrease in the diameter of the needle) in order to maintain a given release rate of a less viscous pharmaceutical composition. In one embodiment, both ends of the needle 312 are beveled to help facilitate piercing of the septum 1474 and the skin surface 544. In one embodiment, the needle 312 is configured to rotate about an imaginary axis A that extends through the connection point 1474a perpendicular to the septum 1474 as shown in FIG. 18 such that the fluid delivery device can rotate about the axis A without, or at least reduces, the end of the needle 312 extending into the user moving in an arched path.

In one embodiment, once the needle 312 is in the engaged position the needle button 1680 is locked into place and the fluid in the fluid reservoir is in liquid communication with the outside environment (e.g., the body) via the needle 312. The locking member 2088 can be configured to keep the first and second ends of the needle 312 disengaged from the user and the fluid reservoir 324 and contained within the housing 546 in a locked position upon moving the needle from the engaged position (FIG. 18) to the locked position (FIG. 23). In the locked position, the needle 312 can be kept from redeployment or engagement such that the housing 546 acts as its own sharps container. In one embodiment, the needle 312 is moved to the locked position through use of a needle release or lock button 1886.

Figure 20:
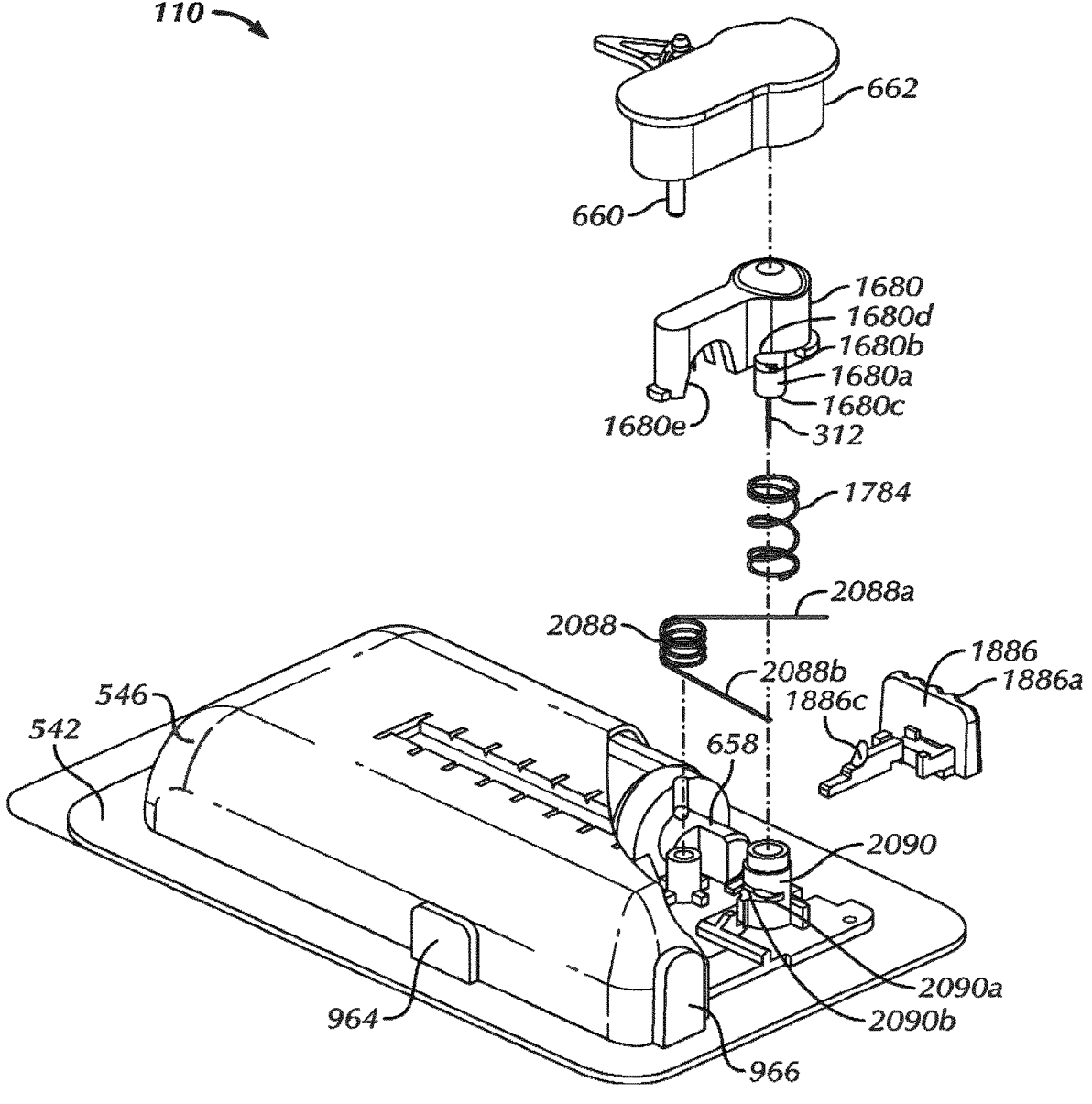
FIG. 20 is a partially exploded cut away view of a lock out assembly of the fluid delivery device of FIG. 1.
Figure 21:
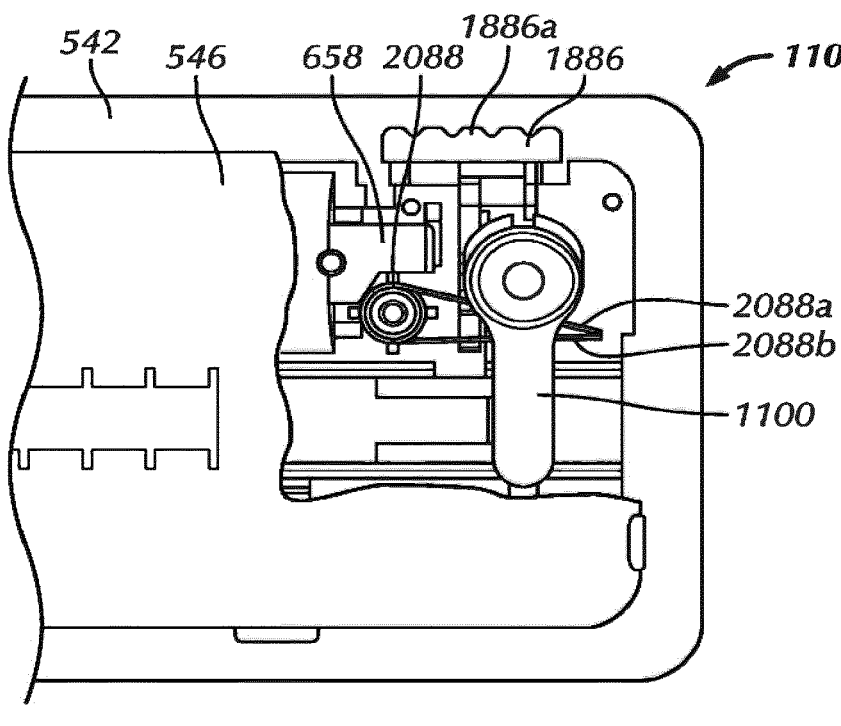
FIG. 21 is a top, partially cut away view of a lock out assembly of the fluid delivery device of FIG. 1 in an initial or ready to be engaged position.

Referring to FIG. 20, in certain embodiments, the spring 1784 is located between the needle button 1680 and the base 548 and surrounds a boss or sleeve 1680a of the needle button 1680 extending partially over the needle 312. In one embodiment, the spring 1784 becomes compressed when needle button 1680 is locked in the depressed, engaged or inserted position (FIG. 18) to bias the needle button 1680 away from the septum 1474. The needle button 1680 can be retained in the inserted position by a locking member as described further below. The locking member 2088 can be released when the user is finished with the fluid delivery device 110. In one embodiment, prior to removing the fluid delivery device 110 from the body, the user activates the lock button 1886 to retract the needle 312 from the user and into the housing 546. In other embodiments, the needle 312 is automatically retracted after the fluid reservoir 324 is substantially empty or automatically upon removal of the fluid delivery device 110 from the skin surface 544.

Figure 22:
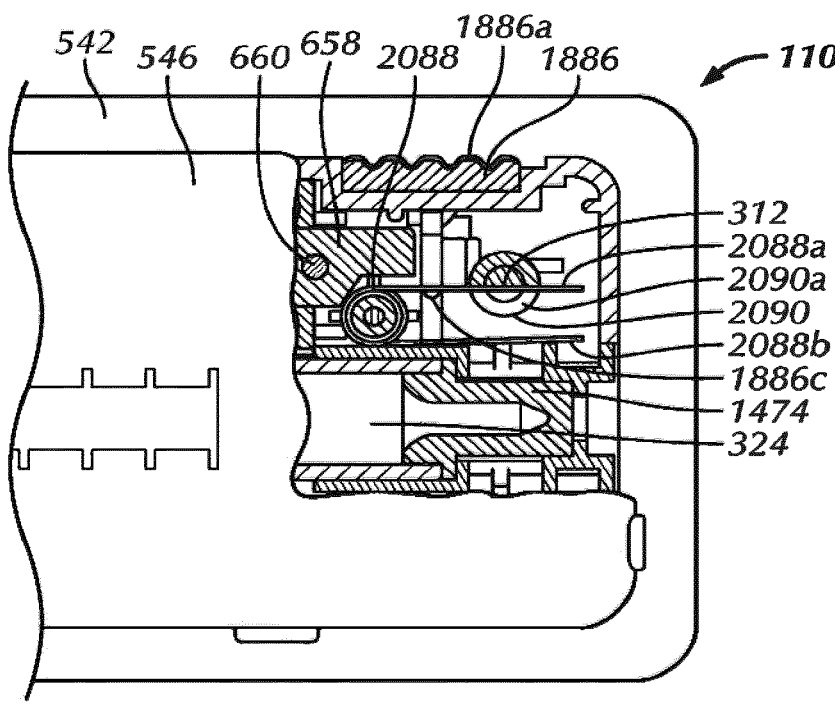
FIG. 22 is a top, partially cut away view of a lock out assembly of the fluid delivery device shown in FIG. 1 in a locked out position.

In one embodiment, the locking member 2088 is a spring. In one embodiment, the locking member 2088 is comprised of a helical torsion spring. In one embodiment, the locking member 2088 biases the lock button 1886 and interacts with features of the needle button 1680 and the base 548 to releasably retain the needle 312 in the depressed or inserted position (FIG. 18) and unreleasably locked in the lock-out position (FIG. 22).

In one embodiment, the locking member 2088 is coupled to or engageable with the lock button 1886. In one embodiment, the lock button 1886 has a surface 1886a exposed through the housing 546. In one embodiment, the surface 1886a of the lock button 1886 is exposed through an aperture in the housing 546 on a first side of the housing 546 and the housing 546 has a surface on a second side of the housing 546 opposed to the first side of the housing and generally aligned with the lock button 1886 such that the user can grip the lock button 1886 and the housing 546 between a thumb and a finger to activate the lock button 1886 within engaging the bolus release button 964 preventing accidental activation of the lock button 1886 when using the bolus actuator 322. The lock button 1886 can include at last one projection 1886b extending from the surface to help facilitate grip with the user's hand. In one embodiment, the at least one projection 1886b is ramped (see FIG. 23A) to further facilitate grip and help indicate to the user by feel which direction the lock button 1886 should be urged.

Referring to FIG. 20, in one embodiment, the sleeve 1680a surrounds the needle 312 and the locking member 2088 is spring biased toward the sleeve 1680a. In one embodiment, the sleeve 1680a has at least one abutment surface configured to engage with the locking member 2088 to prevent at least one of engaging and disengaging the needle 312. In one embodiment, the at least one abutment surface includes a first abutment surface 1680b and a second abutment surface 1680b.

In one embodiment, the first abutment surface 1680b is axially spaced along the needle 312 from the second abutment surface 1680c. In one embodiment, the first abutment surface 1680b is a radially inwardly extending groove. In one embodiment, the second abutment surface 1680c is the distal end of the sleeve 1680. In other embodiments, the first and second abutment surfaces 1680b, 1680c are any surface such as a projection or groove that axially engages with the locking member 2088. In one embodiment, the base 548 includes an upwardly extending boss or guide 2090 for receiving and guiding the sleeve 1680a and engaging with the locking member 2088. In one embodiment, the guide 2090 loosely fits over the sleeve 1680a to allow some non-axial movement or pivot of the needle button 1680 relative to the base 2090 for the pivoting of the needle 312 as described above. The guide 2090 can include a groove 2090a configured to receive the locking member 2088. In one embodiment, the groove 2090a aligns with the first abutment surface 1680a in the engaged position (FIG. 18) and aligns with the second abutment surface 1680b in the locked-out position (FIG. 22). In one embodiment, the locking member 2088 engages with the first abutment surface 1680b to releasably retain the needle 312 in the engaged position (FIG. 18) and locking member 2088 engages with the second abutment surface 1680c to unreleasably retain the needle 312 in the locked position (FIG. 22). In one embodiment, the lock button 1886 is configured to position the locking member 2088 into the locked position upon disengaging the needle 312 from the user.

Referring to FIG. 20, in one embodiment, the locking member 2088 is configured to provide an audible feedback upon retaining the needle 312 in the engaged position so the user is assured that the needle 312 has been fully deployed and in the engaged position. In one embodiment, the guide 2090 includes a projection 2090b that facilitates creating an audible "click" by sliding the locking member 2088 over and into the groove 2090a and first abutment surface 1680a. In one embodiment, the projection 2090b is a ramped surface 1886c that is selectably engageable with the locking member 2088. In one embodiment, the locking member 2088 is biased against the guide 2090 above the groove 2090a (see FIG. 21) and depressing the needle button 1680 engages a surface 1680d with the locking member 2088 and slides the locking member 2088 down the guide 2090 over the projection 2090b and into the aligned groove 2090a and first abutment surface 1680a. In one embodiment, the needle button 1680 includes a cutout 1680e to fit over the septum 1474. In one embodiment, the cutout 1680e is loosely sized to the contour of the septum 1474 to support the needle 312 relative to the housing 546 but allows for the movement of the needle 312 described above.

In one embodiment, when the user depresses the needle button 1680, a free end or first arm 2088a of the locking member 2088 is moved from its initial preloaded position against the guide 2090 and into the aligned groove 2090a and first abutment surface 1680a. When the lock button 1886 is depressed the ramped surface 1886c can force the first arm 2088a of the locking member 2088 from the first abutment surface 1680a momentarily, allowing needle button 1680 to retract to the upright or initial position as a result of the force from the spring 1784. As the user continues to press the lock button 1886, the end of the first arm 2088a can abut a surface within the housing 546, preventing further rotation (similar to the position shown in FIG. 21). The mid section of the first arm can then deflect over the ramped surface 1886c of the lock button 1886 allowing the first arm 2088a to spring back into the groove 2090a (FIG. 22). The second abutment surface 1680c of the needle button 1680 can then be axially above the first arm 2088a extending across the guide 2090 preventing the needle button 1680 and needle 312 from further translation or re-depression/re-deployment (FIG. 22).

Figure 23A:
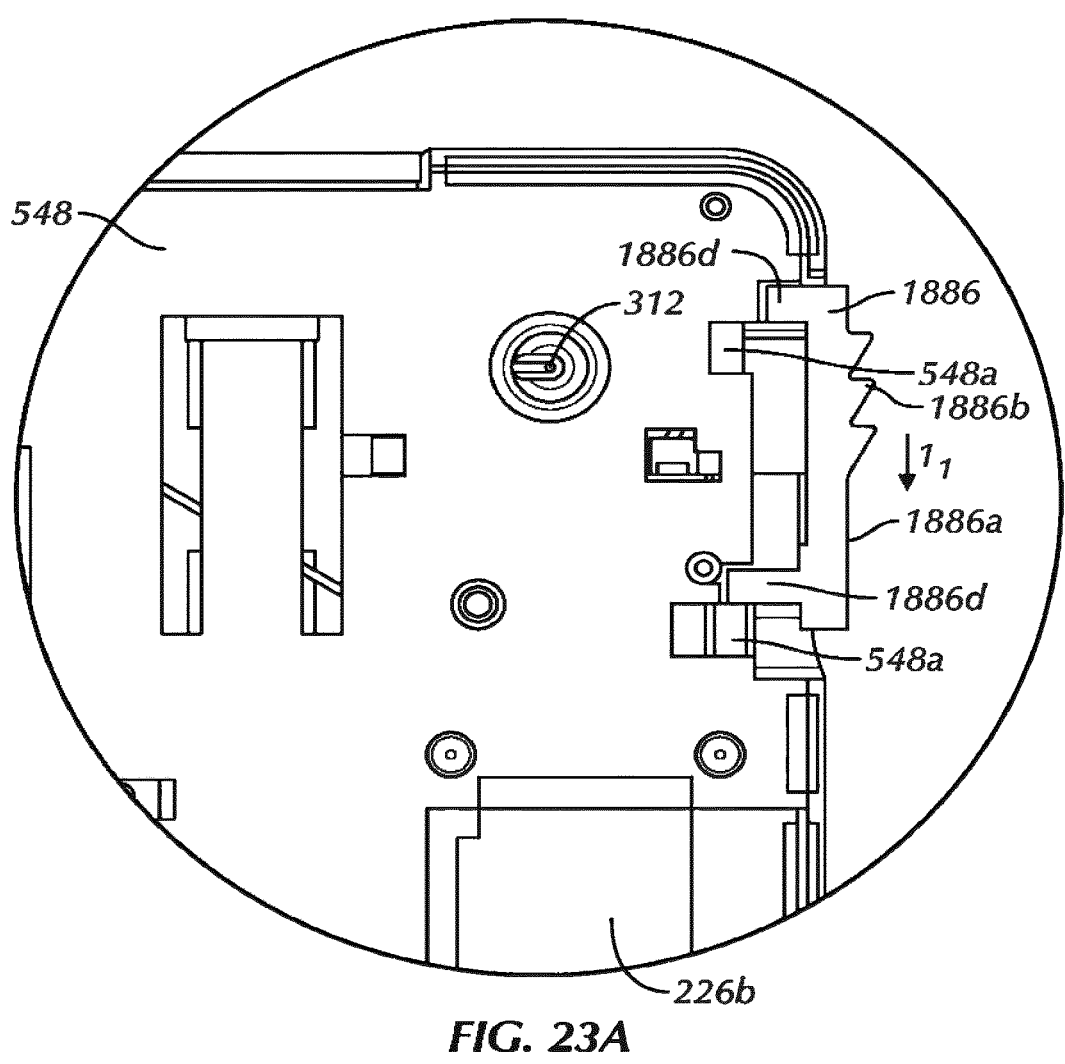
FIG. 23A is a partial bottom plan view of the fluid delivery device of FIG. 1 with the adhesive patch removed showing a lock button in an initial position.
Figure 23B:
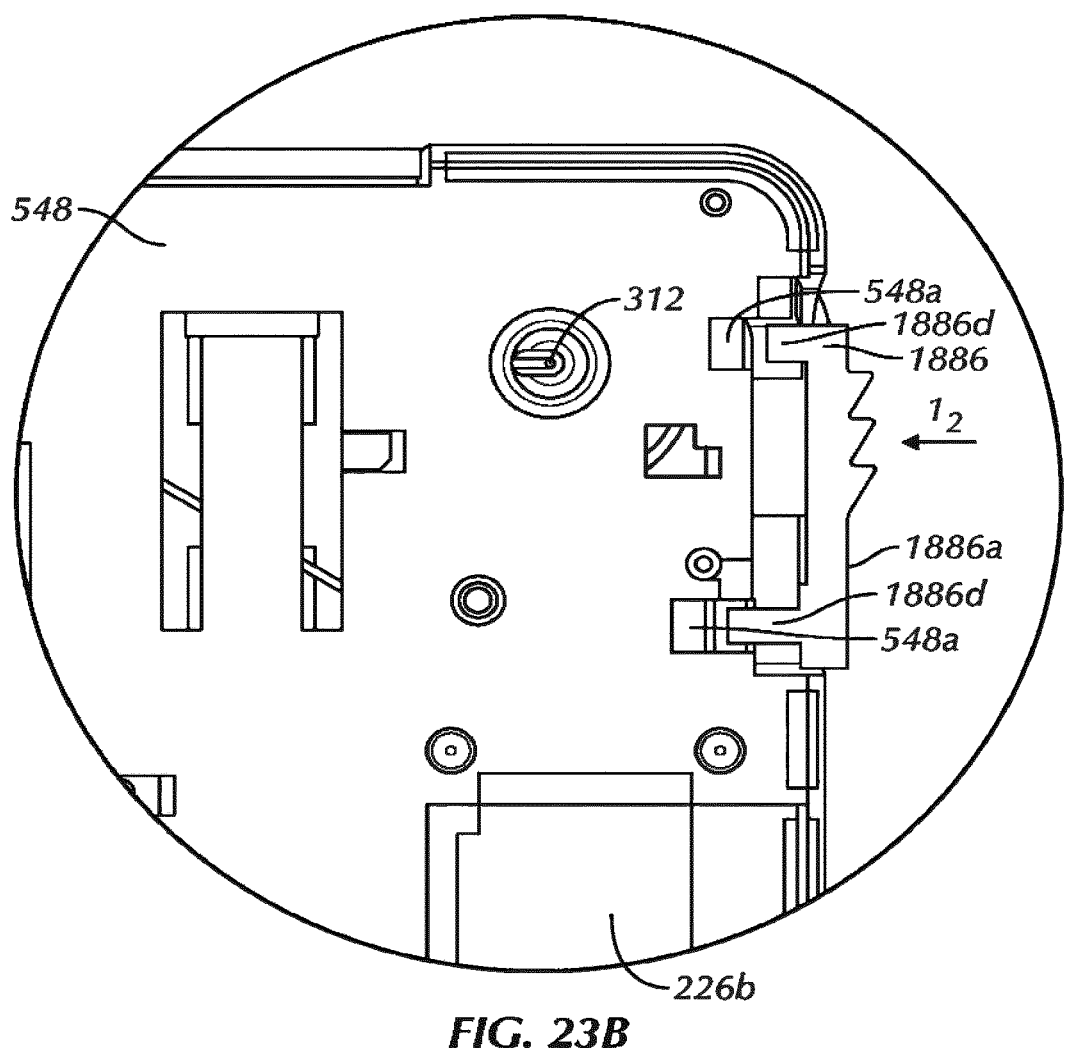
FIG. 23B is a partial bottom plan view of the fluid delivery device shown in FIG. 23A with the lock button moved in a first direction.
Figure 23C:
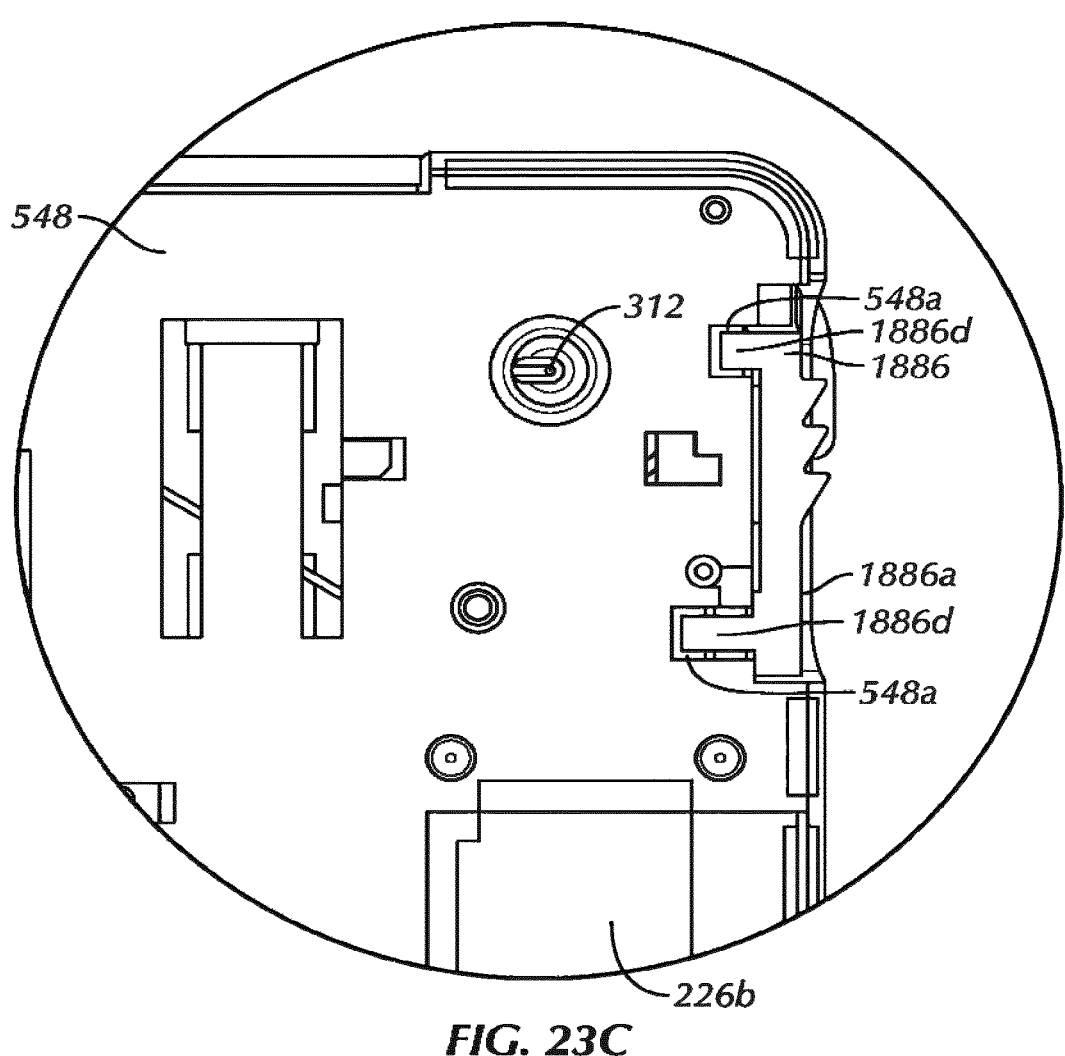
FIG. 23C is a partial bottom plan view of the fluid delivery device shown in FIG. 23A with the lock button moved in first and second directions.

Referring to FIGS. 23A-23C, in one embodiment, the lock button 1886 is configured to release the locking member 2088 only after completing two distinct motions to prevent accidental release of the locking member 2088. In one embodiment, the lock button 1886 is configured to move in a first direction $l_1$ and move in a second direction $l_2$ only after moving a predetermined distance in the first direction. In one embodiment, the lock button 1886 includes at least one projection 1886d and the housing or base 548 includes at least one slot 548a each configured to receive one of the at least one projection 1886d. In one embodiment, each at least one slot 548a is unaligned with one of the at least one projection 1886d in an initial position (FIG. 23A) and aligned with one of the at least one projection 1886d after moving the lock button 1886 the predetermined distance in the first direction $l_1$ (FIG. 23B) and each at least one slot 548a receiving one of the at least one projection 1886d after moving the lock button 1886 a predetermined distance in the second direction $l_2$. In one embodiment, the first and second directions $l_1$ and $l_2$ are linear translations. In one embodiment, the first direction is perpendicular to the second direction as shown in FIGS. 23A-23C. In other embodiments, the first and second directions are any directions such as curved and/or rotational. In one embodiment, the lock button 1886 is spring biased in a direction opposite the first direction. In one embodiment, the lock button 1886 is retained in the first direction by one or more breakaway tabs (not shown). In other embodiments, the lock button 1886 is comprised of more than one button.

Referring to FIG. 2, in some embodiments, the fluid delivery device 110 can include one or more view windows. View windows can be, for example, on the top side and/or the bottom side of the fluid delivery device 110. These view windows allow light penetration to facilitate point of care filling of the fluid reservoir 324, to increase viewability to determine level and viability of fluid, and to enhance user confidence by allowing observation by allowing the user to observe the relative position of the third moveable barrier 234 during delivery and/or filling. In one embodiment, the housing 546 includes a window 546a generally aligned with the fluid cartridge 228. In one embodiment, the adhesive patch 542 includes a window 542b. The window 542b can be a translucent area or simply a gap in the material. In one embodiment, the windows 542a and 542b are generally aligned. In one embodiment, the remainder of the exposed housing 546 is opaque such that only the fluid cartridge 228 is visible through the housing 546.

In some embodiments, the fluid delivery device 110 includes an adhesive to facilitate attachment of the fluid delivery device 110 to the skin surface 544 of the user (see e.g. FIG. 9A). The adhesive strength should preferably be sufficient to adhere the fluid delivery device 110 to the skin surface 544 of the user for the duration of treatment with the drug-filled fluid delivery device 110. Thus, adhesive strength can vary depending on the duration of treatment (e.g., 72 hours, 48 hours, 24 hours, 18 hours, 12 hours, etc.). Moreover, the adhesive should be such that the fluid delivery device 110 is easily removable without undue discomfort or pain or difficulty upon completion of use. In some embodiments, the adhesive can be relieved in certain areas, e.g., in the area of the hydraulic basal chamber 314 (see e.g. area 542a in FIG. 2), the fluid reservoir 324 (see e.g. area 542b in FIG. 2) and/or proximate the needle 312 (see e.g. area 542c in FIG. 2), to facilitate contact of the fluid delivery device 110 with the skin surface 544 of the user.

The adhesive can be combined with a pad to form an adhesive patch 542. In one embodiment, the adhesive patch 542 is a non-woven foam pad. In one embodiment, the adhesive patch 542 is comprised of a medical foam adhesive manufactured by 3M®. In one embodiment, the adhesive patch 542 is comprised of 3M® 9776 material. In one embodiment, the outer dimension of the adhesive patch 542 extends beyond the outer dimensions of the housing 546 to allow greater adhesive surface area and/or greater flexibility of the adhesive patch 546 to contour to the user's body shape. In certain embodiments, extended area is, for example, about 0.010 inches, 0.100 inches, 0.250 inches, 0.500 inches or more from the housing 546. The adhesive patch 542 can be capable of movement (e.g. flexing, stretching) in multiple orientations to improve comfort of wear and reduce pinching or tightness or the wearer's perception of pinching or tightness. In one embodiment, the adhesive is initially covered by a removable film 292 (see FIG. 2). In one embodiment, the film 292 includes a tab 292a extending outwardly from the adhesive patch 542 to facilitate removal from the adhesive patch 542 just prior to applying the fluid delivery device 110 to the skin surface 544.

Referring to FIGS. 16A-16B, in exemplary use, the user removes the fluid delivery device 110 from a storage package (not shown). The user can then fill the fluid cartridge 228 with the fluid. In one embodiment, the fluid cartridge 228 is pre-filled. Once the fluid cartridge 228 is filled, the user can remove the button cover 662 exposing the needle button 1680 and simultaneously activating the basal actuator 320. Referring to FIG. 9A, the user can then remove the film 292 from the adhesive patch 542 and place the fluid delivery device 110 on the skin surface 544. In other embodiments, the fluid delivery device 110 is placed on the skin surface 544 before removing the button cover 662. Once the fluid delivery device 110 is on the skin surface 544 and the button cover 662 is removed, the user can then depress the needle button 1680 to engage the needle 312 (see FIG. 18) and fluidly couple the user and the fluid reservoir 324. Once the needle 312 is engaged and when appropriate, the user can then activate the bolus release button 964 (FIG. 9A) and then activate the bolus button 966 (FIG. 9B) to deliver a bolus dosage. Once the delivery period (e.g. 24 hours) is complete or the user otherwise wants to remove the fluid delivery device 110, the user depresses the lock button 1886 (see FIGS. 23A-23C) to retract the needle 312 into the housing 546 (FIG. 22). Once the needle 312 is shrouded by the housing 546, the user can then remove the fluid delivery device 110 from the skin surface 544, dispose the fluid delivery device 110 and repeat the above steps to install a fresh fluid delivery device 110.

In certain embodiments, the half-life in a subject or patient of an active ingredient (e.g., cannabinoid) in a pharmaceutical composition as described herein delivered using a fluid delivery device as described herein is extended at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer as compared to the same or similar pharmaceutical composition delivered orally. In another embodiment, the half-life in a subject or patient of an active ingredient (e.g., cannabinoid or cannabidiol) in a pharmaceutical composition is at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 36 hours, at least about 48 hours, at least about 60 hours, at least about 72 hours, at least about 84 hours, at least about 96 hours, at least about 108 hours, or at least about 120 hours.

Other Embodiments and Equivalents

The section headings used herein are for organizational purposes only and are not to be construed as limiting the subject matter described.

It is to be understood that the methods described herein are not limited to the particular methodology, protocols, subjects, and sequencing techniques described herein and as such can vary. It is also to be understood that the terminology used herein is for the purpose of describing particular embodiments only, and is not intended to limit the scope of the methods and compositions described herein, which will be limited only by the appended claims. While some embodiments of the present invention have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein. Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps can be varied and still remain within the spirit and scope of the present invention.

While some embodiments have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein can be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments can or cannot be part of the claimed invention and various features of the disclosed embodiments can be combined. The words "right", "left", "lower" and "upper" designate directions in the drawings to which reference is made. The words "inwardly" and "outwardly" refer to directions toward and away from, respectively, the geometric center of the fluid delivery device. Unless specifically set forth herein, the terms "a", "an" and "the" are not limited to one element but instead should be read as meaning "at least one".

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

It is to be understood that at least some of the figures and descriptions of the invention have been simplified to focus on elements that are relevant for a clear understanding of the invention, while eliminating, for purposes of clarity, other elements that those of ordinary skill in the art will appreciate can also comprise a portion of the invention. However, because such elements are well known in the art, and because they do not necessarily facilitate a better understanding of the invention, a description of such elements is not provided herein.

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

The invention is also described in the following aspects:

Aspect 1: a method comprising:

obtaining an ambulatory fluid delivery device;

positioning the ambulatory fluid delivery device onto or adjacent to a surface of the subject; and administering a generally constant amount of a pharmaceutical composition including a cannabinoid to the subject subcutaneously over an extended period of time.

Aspect 2: a fluid delivery device for delivering a generally constant amount of a pharmaceutical composition comprising a cannabinoid to a subject, the fluid delivery device comprising:

a hydraulic pump chamber containing and contacting a first amount of a hydraulic fluid and configured to urge a fluid reservoir piston in a fluid reservoir to deliver the generally constant amount of the pharmaceutical composition within the fluid reservoir through a needle to the subject subcutaneously over a period of time.

Aspect 3: a fluid delivery device comprising:

a hydraulic pump chamber having a rigid sidewall containing and contacting a first amount of a hydraulic fluid and configured to urge a fluid reservoir piston in a fluid reservoir to deliver a pharmaceutical composition within the fluid reservoir to a patient; said pharmaceutical composition comprising: a cannabinoid;

one or more vehicles;

and, optionally, one or more excipients, wherein the concentration of the cannabinoid in the composition is at least about 25 grams per liter (g/L), and wherein the viscosity of the composition is less than about 420 cP, as measured at 25 degrees Celsius;

a first actuator having a first actuator piston;

a first hydraulic reservoir chamber coupled to the first actuator piston and having a second amount of the hydraulic fluid;

a flow restrictor fluidly coupling the first hydraulic reservoir chamber and the hydraulic pump chamber to one another;

a second hydraulic reservoir chamber having a third amount of the hydraulic fluid and fluidly coupled with the hydraulic pump chamber, independent of the first hydraulic reservoir; and a second actuator having a second actuator piston coupled to the second hydraulic reservoir chamber.

Aspect 4: The fluid delivery device of any of aspects 1-3, wherein the cannabinoid is selected from the group consisting of cannabidiol (CBD), cannabinol (CBN), cannabichromene (CBC), cannabigerol (CBG), cannabidivarin (CBV), and a derivative thereof.

Aspect 5: The fluid delivery device of any of aspects 1-4, wherein the cannabinoid is cannabidiol.

Aspect 6: The fluid delivery device of any of aspects 1-5, wherein the concentration of the cannabinoid is at least about 50 g/L.

Aspect 7: The fluid delivery device of any of aspects 1-6 wherein the concentration of the cannabinoid is at least about 100 g/L.

Aspect 8: The fluid delivery device of any of aspects 1-7, wherein the viscosity of the pharmaceutical composition is less than about 100 cP.

Aspect 9: The fluid delivery device of any of aspects 1-8, wherein the viscosity of the pharmaceutical composition is less than about 50 cP.

Aspect 10: The fluid delivery device of any of aspects 3-9, when dependent on aspect 3, wherein the one or more vehicles comprises propylene glycol.

Aspect 11: The fluid delivery device of any of aspects 3-10, when dependent on aspect 3, wherein the one or more vehicles comprises transcutol.

Aspect 12: The fluid delivery device of any of aspects 3-11, when dependent on aspect 3, wherein the one or more vehicles comprises a plurality of vehicles, and the plurality of vehicles comprises propylene glycol and transcutol.

Aspect 13: The fluid delivery device of aspect 12, wherein the ratio of the propylene glycol to the transcutol is about 95:5 volume by volume (v/v).

Aspect 14: The fluid delivery device of any of aspects 1-13, wherein, when the device is placed on a surface of the subject, the fluid reservoir containing the pharmaceutical composition is in contact with the surface of the subject, thereby maintaining a temperature of the pharmaceutical composition.

Aspect 15: The fluid delivery device of any of aspects 1-14, wherein the temperature of the pharmaceutical composition is about the same as the temperature of the surface of the subject.

Aspect 16: The fluid delivery device of any of aspects 3-14, when dependent on aspect 3, wherein the flow restrictor limits the transfer of the hydraulic fluid from the first hydraulic reservoir chamber to the hydraulic pump chamber to deliver the pharmaceutical composition from the fluid reservoir at a sustained basal rate.

Aspect 17: The fluid delivery device of aspect 16, wherein the sustained basal rate is constant.

Aspect 18: The fluid delivery device of aspect 16 or 17, wherein the sustained basal rate is over a period of more than 5 hours.

Aspect 19: The fluid delivery device of any of aspects 16-18, wherein the sustained basal rate is over a period of approximately 24 hours.

Aspect 20: The fluid delivery device of any of aspects 3-19, when dependent on aspect 3, wherein the second actuator is selectably actionable to transfer the hydraulic fluid from the second hydraulic reservoir chamber into the hydraulic pump chamber at discrete intervals to deliver a bolus dosage of the pharmaceutical composition in addition to the sustained basal rate.

Aspect 21: The fluid delivery device of any of aspects 3-20, when dependent on aspect 3, wherein the first and second actuators include compression springs.

Aspect 22: The fluid delivery device of any of aspects 2-21, when dependent on aspect 2 or 3, wherein the hydraulic fluid has a viscosity of approximately ISO VG 1500 or more when in use.

Aspect 23: The fluid delivery device of any of aspects 3-22, when dependent on aspect 3, wherein the second hydraulic reservoir is positioned between the second actuator and the hydraulic pump chamber.

Aspect 24: The fluid delivery device of any of aspects 3-23, when dependent on aspect 3, wherein the flow restrictor is a fixed aperture.

Aspect 25: The fluid delivery device of any of aspects 2-24, when dependent on aspect 2 or 3, further comprising:
the fluid reservoir piston, the fluid reservoir piston configured to sealingly slide along an inner wall of a hydraulic housing.

Aspect 26: The fluid delivery device of any of aspects 2-25, when dependent on aspect 2 or 3, wherein the fluid reservoir piston separates the hydraulic housing into the hydraulic pump chamber and the fluid reservoir.

Aspect 27: A pharmaceutical composition for subcutaneous injection, said composition comprising:
a cannabinoid;
one or more vehicles;
and, optionally, one or more excipients,
wherein the concentration of the cannabinoid in the composition is at least about 25 grams per liter (g/L), and
wherein the viscosity of the composition is less than about 420 centipoise (cP), as measured at 25 degrees Celsius.

Aspect 28: The composition of aspect 27, wherein the composition is a liquid formulation.

Aspect 29: The composition of aspect 27, wherein the cannabinoid is selected from the group consisting of cannabidiol (CBD), cannabinol (CBN), cannabichromene (CBC), cannabigerol (CBG), cannabidivarin (CBV), and a derivative thereof.

Aspect 30: The composition of aspect 29, wherein the cannabinoid is cannabidiol.

Aspect 31: The composition of aspect 27, wherein the concentration of the cannabinoid is at least about 50 g/L.

Aspect 32: The composition of aspect 27, wherein the concentration of the cannabinoid is at least about 100 g/L.

Aspect 33: The composition of aspect 27, wherein the viscosity of the composition is less than about 100 cP.

Aspect 34: The composition of aspect 27, wherein the viscosity of the composition is less than about 50 cP.

Aspect 35: The composition of aspect 27, wherein the one or more vehicles comprises propylene glycol.

Aspect 36: The composition of aspect 27, wherein the one or more vehicles comprises transcutol.

Aspect 37: The composition of aspect 27, wherein the one or more vehicles comprises a plurality of vehicles, and the plurality of vehicles comprises propylene glycol and transcutol.

Aspect 38: The composition of aspect 37, wherein the ratio of the propylene glycol to the transcutol is about 95:5 volume by volume (v/v).

Aspect 39: a method of administering a pharmaceutical composition to a subject, the method comprising:
obtaining a fluid delivery device, said fluid delivery device comprising:
a hydraulic pump chamber having a rigid sidewall containing and contacting a first amount of a hydraulic fluid and configured to urge a fluid reservoir piston in a fluid reservoir to deliver a pharmaceutical composition within the fluid reservoir to a patient; said pharmaceutical composition comprising:
a cannabinoid;
one or more vehicles;
and, optionally, one or more excipients,
wherein the concentration of the cannabinoid in the composition is at least about 25 grams per liter (g/L), and wherein the viscosity of the composition is less than about 420 centipoise (cP), as measured at 25 degrees Celsius;
a first actuator having a first actuator piston;
a first hydraulic reservoir chamber coupled to the first actuator piston and having a second amount of the hydraulic fluid;
a flow restrictor fluidly coupling the first hydraulic reservoir chamber and the hydraulic pump chamber to one another; a second hydraulic reservoir chamber having a third amount of the hydraulic fluid and fluidly coupled with the hydraulic pump chamber, independent of the first hydraulic reservoir; and
a second actuator having a second actuator piston coupled to the second hydraulic reservoir chamber.
positioning the fluid delivery device adjacent to a surface of the subject;
administering the pharmaceutical composition to the subject over a period of time.

Aspect 40: The method of aspect 39, wherein the concentration of the cannabinoid in the composition is at least about 25 grams per liter (g/L).

Aspect 41: The method of the aspect 39, wherein the composition is a liquid formulation.

Aspect 42: The method of aspect 39, wherein the cannabinoid is selected from the group consisting of cannabidiol (CBD), cannabinol (CBN), cannabichromene (CBC), cannabigerol (CBG), cannabidivarin (CBV), and a derivative thereof.

Aspect 43: The method of aspect 42, wherein the cannabinoid is cannabidiol.

Aspect 44: The method of aspect 39, wherein the concentration of the cannabinoid is at least about 50 g/L.

Aspect 45: The method of aspect 39, wherein the concentration of the cannabinoid is at least about 100 g/L.

Aspect 46: The method of aspect 39, wherein the viscosity of the composition is less than about 100 cP.

Aspect 47: The method of aspect 39, wherein the viscosity of the composition is less than about 50 cP.

Aspect 48: The method of aspect 39, wherein the one or more vehicles comprises propylene glycol.

Aspect 49: The method of aspect 39, wherein the one or more vehicles comprises transcutol.

Aspect 50: The method of aspect 39, wherein the one or more vehicles comprises a plurality of vehicles, and the plurality of vehicles comprises propylene glycol and transcutol.

Aspect 51: The method of aspect 50, wherein the ratio of the propylene glycol to the transcutol is about 95:5 volume by volume (v/v).

Aspect 52: The method of aspect 39, wherein the subject has one or more conditions selected from the group consisting of ALS, Alzheimer's, antibacterial resistant infections, anxiety, atherosclerosis, arthritis, asthma, cancer, colitis, Crohn's, diabetes, depression, endocrine disorders, epilepsy, seizures, fibromyalgia, glaucoma, heart disease, Huntington's, inflammation, irritable bowel syndrome (IBS), kidney disease, liver disease, motion sickness, nausea, neurodegeneration, neuropathic pain, neuropathy, obesity, obsessive compulsive disorder (OCD), osteoporosis, Parkinson's, prion diseases, Mad Cow disease, post-traumatic stress disorder (PTSD), rheumatism, schizophrenia, sickle cell anemia, skin conditions (e.g., psoriasis, dermatitis, allergic inflammation, chronic pruritus), sleep disorders (e.g., sleep-wake disorders, apnea), spinal cord injury, stress, stroke, and traumatic brain injury (TBI).

Aspect 53: The method of aspect 39, wherein the method is used to treat a condition in the subject, said condition selected from the group consisting of ALS, Alzheimer's, antibacterial resistant infections, anxiety, atherosclerosis, arthritis, asthma, cancer, colitis, Crohn's, diabetes, depression, endocrine disorders, epilepsy, seizures, fibromyalgia, glaucoma, heart disease, Huntington's, inflammation, irritable bowel syndrome (IBS), kidney disease, liver disease, motion sickness, nausea, neurodegeneration, neuropathic pain, neuropathy, obesity, obsessive compulsive disorder (OCD), osteoporosis, Parkinson's, prion diseases, Mad Cow disease, post-traumatic stress disorder (PTSD), rheumatism, schizophrenia, sickle cell anemia, skin conditions (e.g., psoriasis, dermatitis, allergic inflammation, chronic pruritus), sleep disorders (e.g., sleep-wake disorders, apnea), spinal cord injury, stress, stroke, and traumatic brain injury (TBI).

Aspect 54: The method of aspect 39, wherein the half-life of the cannabinoid is at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 36 hours, at least about 48 hours, at least about 60 hours, at least about 72 hours, at least about 84 hours, at least about 96 hours, at least about 108 hours, or at least about 120 hours.

Aspect 55: The method of aspect 39, wherein the fluid reservoir is comprised of a material having a low specific heat capacity, thereby maintaining a temperature of the fluid in the fluid reservoir at or about the same temperature as the subject.

EXAMPLES

Example 1: Pharmacokinetics of Cannabidiol (CBD) Delivered Via 24-Hour Subcutaneous Infusion in Fasting Dogs We investigated the pharmacokinetics (PK) of CBD delivered over a single 24-hour period using the fluid delivery device of the present disclosure (e.g., a subcutaneous infusion device) in dogs. Two CBD dosage regimens (40 mg/24 h and 76 mg/24 h) were tested via the fluid delivery device, with PK evaluated at timepoints out to 48 h from the start of infusion. Both dosages displayed rapid absorption and distribution with CBD levels in blood detected within an hour of the beginning of infusion, followed by prolonged elimination with CBD still detectable 24 h after completion of fluid delivery device infusion. To our knowledge this is the first report of subcutaneous infusion of CBD. The fluid delivery device provides an attractive avenue for administration of CBD with several distinct advantages including elimination of toxic metabolites produced by liver metabolism, minimization of the impact of variation in CBD metabolism in the general population, dramatic improvement of abbreviated half life, and superior bioavailability along with the ability to dramatically lower the overall amount of drug needed to achieve therapeutic levels. These features contribute to a dramatically improved risk-reward profile for a CBD isolate therapeutic and open the door to reliable, uniform dosing providing practitioners and patients an additional level of comfort and peace of mind.

Example 2: Subcutaneous Infusion in Male Beagle Dogs

Objective: To determine exposure of Sponsor's test article(s) (CBD, apomorphine) after subcutaneous (SC) infusion in male Beagle dogs (Non-Crossover).

STUDY TIMETABLE: Study will be initiated within 7 days after protocol signoff and test article receipt.

| TEST ARTICLE DESCRIPTION: A complete description of the test articles is contained in Appendix 1. | |
| --- | --- |
| Amount of Formulation Required: | Approximately 15 grams CBD and 0.5 g apomorphine will be provided by the Sponsor. |
| Storage Conditions of Formulation: | Will store compound as instructed by received packing. |

| SOLUBILITY ASSESSMENT | |
| --- | --- |
| Dose Vehicle Development | Target dose concentration: 100 mg/mL CBD, 25 mg/mL Apomorphine |
| Prepare and evaluate test compound solubility (visual estimation) in up to three different dosing vehicles using the following formulation approaches | a. Assess solubility in co-solvents b. Assess solubility in liquid co-solvent/surfactant mixture c. Assess effects solubility with complexing agents |

| Test Animal Description | |
| --- | --- |
| Species: | *Canis familiaris* |
| Initial Age: | 2-6.5 yrs. |
| Sex: | Male |
| Breed: | Beagle |
| Initial Body Weight: | ~8-14 kg |
| Source of Animals: | Marshall Bioresources, North Rose, New York |
| Identification Method: | Animals will be housed one per cage. They will be assigned a study number and animals will be identified by ear tag and cage label. |
| Experimental Unit: | Individual animal |
| Replicates per Treatment: | N = 4 per dose group. Total of 12 (non-crossover) |
| Inclusion Criteria: | Animals will be healthy at the start of the trial: |
| Exclusion Criteria: | Any of the above inclusion criteria out of specification. |
| Blinding of Study: | The study will not be blinded. |

| Test System Management | |
| --- | --- |
| Acclimation/Conditioning: | Duration of washout period will not be less than seven days. |
| Anticipated Housing: | Animals will be housed one per cage. A single room will be used. |

| Study Design: | |
| --- | --- |
| Breed (Sex): | Beagle (Male) |
| Feeding Schedule: | Animals will be fasted for a minimum of twelve hours prior to dosing, and food will be returned four hours post dose. Water will be supplied ad libitum. |

-continued

| Study Design: | |
| --- | --- |
| Solubility Assessment: | Solubility assessment was conducted in co-solvents, mixture with surfactants, and complexing agent (HPBCD) suitable for the chosen route of administration. |
| Formulation Preparation: | Will be prepared by ASC within 20 hours of SC infusion. Pump will be hand filled with 22 g needle to ensure accuracy of volume in the device. Three aliquots of dosing solution will be set aside for BA evaluation. |
| Safety Precautions: | Routine |
| Adverse Reaction: | Mild emesis has been present in higher doses. |

| Study Design (Non-Crossover): | | | | | | | |
| --- | --- | --- | --- | --- | --- | --- | --- |
| Group # | Test Article | Dose Route | N= (Male) | Dose Conc. (Male) | Dose Volume (ml/kg) | Vehicle | Blood Sampling Time Points |
| 1 | CBD | SC infusion | 4 | 100 | 400 µL over 24 hrs. | 95% Propylene Glycol/5% Transcutol | *Pre-dose, 5, 15, 30, 45 min, 1, 2, 3, 4, 5, 6, |
| 2 | CBD | | 4 | 100 | 760 µL over 24 hrs. | 95% Propylene Glycol/5% Transcutol | 7, 8, 10, 12, 18 24, 30, 36 and 48 hours post infusion start |
| 3 | Apomorphine | | 4 | 25 mg/ml | 400 µL over 24 hrs. | 30% PG/5% Labrasol/ 0.1% sodium Bisulfite/ 64.9% SWFI | |

*Phase take sample at accurate time, no deviations more than ± 10 min.
Bolus time points: A total of 4 bolui will be given at 5, 15, 30 and 45 minutes. At the 1 hour, 2 boli will be given.
Wait 10-15 sec in between each bolus to allow sufficient time for device to deliver dose.

| Blood Sample Site/Volume: | Jugular vein, or other suitable vessel, ~2 mL |
| --- | --- |
| Type of Blood Tubes: | K₂EDTA |
| Type of Sample: | Plasma (~400 uL) |
| Sample Storage and Shipment: | Stored atound −70° C. until analysis by ASC bioanalytical department. |
| Washout Interval: | Minimum 7-day washout |

| Dosing | |
| --- | --- |
| Frequency: | Formulations will be administered to the animals at time 0 on appropriate day. |
| Procedure: | Subcutaneous infusion over 24 hours. The scapular region will be shaved and cleaned for placement of device. Once the device is in place, Vet wrap followed by elasticon wrap will be used to help ensure the device stays in place. After 24 hrs, the device will be removed and disposed of according to ASC SOP. If the device comes off prior to 12 hour time point, the needle will be examined and unit will be placed back on animal. Time of event will be recorded. If the device comes off post 12 hours, time will be noted and device discarded in accordance with ASC SOP. |

| Sampling | |
| --- | --- |
| Frequency: | See Section 5.3 - Study Design |
| Blood Collection: | Each blood sample will be collected from the dog, |

-continued

| Sampling | |
| --- | --- |
| | jugular vein, or other suitable vessel via direct venipuncture, placed into a tube containing K₂EDTA as the anticoagulant, and inverted several times to mix. Blood sample will be kept on wet ice until centrifugation. |
| Plasma Preparation and Storage: | Blood samples will be centrifuged at a temperature of 4° C. at 3,000 xg, for 5 minutes. All samples will be maintained chilled throughout processing. Plasma will be collected, aliquoted into cluster tubes populated in a 96 well plate, and placed in a freezer set to maintain ~−70° C. until analysis. |

-continued

| Sampling | |
| --- | --- |
| Sample Shipment: | Plasma samples will be analyzed at Absorption Systems California, LLC. |

| Documentation | |
| --- | --- |
| Dosing and Sampling: | Will be documented on the dosing and blood collection data sheets. |
| Observations & Adverse Reactions: | Will be documented on the dosing and blood collection data sheets. |

Animal Removal: The reason for removal of any animal from the study will be documented in the final report, Quality Assurance: This study is not intended to be conducted in accordance with U.S. FDA regulations 21 CFR Pant 58, Laboratory Practice for Nonclinical Laboratory Studies (and all amendments, effective Jun. 20, 1979) However, it will be conducted in compliance with the Standard Operating Procedures at Absorption Systems California, LLC.

Considerations of Alternatives: The dog is a standard model for non-clinical pharmacokinetic studies, for which there is a large historical database. To the best of our knowledge, this study does not unnecessarily dupli-cate previous experiments. Additionally, the dosing and blood collection procedures in this study are not likely or intended to cause more than momentary slight pain or distress.

Testing in Lower Species: This test article has been tested in lower species at the dose in this study with no observable adverse events.

---

ANALYTICAL METHOD EVALUATION:

| | | |
|---|---|---|
| Method Development: | 1. | Optimize MS detection for suitable sensitivity |
| | 2. | Evaluates LC detection for suitable sensitivity |
| | 3. | Standard curve with minimum 6 points |
| Incurred Sample Analysis: | 1. | Samples will be analyzed in a single batch at the conclusion of the study |
| | 2. | Two methods will be developed for bioanalysis of plasma samples. One method for CBD and one method for Apomorphine. |
| | 3. | Determine the concentrations of test article in dosing solutions and incurred samples using a generic LC-MSMS method with a minimum 6 point calibration curve. |
| | 4. | The analytical rigor does not include a pre-study validation, and QCs will not be used for sample analysis. |
| | 5. | Dosing solutions will be normalized in matched matrix (dog plasma) and analyzed (n = 3) in the same analytical batch as the incurred samples, as applicable. |
| | 6. | Non-compartmental analysis is used to determine PK parameters for each test article. |
| Assay Acceptance Criteria: | | At least 60% of the calibration standards must be within ±20% of nominal, except at the LLOQ where ±25% is acceptable, in order for the analytical run to pass. |

---

REPORT GENERATION:

| | | |
|---|---|---|
| Materials and Methods | | |
| Data Processing and Interpretation: | | The nominal dosing level will be used in all data analysis |
| Results and Conclusions: | 1. | Visually estimated solubility in up to three dose vehicles. |
| | 2. | Instructions for dose vehicle prototype preparation. |
| | 3. | In-life observations on each dog |
| | 4. | A table containing test article concentration in plasma samples at each time point |
| | 5. | Dosing Solution Analysis |
| | 6. | Plasma concertration vs. time profiles |
| | 7. | A table containing appropriate pharmacokinetic parameters for each dose route |
| | a. | Non-compartmental analysis is used to determine PK parameters for each test article |
| | b. | AUC, half-life, Clearance, Volume of Distribution at steady state, $C_{max}$, $t_{max}$, and Mean Residence Time (MRT) for each article |
| Appendices: | 1. | Animal data sheets |
| | 2. | Analytical methodology |
| Express Plus Report: | | The draft report will be issued in ASLP Express Plus format |

---

DISPOSITIONS:

| | |
|---|---|
| Live Animals: | Animals may be returned to the ASC colony after the final blood sample has been collected. |
| Test Article Storage and Shipment: | Test article will be stored in the desiccator. |
| Dosing Solution Storage and Shipment: | Once the device has been removed from animal, it will he discarded in sharps container, in accordance to ASC SOP. |

---

RESPONSIBILITIES:

| | |
|---|---|
| Animal Care & Feeding: | Absorption Systems California, LLC |
| Treatment Group Assignment: | Absorption Systems California, LLC |
| Veterinary Care: | Absorption Systems California, LLC |
| Test & Control Article Preparation: | Absorption Systems California, LLC |
| Test & Control Article | Absorption Systems California, LLC |

---

-continued

RESPONSIBILITIES:

| | |
|---|---|
| Administration: | |
| Laboratory Testing: | Absorption Systems California, LLC |
| Necropsy, if applicable: | Absorption Systems California, LLC |
| Archivist: | Absorption Systems California, LLC |
| Sample Analysis: | Absorption Systems California, LLC |
| Statistical Analysis: | Absorption Systems California, LLC |
| Written Report (in-life only): | Absorption Systems California, LLC |

---

APPENDIX 1

Test Article Description

| Test Article: | CBD | Apomorphine |
|---|---|---|
| Lot: | Batch #81127 | |
| Chemical Name: | Cannabidiol C21H30O2 | $C_{17}H_{17}NO_2 \cdot HCl \cdot \frac{1}{2}H_2O$ |

APPENDIX 1-continued

| Test Article Description | | |
|---|---|---|
| Molecular Weight: Formula Weight: Salt Correction Factor: | 314.464 g/mol | 312.79 (hemihydrate)g/mol |
| Purity: | 100% | |
| Storage Conditions: | Room Temperature | Stable under recommended storage conditions (protect from light). It gradually acquires a green color on exposure to light and air |
| Stability: | | |
| Solubility: | | Sparingly soluble in water and in alcohol; soluble in water at 80°; very slightly soluble in chloroform and in ether; practically insoluble in Toluene. |

APPENDIX 2

| Acceptable Time Range for Sampling | |
|---|---|
| Scheduled Collection Time | Acceptable Time Range |
| 0-2 min | ±10 sec |
| >2-5 min | ±20 sec |
| >5-15 min | ±45 sec |
| >15-60 min | ±2 min |
| >1-3 hr | ±5 min |
| >3-12 hrs | ±10 min |
| >12-24 hrs | ±10 min |
| Day 1 (>24 hrs) | ±10 min |

In this study, the exposure of test articles CBD and Apomorphine were evaluated in male Beagle dogs following subcutaneous (SC) infusion administration. Blood samples were collected up to 48 hours post-dose, and plasma concentrations of test article(s) were determined by LC-MS/MS. Pharmacokinetic parameters were determined using Phoenix WinNonlin (v8.0). The study design is described above.

A summary of the mean pharmacokinetic parameters for test article(s) are shown in the table below.

| Analyte | Group 1 SC infusion CBD | Group 2 SC infusion CBD | Group 3 SC infusion Apomorphine |
|---|---|---|---|
| Animal weight (kg) | 12.7 | 14.0 | 12.1 |
| Dose (mg/kg) | 3.21 | 5.45 | 0.837 |
| $C_{max}$ (ng/mL) | 9.92 | 11.7 | 3.41 |
| $T_{max}$ (hr) | 23.3 | 17.0 | 30.0 |
| $MRT_{last}$ (hr) | 17.6 | 24.3 | 24.4 |
| $AUC_{last}$ (hr*ng/mL) | 221 | 303 | 82.9 |

$C_{max}$: maximum plasma concentration; $t_{max}$: time of maximum plasma concentration; $T_{1/2}$: half-life; $MRT_{last}$: mean residence time, calculated to the last observable time point; $AUC_{last}$: area under the curve, calculated to the last observable time point; $AUC_{\infty}$: area under the curve extrapolated to infinity. NA: not applicable.

Dosing Solution Analysis

The concentrations of the dosing solutions were analyzed by LC-MS/MS. The measured dosing solution concentration is shown in the table below. The dosing solutions were diluted into blank dog plasma and analyzed in triplicate. All concentrations are expressed as mg/mL of the free base. The nominal dose concentration was used in all calculations.

| Test article | Dose group | Route of admin- istration | Nominal dosing Conc. (mg/mL) | Measured Dosing solution Conc. (mg/mL) | % of Nominal |
|---|---|---|---|---|---|
| CBD | 1 &2 | SC infusion | 100 | 104 | 104% |
| Apomorphine | 3 | SC infusion | 25 | 20.5 | 82.1% |

Quantitative Plasma Sample Analysis

Plasma samples were extracted and analyzed using HPLC/MS. Individual and mean concentrations and pharmacokinetic parameters are shown in tables 1-2 below. All data are expressed as ng/mL of the free base. Samples that were below the limit of quantification (1 ng/mL) were excluded from the calculation of mean values. Concentrations versus time data are plotted in FIGS. 24-25.

TABLE 1

Individual and Mean Plasma Concentrations (ng/mL) and Pharmacokinetic Parameters for CBD after Subcutaneous Infusion Administration (40 mg/animal) in Male Beagle dogs (Group 1).

| Time Point (hr) | Animal # | | | | | |
|---|---|---|---|---|---|---|
| | 2099411 | 2048514 | 2229073 | 2231230 | Mean | SD |
| 0 (pre-dose) | BLOQ | BLOQ | BLOQ | BLOQ | BLOQ | NA |
| 0.083 | BLOQ | BLOQ | 5.76 | BLOQ | NC | NA |
| 0.25 | BLOQ | BLOQ | BLOQ | BLOQ | BLOQ | NA |
| 0.5 | BLOQ | 1.03 | 3.19 | 5.61 | 3.28 | 2.29 |
| 0.75 | 2.83 | 2.45 | 1.55 | 3.00 | 2.45 | 0.648 |
| 1 | 2.84 | 1.44 | 2.10 | 4.14 | 2.63 | 1.16 |
| 2 | 5.11 | 3.39 | 4.29 | 2.10 | 3.72 | 1.29 |
| 3 | 7.77 | 5.34 | 4.32 | 12.0 | 7.36 | 3.42 |
| 4 | 2.82 | 1.74 | 2.95 | 8.87 | 4.10 | 3.23 |
| 5 | BLOQ | 4.12 | 2.56 | 8.64 | 5.11 | 3.16 |
| 6 | 4.02 | BLOQ | 4.42 | 9.91 | 6.12 | 3.29 |
| 7 | 6.67 | 1.38 | 3.50 | 10.6 | 5.53 | 4.01 |
| 8 | BLOQ | BLOQ | 5.06 | 6.99 | 6.03 | NA |
| 10 | BLOQ | BLOQ | 2.97 | 8.87 | 5.92 | NA |
| 12 | 4.47 | BLOQ | 5.73 | 4.97 | 5.12 | 0.55 |
| 18 | BLOQ | BLOQ | 3.31 | BLOQ | NC | NA |
| 24 | 9.48 | BLOQ | BLOQ | 8.17 | 8.82 | NA |
| 30 | 14.2 | BLOQ | 5.83 | 14.2 | 11.4 | 4.86 |
| 36 | 9.05 | BLOQ | BLOQ | 6.13 | 7.59 | NA |
| 48 | 4.20 | BLOQ | BLOQ | 6.11 | 5.15 | NA |

TABLE 1-continued

Individual and Mean Plasma Concentrations (ng/mL) and Pharmacokinetic Parameters for CBD after Subcutaneous Infusion Administration (40 mg/animal) in Male Beagle dogs (Group 1).

| Time Point (hr) | Animal # | | | | Mean | SD |
|---|---|---|---|---|---|---|
| | 2099411 | 2048514 | 2229073 | 2231230 | | |
| Animal Weight (kg) | 14.1 | 14.4 | 11.2 | 11.0 | 12.7 | 1.82 |
| Dose (mg/kg) | 2.84 | 2.78 | 3.57 | 3.64 | 3.21 | 0.461 |
| $C_{max}$ (ng/mL) | 14.2 | 5.34 | 5.83 | 14.2 | 9.92 | 5.01 |
| $t_{max}$ (hr) | 30.0 | 3.00 | 30.0 | 30.0 | 23.3 | 13.5 |
| $t_{1/2}$ (hr) | $NC^2$ | $NC^2$ | $NC^2$ | $NC^2$ | NC | NA |
| $MRT_{last}$ (hr) | 26.0 | 3.61 | 16.3 | 24.3 | 17.6 | 10.2 |
| $AUC_{last}$ (hr · ng/mL) | 363 | 19.9 | 127 | 371 | 221 | 175 |
| $AUC_\infty$ (hr · ng/mL) | $NC^2$ | $NC^2$ | $NC^2$ | $NC^2$ | NC | NA |
| Dose-normalized Values[1] | | | | | | |
| $AUC_{last}/D$ (hr · kg · ng/mL/mg) | 128 | 7.17 | 35.7 | 102 | 68.2 | 56.3 |
| $AUC_\infty/D$ (hr · kg · ng/mL/mg) | $NC^2$ | $NC^2$ | $NC^2$ | $NC^2$ | NC | NA |

$C_{max}$: maximum plasma concentration: $t_{max}$: time of maximum plasma concentration: $t_{1/2}$: half-life.: $MRT_{last}$: mean residence time, calculated to the last observable time point: $AUC_{last}$: area under the curve, calculated to the last observable time point: $AUC_\infty$: area under the curve extrapolated to infinity, was not calculated because $t_{1/2}$ was not calculated: ND: not determined: NA: not applicable; BLOQ: below the limit of quantitation (1 ng/mL). NC: not calculated.
[1]Dose-normalized by dividing the parameter by the normal dose in mg/kg.
[2]Not calculated. The half-life $t_{1/2}$ is not applicable for the "consistent dosing matter". Therefore the half-lives were not calculated, which did not allow for $AUC_\infty$ calculation as well.

TABLE 2

Individual and Mean Plasma Concentrations (ng/mL) and Pharmacokinetic Parameters for CBD after Subcutaneous Infusion Administration (76 mg/animal) in Male Beagle dogs (Group 1).

| Time Point (hr) | Animal # | | | | Mean | SD |
|---|---|---|---|---|---|---|
| | 2511283 | 2510805 | 2495491 | 2566053 | | |
| 0 (pre-dose) | BLOQ | BLOQ | BLOQ | BLOQ | BLOQ | NA |
| 0.083 | BLOQ | BLOQ | BLOQ | BLOQ | BLOQ | NA |
| 0.25 | BLOQ | BLOQ | BLOQ | BLOQ | BLOQ | NA |
| 0.5 | BLOQ | BLOQ | BLOQ | BLOQ | BLOQ | NA |
| 0.75 | BLOQ | BLOQ | BLOQ | BLOQ | BLOQ | NA |
| 1 | BLOQ | BLOQ | 3.73 | 6.89 | 5.31 | NA |
| 2 | BLOQ | 3.69 | 5.24 | 5.96 | 4.97 | 2.68 |
| 3 | 2.21 | 3.33 | 3.69 | 8.29 | 4.38 | 2.68 |
| 4 | 3.76 | 2.24 | 1.38 | 5.84 | 3.31 | 1.96 |
| 5 | BLOQ | 2.42 | 2.35 | 1.73 | 2.17 | 0.378 |
| 6 | 4.80 | 2.97 | 3.62 | 10.0 | 5.35 | 3.20 |
| 7 | 3.82 | 3.63 | 3.35 | 8.31 | 4.78 | 2.37 |
| 8 | 1.40 | 2.64 | 3.76 | 12.8 | 5.14 | 5.18 |
| 10 | 3.84 | 3.08 | 3.18 | 6.67 | 4.19 | 1.69 |
| 12 | 3.80 | 5.21 | 4.42 | 10.7 | 6.03 | 3.16 |
| 18 | 1.74 | 5.60 | 2.76 | 13.6 | 5.93 | 5.38 |
| 24 | 10.3 | 17.5 | 3.22 | 7.69 | 9.68 | 5.99 |
| 30 | 6.09 | 17.5 | 5.06 | 7.55 | 9.04 | 5.70 |
| 36 | 3.53 | 11.6 | 3.36 | 5.65 | 6.04 | 3.86 |
| 48 | 5.04 | 15.6 | BLOQ | 4.33 | 8.32 | 6.31 |
| Animal Weight (kg) | 14.8 | 14.7 | 13.7 | 12.8 | 14.0 | 0.942 |
| Dose (mg/kg) | 5.14 | 5.17 | 5.55 | 5.94 | 5.45 | 0.376 |
| $C_{max}$ (ng/mL) | 10.3 | 17.5 | 5.24 | 13.6 | 11.7 | 5.20 |
| $t_{max}$ (hr) | 24.0 | 24.0 | 2.00 | 18.0 | 17.0 | 10.4 |
| $t_{1/2}$ (hr) | $NC^2$ | $NC^2$ | $NC^2$ | $NC^2$ | NC | NA |
| $MRT_{last}$ (hr) | 26.5 | 30.4 | 18.9 | 21.5 | 24.3 | 5.11 |
| $AUC_{last}$ (hr · ng/mL) | 217 | 493 | 129 | 372 | 303 | 162 |
| $AUC_\infty$ (hr · ng/mL) | $NC^2$ | $NC^2$ | $NC^2$ | $NC^2$ | NC | NA |
| Dose-normalized Values[1] | | | | | | |
| $AUC_{last}/D$ (hr · kg · ng/mL/mg) | 42.1 | 95.3 | 23.3 | 62.7 | 55.8 | 30.8 |
| $AUC_\infty/D$ (hr · kg · ng/mL/mg) | $NC^2$ | $NC^2$ | $NC^2$ | $NC^2$ | NC | NA |

$C_{max}$: maximum plasma concentration: $t_{max}$: time of maximum plasma concentration: $t_{1/2}$: half-life.: $MRT_{last}$: mean residence time, calculated to the last observable time point: $AUC_{last}$: area under the curve, calculated to the last observable time point: $AUC_\infty$: area under the curve extrapolated to infinity, was not calculated because $t_{1/2}$ was not calculated: ND: not determined: NA: not applicable; BLOQ: below the limit of quantitation (1 ng/mL). NC: not calculated.
[1]Dose-normalized by dividing the parameter by the normal dose in mg/kg.
[2]Not calculated. The half-life $t_{1/2}$ is not applicable for the "consistent dosing matter". Therefore the half-lives were not calculated, which did not allow for $AUC_\infty$ calculation as well.

Data Analysis

Pharmacokinetic parameters were calculated from the time course of the plasma concentration and are presented in Tables 1-2. Pharmacokinetic parameters were determined with Phoenix WinNonlin (v8.0) software using a non-compartmental model. The maximum plasma concentration (Cmax) and the time to reach maximum plasma concentration (tmax) after PO dosing were observed from the data. The area under the time-concentration curve (AUC) was calculated using the linear trapezoidal rule with calculation to the last quantifiable data point (AUC0-last), and with extrapolation to infinity (AUC∞) if applicable. Plasma half-life (t½) was calculated from 0.693/slope of the terminal elimination phase. Mean residence time, MRT, was calculated by dividing the area under the moment curve (AUMC) by the AUC. Any samples below the limit of quantitation (1 ng/mL) were not used in the calculation of mean values.

Figure 24:
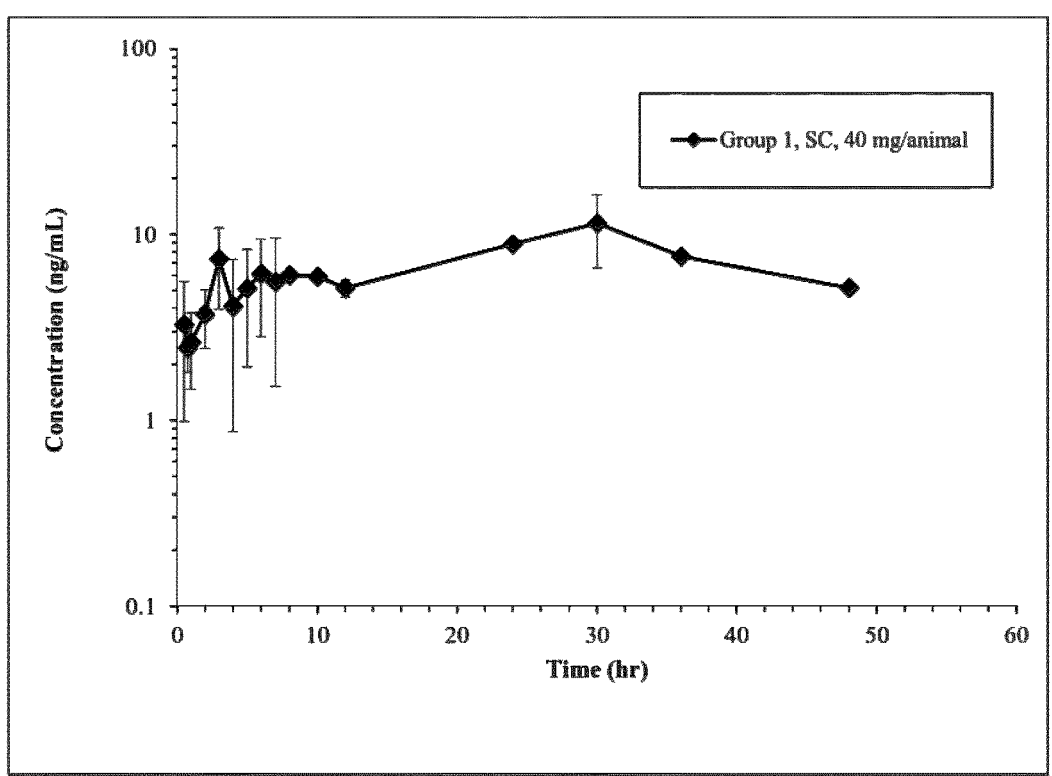
FIG. 24 shows mean plasma concentrations of CBD after subcutaneous infusion administration (40 mg/animal) in male beagle dogs (group 1).
Figure 25:
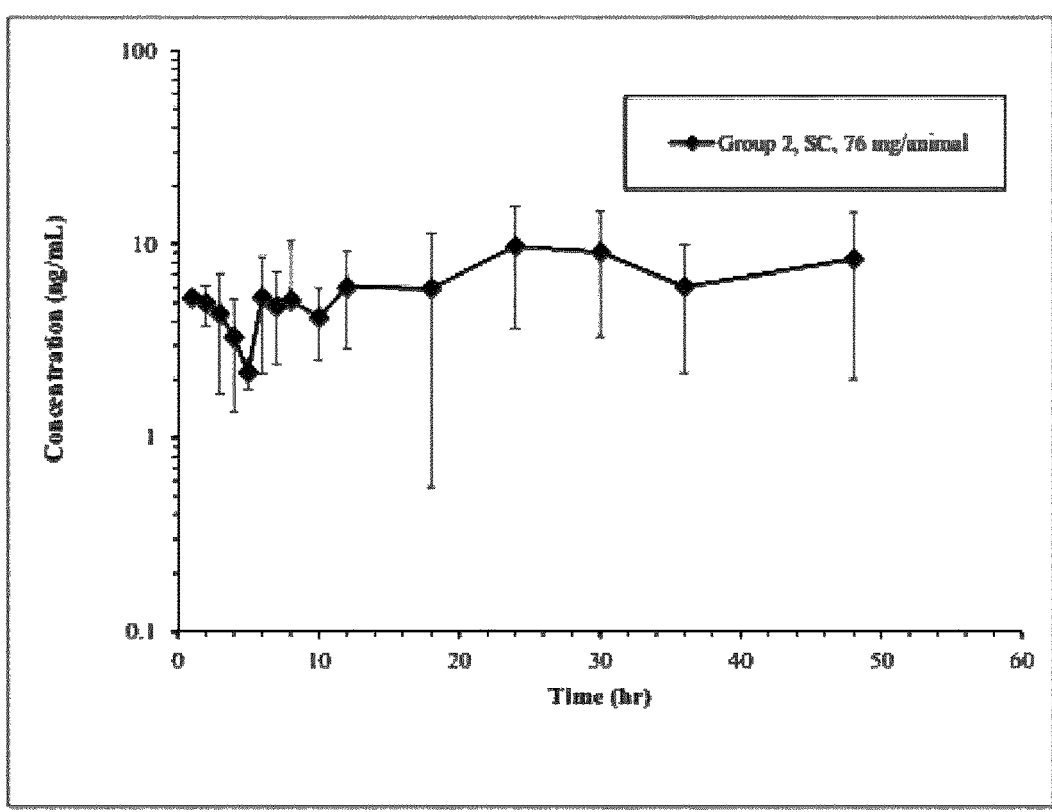
FIG. 25 shows mean plasma concentrations of CBD after subcutaneous infusion administration (76 mg/animal) in male beagle dogs (group 2).

The animal study shows for both group 1 (40 mg CBD/animal) and group 2 (76 mg CBD/animal) a constant concentration of CBD in the blood with a minimal variation is reached after few hours, see FIGS. 24 and 25. The study demonstrates a continuous basal delivery rate over a period of 24 hours, and maximizes therapeutic effect by avoiding the first-pass effect and eliminating peak/trough variations of drug exposure. Use of the pharmaceutical composition for subcutaneously administration according to the invention may offer several distinct advantages over oral dosing including the ability to achieve therapeutic drug concentrations with a fraction of the overall dose, significantly prolonged half life (versus single oral administration), minimization of the variation in CBD metabolism in the general population, and a dramatic reduction in the overall amount of drug metabolized by the liver. These features may contribute to a dramatically improved risk-reward profile for a CBD isolate therapeutic and could open the door to reliable, uniform dosing.

The invention claimed is:

1. A pharmaceutical composition for subcutaneous administration, the composition consisting of:

a cannabinoid;

propylene glycol;

diethylene glycol monoethyl ether; and optionally water for injection;

wherein the concentration of the cannabinoid in the composition is at least about 25 grams per liter (g/L), and wherein the viscosity of the composition is less than about 420 centipoise (cP), as measured at 25 degrees Celsius.

2. The pharmaceutical composition of claim 1, wherein the cannabinoid is cannabidiol (CBD), cannabinol (CBN), cannabichromene (CBC), cannabigerol (CBG), or cannabidivarin (CBV).

3. The pharmaceutical composition of claim 1, wherein (a) the composition is a liquid formulation; and/or (b) the composition is substantially free of Δ9-tetrahydrocannabinol (THC); and/or (c) the concentration of the cannabinoid is at least about 50 g/L or at least about 100 g/L; and/or (d) the viscosity of the composition is less than about 100 cP as measured at 25 degrees Celsius or less than about 50 cP as measured at 25 degrees Celsius; and/or (e) the half-life of the cannabinoid is at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 36 hours, at least about 48 hours, at least about 60 hours, at least about 72 hours, at least about 84 hours, at least about 96 hours, at least about 108 hours, or at least about 120 hours.

4. The pharmaceutical composition of claim 1, wherein the ratio of the propylene glycol to the diethylene glycol monoethyl ether is (a) in the range of about 95:5 volume by volume (v/v) to about 85:15 v/v; or (b) about 95:5 volume by volume (v/v).

5. A method of therapy comprising administering the pharmaceutical composition of claim 1 to a subject.

6. The method of claim 5 wherein the composition is administered (a) subcutaneously; and/or (b) by continuous infusion; and/or (c) as a bolus; and/or (d) both by continuous infusion and as a bolus; and/or (e) by injection.

7. The method of claim 5, wherein the method is for treatment or prevention of one or more conditions selected from the group consisting of (a) ALS, Alzheimer's, antibacterial resistant infections, anxiety, atherosclerosis, arthritis, asthma, cancer, colitis, Crohn's, diabetes, depression, endocrine disorders, epilepsy, seizures, fibromyalgia, glaucoma, heart disease, Huntington's, inflammation, irritable bowel syndrome (IBS), kidney disease, liver disease, motion sickness, nausea, neurodegeneration, neuropathic pain, neuropathy, Taxane Induced Peripheral Neuropathy, obesity, obsessive compulsive disorder (OCD), osteoporosis, Parkinson's, prion diseases, Mad Cow disease, post-traumatic stress disorder (PTSD), rheumatism, schizophrenia, sickle cell anemia, skin conditions, sleep disorders, spinal cord injury, stress, stroke, traumatic brain injury (TBI), behavioral problems in children with ASD, Hyperalgesia in Patients With Deep Endometriosis, Phantom Limb Pain, and reduction of alcohol consumption; or (b) ALS, Alzheimer's, antibacterial resistant infections, anxiety, atherosclerosis, arthritis, asthma, cancer, colitis, Crohn's, diabetes, depression, endocrine disorders, epilepsy, seizures, fibromyalgia, glaucoma, heart disease, Huntington's, inflammation, irritable bowel syndrome (IBS), kidney disease, liver disease, motion sickness, nausea, neurodegeneration, neuropathic pain, neuropathy, obesity, obsessive compulsive disorder (OCD), osteoporosis, Parkinson's, prion diseases, Mad Cow disease, post-traumatic stress disorder (PTSD), rheumatism, schizophrenia, sickle cell anemia, skin conditions, sleep disorders, spinal cord injury, stress, stroke, and traumatic brain injury (TBI).

8. The method of claim 5 wherein oral administration and/or inhalation of the composition is unsuitable for the subject.

9. The method of claim 8 wherein the subject has nausea and/or vomiting.

10. The method of claim 5 wherein the composition is administered by an ambulatory fluid delivery device.

11. The method of claim 10 wherein said fluid delivery device comprises a hydraulic pump chamber containing and contacting a first amount of a hydraulic fluid and configured to urge a fluid reservoir piston in a fluid reservoir to deliver a generally constant amount of the pharmaceutical composition within the fluid reservoir through a needle to the subject subcutaneously over a period of time.

12. The method of claim 10 wherein the fluid delivery device comprises:

a hydraulic pump chamber having a rigid sidewall containing and contacting a first amount of a hydraulic fluid and configured to urge a fluid reservoir piston in a fluid reservoir to deliver a pharmaceutical composition of claim 1 within the fluid reservoir to the subject;

a first actuator having a first actuator piston;

a first hydraulic reservoir chamber coupled to the first actuator piston and having a second amount of the hydraulic fluid;

a flow restrictor fluidly coupling the first hydraulic reservoir chamber and the hydraulic pump chamber to one another;

a second hydraulic reservoir chamber having a third amount of the hydraulic fluid and fluidly coupled with the hydraulic pump chamber, independent of the first hydraulic reservoir; and a second actuator having a second actuator piston coupled to the second hydraulic reservoir chamber.

13. The method of claim 10 wherein (a) said fluid delivery device is positioned adjacent to a surface of the subject; and/or (b) said pharmaceutical composition is administered to the subject over a period of time; and/or (d) the temperature of the pharmaceutical composition is about the same as the temperature of the surface of the subject.

14. The method of claim 11, wherein the hydraulic fluid has a viscosity of approximately ISO VG 1500 or more when in use.

15. The method of claim 12, wherein the flow restrictor limits the transfer of the hydraulic fluid from the first hydraulic reservoir chamber to the hydraulic pump chamber to deliver the pharmaceutical composition from the fluid reservoir at a sustained basal rate.

16. The method of claim 15, wherein the sustained basal rate is (a) constant; and/or (b) over a period of more than 5 hours; and/or (c) over a period of approximately 24 hours.

17. The method of claim 12 wherein (a) the second actuator is selectably actionable to transfer the hydraulic fluid from the second hydraulic reservoir chamber into the hydraulic pump chamber at discrete intervals to deliver a bolus dosage of the pharmaceutical composition in addition to the sustained basal rate; and/or (b) the first and second actuators include compression springs; and/or (c) the second hydraulic reservoir is positioned between the second actuator and the hydraulic pump chamber; and/or (d) the flow restrictor is a fixed aperture; and/or (e) the fluid reservoir is comprised of a material having a low specific heat capacity, thereby maintaining a temperature of the fluid in the fluid reservoir at or about the same temperature as the subject.

18. The method of claim 12, wherein the fluid reservoir piston configured to sealingly slide along an inner wall of a hydraulic housing.

19. The method of claim 18, wherein the fluid reservoir piston separates the hydraulic housing into the hydraulic pump chamber and the fluid reservoir.

* * * * *